United States Patent
Boctor et al.

(10) Patent No.: US 10,806,346 B2
(45) Date of Patent: *Oct. 20, 2020

(54) PHOTOACOUSTIC TRACKING AND REGISTRATION IN INTERVENTIONAL ULTRASOUND

(71) Applicant: The Johns Hopkins University, Baltimore, MD (US)

(72) Inventors: Emad M. Boctor, Baltimore, MD (US); Alexis Cheng, Baltimore, MD (US); Xiaoyu Guo, Baltimore, MD (US); Haichong K. Zhang, Baltimore, MD (US); Russell H. Taylor, Severna Park, MD (US)

(73) Assignee: The Johns Hopkins University, Baltimore, MD (US)

( * ) Notice: Subject to any disclaimer, the term of this patent is extended or adjusted under 35 U.S.C. 154(b) by 1080 days.

This patent is subject to a terminal disclaimer.

(21) Appl. No.: 15/019,696

(22) Filed: Feb. 9, 2016

(65) Prior Publication Data

US 2016/0228090 A1 Aug. 11, 2016

Related U.S. Application Data

(60) Provisional application No. 62/113,918, filed on Feb. 9, 2015.

(51) Int. Cl.
*A61B 5/00* (2006.01)
*A61B 8/00* (2006.01)
(Continued)

(52) U.S. Cl.
CPC .......... *A61B 5/0095* (2013.01); *A61B 5/0059* (2013.01); *A61B 8/0841* (2013.01);
(Continued)

(58) Field of Classification Search
CPC ... A61B 8/4416; A61B 8/0841; A61B 8/5207; A61B 5/0095; A61B 8/58; A61B 8/15;
(Continued)

(56) References Cited

U.S. PATENT DOCUMENTS

| | | | |
|---|---|---|---|
| 4,896,673 A * | 1/1990 | Rose | A61B 8/0833 600/439 |
| 5,551,429 A | 9/1996 | Fitzpatrick et al. | |

(Continued)

FOREIGN PATENT DOCUMENTS

| | | |
|---|---|---|
| CA | 2108098 A1 | 4/1994 |
| EP | 0998238 A1 | 5/2000 |

(Continued)

OTHER PUBLICATIONS

Chan et al. "A needle tracking device for ultrasound guided percutaneous procedures," 2005, Ultrasound in Med. & Biol., vol. 31, No . 11, pp. 1469-1483 (Year: 2005).*

(Continued)

*Primary Examiner* — James M Kish
(74) *Attorney, Agent, or Firm* — Harrity & Harrity, LLP

(57) ABSTRACT

An ultrasound imaging system having real-time tracking and image registration includes a fiducial-marker system comprising an ultrasound transmitter structured to provide a localized ultrasound pulse at an optically observable localized spot on a body of interest. The system further includes an optical imaging system, a two-dimensional ultrasound imaging system, an optical image processing system, and an ultrasound image processing system. The ultrasound imaging system further includes a registration system configured to communicate with the optical image processing system and the ultrasound image processing system to receive information, the registration system being further configured to determine a coordinate transformation that registers the (Continued)

optical image with the two-dimensional ultrasound image based at least partially on information concerning the spatial locations determined for the combined ultrasound and optical fiducial marker observed in the optical image and in the two-dimensional ultrasound image.

27 Claims, 34 Drawing Sheets

(51) Int. Cl.
| | | |
|---|---|---|
| *A61B 8/08* | (2006.01) | |
| *G01S 15/89* | (2006.01) | |
| *A61B 90/00* | (2016.01) | |
| *A61B 8/15* | (2006.01) | |
| *A61B 8/12* | (2006.01) | |

(52) U.S. Cl.
CPC .......... *A61B 8/4416* (2013.01); *A61B 8/5207* (2013.01); *G01S 15/899* (2013.01); *A61B 8/12* (2013.01); *A61B 8/15* (2013.01); *A61B 8/58* (2013.01); *A61B 2090/3995* (2016.02)

(58) Field of Classification Search
CPC .. A61B 8/12; A61B 2090/3995; G01S 15/899
See application file for complete search history.

(56) References Cited

U.S. PATENT DOCUMENTS

| | | | |
|---|---|---|---|
| 6,160,835 | A | 12/2000 | Kwon et al. |
| 6,178,340 | B1* | 1/2001 | Svetliza ............... A61B 5/0059 |
| | | | 600/310 |
| 2004/0105580 | A1 | 6/2004 | Hager et al. |
| 2004/0147810 | A1 | 7/2004 | Mizuno et al. |
| 2005/0049486 | A1 | 3/2005 | Urquhart et al. |
| 2008/0071172 | A1* | 3/2008 | Bruck ................... A61B 5/0059 |
| | | | 600/438 |
| 2008/0123083 | A1 | 5/2008 | Wang et al. |
| 2009/0015626 | A1 | 1/2009 | Murayama |
| 2009/0015826 | A1 | 1/2009 | Ramanujam et al. |
| 2009/0018445 | A1 | 1/2009 | Schers et al. |
| 2009/0054763 | A1 | 2/2009 | Wang et al. |
| 2009/0187099 | A1* | 7/2009 | Burcher ............... A61B 5/0059 |
| | | | 600/430 |
| 2009/0322608 | A1* | 12/2009 | Adams ................... H01Q 1/246 |
| | | | 342/368 |
| 2010/0168561 | A1 | 7/2010 | Anderson |
| 2010/0245769 | A1* | 9/2010 | Zhang .................. A61B 5/0059 |
| | | | 351/219 |
| 2010/0331662 | A1* | 12/2010 | Fukutani ............. A61B 5/0059 |
| | | | 600/407 |
| 2011/0130659 | A1 | 6/2011 | Cinquin et al. |
| 2011/0172530 | A1* | 7/2011 | Slayton .................... A61B 8/00 |
| | | | 600/439 |
| 2012/0253200 | A1* | 10/2012 | Stolka .................... A61B 1/041 |
| | | | 600/459 |
| 2013/0168532 | A1 | 7/2013 | Schmid et al. |
| 2014/0121502 | A1* | 5/2014 | Vignon ................ A61B 8/0841 |
| | | | 600/424 |
| 2014/0378796 | A1* | 12/2014 | Chen .................... A61B 5/6848 |
| | | | 600/328 |
| 2015/0031990 | A1* | 1/2015 | Boctor .................. A61B 8/483 |
| | | | 600/424 |
| 2016/0038119 | A1* | 2/2016 | Desjardins ........... A61B 8/4494 |
| | | | 600/424 |

FOREIGN PATENT DOCUMENTS

| | | |
|---|---|---|
| EP | 1795142 A1 | 6/2007 |
| EP | 2143038 A1 | 1/2010 |
| WO | 9610949 A1 | 4/1996 |
| WO | 9840760 A1 | 9/1998 |
| WO | 0200093 A2 | 1/2002 |
| WO | 0224094 A2 | 3/2002 |
| WO | 2005039391 A2 | 5/2005 |
| WO | 2007115825 A1 | 10/2007 |
| WO | 2008004222 A2 | 1/2008 |
| WO | 2009027277 A2 | 3/2009 |
| WO | 2011063266 A2 | 5/2011 |
| WO | WO 2011/063266 * 5/2011 ............. A61B 19/00 |
| WO | WO-2011/100753 A2 | 8/2011 |
| WO | 2012033552 A1 | 3/2012 |

OTHER PUBLICATIONS

Khosravi et al. "One-step Needle Pose Estimation for Ultrasound Guided Biopsies," Aug. 2007,Proc. 29th International Conference on IEEE EMBS, Lyon, France, pp. 3343-3346 (Year: 2007).*

Zemp et al. "Photoacoustic imaging of the microvasculature with a high-frequency ultrasound array transducer," Jan./Feb. 2007, Journal of Biomedical Optics, vol. 12, No. 1, pp. 010501-1-010501-3 (Year: 2007).*

Simonetti "A guided wave technique for needle biopsy under ultrasound guidance," Mar. 13, 2009, Proc. SPIE 7261, Medical Imaging 2009: Visualization, Image-Guided Procedures, and Modeling, vol. 7261, pp. 726118-1-726118-8 (Year: 2009).*

Zamanizadeh et al. Wavefront Segmentation and Classification for Model-Based Underwater High-Frequency Tomography, 2012, Proc. Oceans 2012, Virginia, U.S. (Year: 2012).*

Hoßbach et al. "Simplified stereo-optical ultrasound plane calibration," Mar. 29, 2013, Proc. SPIE 8675, Medical Imaging 2013: Ultrasonic Imaging, Tomography, and Therapy, vol. 86750, pp. 86750X-1-86750X-7 (Year: 2013).*

Piras et al. ("Photoacoustic needle: minimally invasive guidance to biopsy," Jul. 2013, Journal of Biomedical Optics, vol. 18, No. 7, pp. 070502-1-070502-3, (Year: 2013).*

Wei et al. "Real-Time Integrated Photoacoustic and Ultrasound (PAUS) Imaging System to Guide Interventional Procedures: Ex Vivo Study," Feb. 2015, Published Online Jan. 29, 2015, IEEE Transactions on Ultrasonics, Ferroelectrics, and Frequency Control, vol. 62, No. 2, pp. 319-328, (Year: 2015).*

Mari et al., "Acquire real-time RF digital ultrasound data from a commercial scanner", Electronic Journal «Technical Acoustics», 2007, 3, pp. 1-16 (Year: 2007).*

Cheung et al., "Multi-Channel Pre-Beamformed Data Acquisition System for Research on Advanced Ultrasound Imaging Methods", IEEE Transactions on Ultrasonics, Ferroelectrics, and Frequency Control, vol. 59, No. 2, Feb. 2012. pp. 243-252 (Year: 2012).*

Tsunoi et al., "Compact acoustic-resolution photoacoustic imaging system with fiber-based illumination", Jpn. Journal of Applied Physics, 53(12), 126701 (2014).

Ukimura et al., "Imaging-Assisted Endoscopic Surgery: Cleveland Clinic Experience", *Journal of Endourology*, vol. 22-4, p. in press, Apr. 2008.

Ukimura et al., "Real-Time Transrectal Ultrasound Guidance During Laparoscopie Radical Prostatectomy: Impact on Surgical Margins", Journal of Urology, vol. 175-4, pp. 1304-1310, 2006.

Üstüner et al., "Ultrasound imaging system performance assessment," presented at the 2003 American Association of Physicists in Medicine Annu. Meeting, San Diego, CA, (2003).

v. Vledder et al., "Intra-operative ultrasound elasticity imaging for monitoring of hepatic tumour thermal ablation", HPB (Oxford), vol. 12-10, pp. 717-723, Dec. 2010.

Vagvolgyi, Li-Ming Su, R, Taylor, and G. D. Hager, "Video to CT Registration for Image Overlay on Solid Organs", in 4th Workshop on Aubmented Environments for Medical Imaging and Computer-Aided Surgery, Sep. 10, 2008.

Vagvolgyi, S. Dirnaio, A. Deguet, P. Kazanzides, R. Kumar, C, Hassel., and R, Taylor, "The Surgical Assistant Workstation", in 2008 MICCAI Workshop—Systems and Architectures for Computer Assisted Interventions, New York, Sep. 6, 2008. p. in electronic proceedings at bttp:,//midasjounaal.org/browse/publication/295.

(56) References Cited

OTHER PUBLICATIONS

Valleru et al., "Photoacoustic Imaging: Opening New Frontiers in Medical Imaging", Journal of Clinical Imaging Science, vol. 1-2, pp. 1-7, 2011.
Vyas et al., "Interoperative ultrasound to stereocamera registration using interventional photoacoustic imaging," Proc. SPIE 8316, 83160S (2012).
Wang et al., The developing market for medical robotics. Proceedings of the IEEE 94(9), 1763-1771, Sep. 2006.
Wein et al., "Automatic Registration and Fusion of Ultrasound with CT for Radiotherapy", in Medical Image Computing and Computer Assisted Intervention, 2005, pp. 303-311.
Wexner et al., "The current status of robotic pelvic surgery: results of a multinational interdisciplinary consensus conference", Surgical Endoscopy, vol. 23-, pp. 438-443, 2009.
Wiles et al., Accuracy assessment and interpretation for optical tracking systems. Proceedings of SPIE, 5367, 421-432 (2004).
Xu et al., Photoacoustic imaging in biomedicine, Review of scientific instruments 77, 041101 (2006).
Yao et al., "Photoacoustic tomography: fundamentals, advances and prospects", Contrast Media Mol. Imaging, vol. 6-, pp. 332-345, 2011.
Yin et al., "Fast photoacoustic imaging system based on 320-element linear transducer array," Phys. Med. Biol., 49(7), 1339-1346 (2004).
Yip et al., "3D ultrasound to stereoscopic camera registration through an air-tissue boundary," Med. Image. Comput. Comput. Assist. Interv. 13(2), 626-634 (2010).
Zhang et al., "Coded excitation using periodic and unipolar M-sequences for photoacoustic imaging and flow measurement", Optics Express, 24(1), 17-29, (2016).
Zhang et al., "Photoacoustic reconstruction using beamformed RF data: a synthetic aperture imaging approach", in Proceedings of SPIE, 9419, 94190L, (2015).
Navab et al.,"Camera-augmented mobile C-arm (CAMC) application: 3D recon¬struction using low cost mobile C-arm," Med. Image. Comput. Comput. Assist. Interv. 1679, 688-697 (1999).
Niederhauser et al., "Comparision of laser-induced and classical ultrasound," Proc. SPIE, vol. 4960, pp. 118-123 (2003).
Nikolov et al., "Virtual ultrasound sources in high resolution ultrasound imaging," Proc. SPIE, Progress in biomedical optics and imaging, 3, 395-405 (2002).
Okazawa et al., "Methods for segmenting curved needles in ultrasound images", *Medical Image Analysis*, vol. 10-, pp. 330-342, 2006.
Olgin et al., "Electrophysiological Effects of Long, Linear Atrial Lesions Placed Under Intracardiac Ultrasound Guidance", *Circulation*, vol. 96-, pp. 2715-2721, 1997.
Park et al., "Adaptive beamforming for photoacoustic imaging using linear array transducer," in IEEE Ultrasonics Symp. Proc., 2008, pp. 1088-1091.
Poon et al., "Comparison of calibration methods for spatial tracking of a 3-D ultrasound prove," Ultrasound Med. Biol. 31(8), 1095-1108 (2005).
Prager et al., "Decompression and speckle detection for ultrasound images using the homodyned k-distribution." Pattern Recognition Letters 24.4 (2003): 705-713.
Reed et al., "Intraoperative Fluoroscopic Dose Assessment in Prostate Brachytherapy Patients", *International Journal of Radiation Oncology, Biology, Physics*, vol. 63-1, pp. 301-307, 2005.
Rivaz et al., "Real-Time Regularized Ultrasound Elastography.", *IEEE Trans. Med. Imaging*, vol. 30-4, pp. 928-945, 2011.
Rivaz et al., "Ultrasound Elastography: A Dynamic Programming Approach", IEEE Transactions on Medical Imaging, vol. 27-10, pp. 1373-1377, Oct. 2008.
Rivaz et al., "Ablation Monitoring with Elastography: 2D In-vivoand 3D Ex-vivoStudies", in Med Image Comput Comput Assist Intery ( MICCAI), New York, Sep. 6-10, 2008. pp. 458-466.
Rivaz et al., "Tracked Regularized Ultrasound Elastography for Targeting Breast Radiotherapy", in Med Image Comput Comput Assist Interv. (MICCAI), London, Sep. 20-24, 2009. pp. 507-515.
Rohling et al., "PUPIL: Programmable Ultrasound Platform and Interface Library", in Medical Image Computing and Computer Assisted Interventions, 2003. pp. 424 431.
Seabra et al., "Modeling log-compressed ultrasound images for radio frequency signal recovery." 30th Annual International Conference of the IEEE, Engineering in Medicine and Biology Society (EMBS 2008). 2008.
Stefansic et al., "Registration of Physical Space to Laparoscopic image space for use in minimally invasive hepatic surgery", *IEEE Trans Med Imaging*, vol. 19-10, pp. 1012-1023, Oct. 2000.
Stolka et al., "A 3D-elastography-guided system for laparoscopic partial nephrectomies," Proc. SPIE 7625, 762511 (2010).
Stoll et al., "Passive Markers for Ultrasound Tracking of Surgical Instruments", in Medical Image Computing and Computer-Assisted Interventions, 2005. pp. 41-48.
Su et al., "Photoacoustic imaging of clinical metal needles in tissue", J Biomed Opt,, vol. 15-2, pp, 021309.1-6, 2010.
Su et al., "Photoacoustic imaging of coronary artery stents", Optics Express, vol. 17-22, pp. 19894-19901, 2009.
Su et al., "Photoacoustic imaging of prostate brachytherapy seeds", Biomedical Optics Express, vol. 2-8, pp. 2243-2254, 2011.
Thomenius, "Evolution of Ultrasound Beamformers," Proc. IEEE Ultrasonics Symp, 2, 1615-1622 (1996).
Treeby et al., k-Wave; MATLAB toolbox for the simulation and reconstruction of photoacoustic wave-fields. Journal of Biomedical Optics 15(2), 021314 (2010).
Tsai et al., "A Versatible Camera Calibration Technique for High-Accuracy 3D Machine Vision Metrology Using Off-the-Shelf TV Cameras and Lenses," IEEE Journal of Robotics and Automation, vol. RA3-4, pp. 323-358, 1987.
Tsai et al., "Near-infrared absorption property of biological soft tissue constituents", d: Med. Biol. Eng., vol. 21-, pp. 7-14, 2001.
Hoelen et al., "Three-dimensional photoacoustic imaging of blood vessels in tissue," Opt. Lett. 23(8), 648-650 (1998).
Horn et al., "Closed-form solution of absolute orientation using orthonormal matrices", *J Optical Cos Am*, vol. 5-, pp. 1127-1135, 1988.
Jensen et al., "Calculation of pressure fields from arbitrarily shaped, apodized, and excited ultrasound transducers," IEEE Trans. Ultrason., Ferroelec., Freq. Contr., 39, 262-267 (1992).
Kang et al., Software framework of a real-time pre-beamformed RF data acquisition of an ultrasound research scanner, Proc. SPIE 8320, 83201F (2012).
Kang et al., "Software framework of Real-time photoacoustic imaging system for Prostate Brachytherapy Seeds", in SPIE Medical Imaging, San Diego, Feb. 2012.
Kang et al., "Ultrasound Imaging Software Framework for Real-Time Monitoring of Acoustic Ablation Therapy", in *SPIE Medical Imaging*, San Diego, 2012.
Kang et al., "OpenITGLinlcMUSHC: A Standard Communications Protocol for Advanced Ultrasound Research", *The MIDAS Journal*, 2011.
Kazanzides et al., "The Surgical Assistant Workstation (SAW) in Minimally-Invasive Surgery and Microsurgery", in International Workshop on Systems and Architectures for Computer Assisted Interventions, Beijing, Sep. 24, 2010.
Keil et al., "Ultrasound and CT Registration Quality: Elastography vs. Classical B-Mode", in ISBI, 2009. pp. 967-970.
Kim et al., "Handheld array-based photoacoustic probe for guiding needle biopsy of sentinel lymph nodes", *Journal of Biomedical Optics*, vol. 154-, p. 046010, Jul./Aug. 2010.
Kolkman et al., "Real-time in vivo photoacoustic and ultrasound imaging", J. Biomed. Opt., 13(5), 050510 (2008).
Kolkman et al.,"In vivo photoacoustic imaging of blood vessels with a pulsed laser diode," Laser. Med. Sci. 21(3), 134-139 (2006).
Kortbek et al., "Synthetic Aperture Sequential Beamforming," Proc. in IEEE Int. Ultrasonics Symp., 966-969 (2008).
Ku et al., "Thermoacoustic and Photoacoustic Tomography of Thick Biological Tissues Toward Breast Imaging", Technology in Cancer Research & Treatment, vol. 4-5, pp. 559-565, 2005.

(56) References Cited

OTHER PUBLICATIONS

Kuo et al., Photoacoustic imaging of prostate brachytherapy seeds in ex vivo prostate. in Medical Imaging 2011: Visualization, Image-Guided Procedures, and Modeling, Lake Buena Vista, Feb. 12-17, 7964, 796409 (2011).

Kuo et al., "Real-time photoacoustic imaging of prostate brachytherapy seeds using a clinical ultrasound system," J. Biomed. Opt., 17(6), 066005 (2012).

Kwan et al., "Effect of Advanced Imaging Technology on How Biopsies Are Done and Who Does Them", Radiology, vol. 256-3, Sep. 2010.

Leven et al., "DaVinci canvas: a telerobotic surgical system with integrated, robot-assisted, laparoscopic ultrasound capability," Med. Image. Comput. Comput. Assist. Interv. 8(1), 811-818 (2005).

Li et al., "Improved in vivo photoacoustic microscopy based on a virtual-detector concept," Optics Letters, 31, 474-476 (2006).

Liao et al., "Optoacoustic imaging with synthetic aperture focusing and cohehrence weighting," Optics Letters, 29, 2506-2508 (2004).

Machi et al., "Ultrasound-Guided Radiofrequency Thermal Ablation of Liver Tumors: Percutaneous, Laparoscopie, and Open Surgical Approaches", Journal of Gastrointestinal Surgery, vol. 5-5, pp. 477-489, Oct. 2001.

Maurer et al., "The Accuracy of Image Guided Neurosurgery Using Implantable Fiducial Markers", in Computer Assisted Radiology, Berlin, 1995, pp. 1197-1202.

Menack et al., "Staging of pancreatic and ampullary cancers for resectability using laparoscopy with laparoscopic ultrasound.", Surg Endosc, 15-10, pp. 1129-1134, Oct. 2001.

Myronenko et al., Point-Set Registration: Coherent Point Drift, IEEE Trans. on Pattern Analysis and Machine Intelligence 32(12), 2262-2275 (2010).

Arun et al., "Least-Squares Fitting of Two 3-I) Point Sets", *IEEE Transactions on Pattern Analysis and Machine Intelligence*, vol. 9-5, pp. 698-700, 1987.

Berber et al., "Resection versus Laparoscopic Radiofrequency Thermal Ablation of Solitary Colorectal Liver Metastasis", *Journal of Gastrointestinal Surgery*, vol. 12-11, pp. 1967-1972, Nov. 2008.

Besl et al., "A Method for Registration of 3-1) Shapes", *IEEE Transactions on Pattern Analysis and Machine Intelligence*, vol. 14-2, pp. pp239-pp256, 1992.

Bhayani et al., "Robotic assisted laparoscopic partial nephrectomy for suspected renal cell carcinoma: retrospective review of surgical outcomes of 35 cases", *BMC Surgery*, vol. 8-16, 2008.

Boctor et al., "A novel closed form solution for ultrasound calibration," in Int. Symp. Biomed. Image., pp. 527-530, IEEE, Arlington, (2004).

Boctor et al., "Three-dimensional ultrasound-guided robotic needle placement: an experimental evaluation", *Int J. Medical Robotics and Computer Assisted Surgery*, vol. 4-2, pp. 180-191, 2008.

Bopp et al., "An Orientation and Calibration Method for Non-Topographic Applications," Photogrametric Engineering and Remote Sensing, vol. 44-9, pp. 1191-1196, 1978.

Cannon et al., "Real-Time Three-Dimensional Ultrasound for Guiding Surgical Tasks", *Computer Aided Surgery*, vol. 8-2, pp. 82-90, 2003.

Cheng et al., Concurrent Photoacoustic Markers for Direct three-dimensional Ultrasound to Video Reg¬istration, Proc. SPIE BiOS, 89435J-89435J-9 (2014).

Cheng et al., Direct 3D ultrasound to video registration using photoacoustic effect, Med. Image. Comput. Comput. Assist. Interv. 2, 552559 (2012).

Cheng et al., Direct 3D ultrasound to video registration using photoacoustic markers, J. Biomed. Opt. 18(6), 066013 (2013).

Cheung et al., "Fused video and ultrasound images for minimally invasive partial nephrectomy: a phantom study," Med. Image. Comput. Comput. Assist. Interv. 13(3), 408-415 (2010).

Choti, "Surgical Management of Hepatocellulax Carcinoma: Resection and Ablation", Journal of Vascular and Interventional Radiology, vol. 13-9 Pt 2, pp. S197-S203, Sep. 2002.

Estepar et al., "Towards Real Time 2D to 3D Registration for Ultrasound-Guided Endoscopic and Laparoscopic Procedures", International Journal of Computer Assisted Radiology and Surgery, vol. 4-6, pp. 549.560, 2009.

Estepar et al., "Towards Scarless Surgery: An Endoseopic-Ultrasound Navigation; System for Transgastric Access Procedures", in Medical Image Computing and Computer Assisted Intervention, 2006. pp. 445-453.

Fischler et al.,"Random sample consensus: a paradigm for model fitting with applications to image analysis and automated cartography," Communications of the ACM. 24(6), 381-395 (1981).

Fleming et al., "Ultrasound elastography: enabling technology for image guided laparoscopic prostatectomy", in SPIE Medical Imaging 2009: Visualization, Image-guided Procedures and Modeling., Orlando, Florida, Jan. 2009, pp. 7261-7273, 10.1117/12.806507.

Foroughi et al., "Tracked Ultrasound Elastrography (TrUE)", *Medical Image Computing and Computer Assisted Intervention*, vol. 13-Pt 2, pp. 9-16, 2010.

Frazier et al., "Synthetic aperture techniques with a virtual source element," IEEE Trans. Ultrason., Ferroelec., Freq. Contr., 45, 196-207 (1998).

Guthart et al., "The Intuitive Telesurgery System: Overview and Application", in Proc. of the IEEE International Conference on Robotics and Automation (ICRA2000), 2000, pp. 618-621.

Hager et al., "The XVision System: A General-Purpose Substrate for Portable Real-Time Vision Applications", Computer Vision and Image Understanding, vol. 69-1, pp. 23-37, Jan. 1998.

Haralick, "2D-3D pose estimation", in Int Conf on Pattern Recognition (ICPR), Nov. 14-17, 1988, pp. 385-391.

Harrison et al., "Coregistered photoacoustic-ultrasound imaging applied to brachytherapy", J, Biomnedical Optics, vol. 16-8, Aug. 2011.

Harrison et al., "The applicability of ultrasound dynamic receive beamformers to photoacoustic imaging," IEEE Trans. Ultrason. Ferroelectr. Freq. Control, 58(10), 2259-2263 (2011).

Boctor et al., "Brachytherapy Seed Localization Using Combined Photoacoustic and Ultrasound Imaging (Abstract 7629-49)," in SPIE Medica/Imaging Conference San Diego, 2010, p. 203.

Choti M., et al., "Robotically Assisted Radiofrequency Ablation of Liver Cancer," IHPBA, 2002.

Esenaliev R.O., et al., "Sensitivity of Laser Opto-acoustic Imaging in Detection of Small Deeply Embedded Tumors," IEEE Journal on Selected Topics in Quantum Electronics, 1999, vol. 5(4), pp. 981-988.

International Search Report for International Application No. PCT/US2013/030273, dated Jul. 25, 2013, 3 pages.

Lee J.D., et al., "A Medical Augmented-reality System for Image-guided Surgery Using Marker-Added ICP," International Journal of Innovative Computing, Information and Control, 2011, vol. 7(11), pp. 6523-6539.

Maintzj., et al. , "A Survey of Medical Image Registration,"Medical image analysis , 1998, vol. 2(1), pp. 1-36.

Oberheide U., et al., "Optoacoustic Imaging for Optimization of Laser Cyclophotocoagulation," Journal of Biomedical Optics, 2003, vol. 8(2), pp. 281-287.

Pilatou, M. C., et al. , "Photoacoustic Monitoring of Changes in the Blood Circulation," Review of Scientific Instruments, 2003, vol. 74(1), pp. 384-386.

Ten Brinke G. A., et al., "Photoacoustic 3D visualization of tumor angiogenesis. Paper presented at the Progress in Biomedical Optics and Imaging," Proceedings of SPIE, 2008, vol. 6920, 7 pages.

Written Opinion for International Application No. PCT/US2013/030273, dated Jul. 25, 2013, 4 pages.

Xia T., et al. , "An Integrated System for Planning, Navigation and Robotic Assistance for Skull Base Surgery," International Journal of Medical Robotics and Computer Assisted Surgery, 2008, vol. 4(4), pp. 321-330.

\* cited by examiner

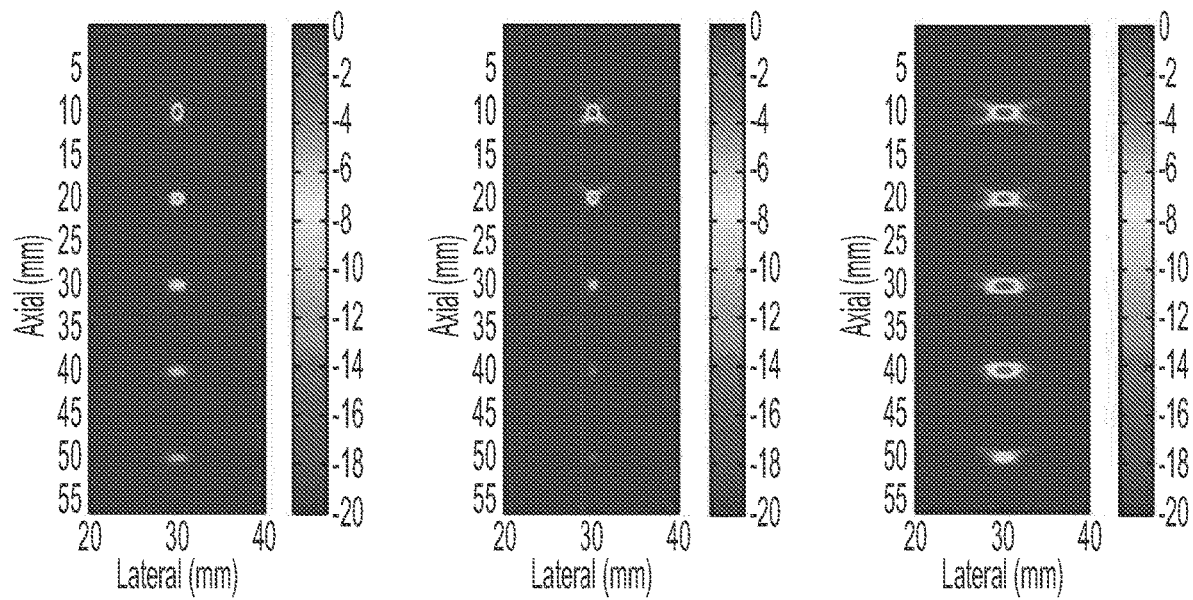
FIG. 9A  FIG. 9B  FIG. 9C
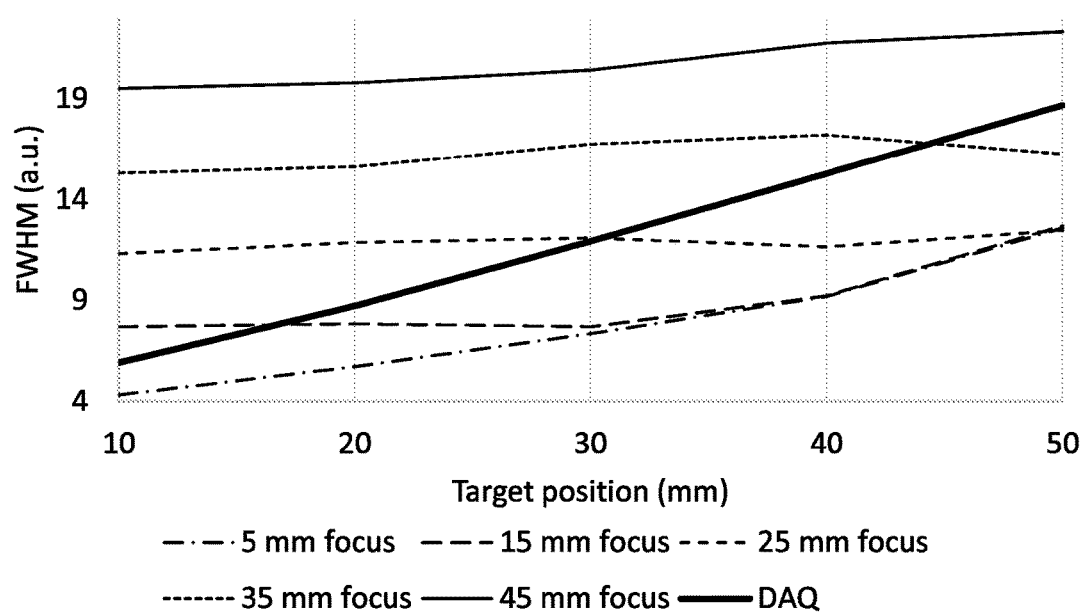
FIG. 10

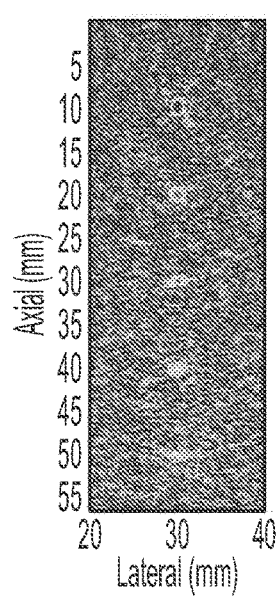 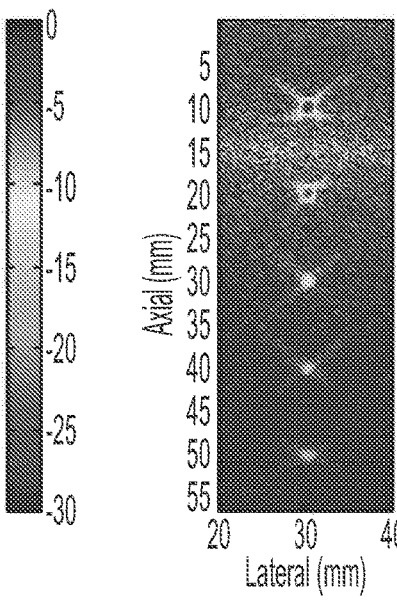 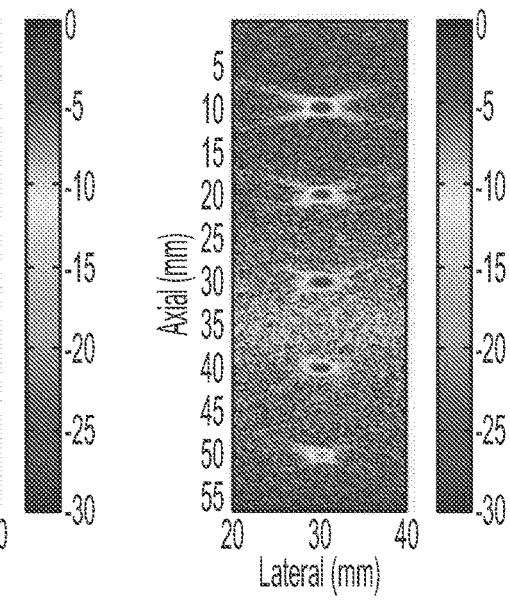
FIG. 11A   FIG. 11B   FIG. 11C
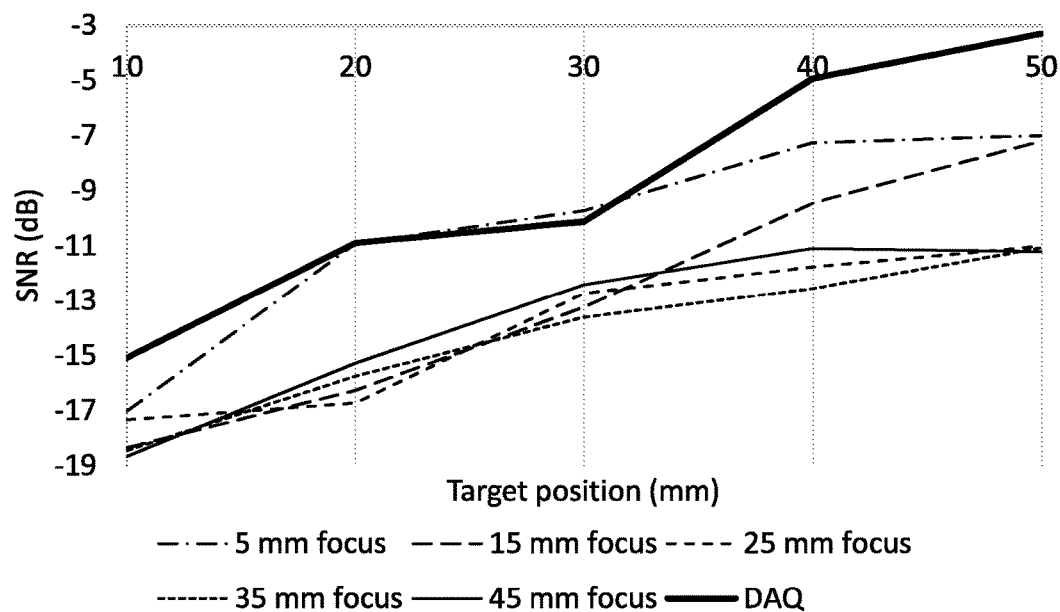
FIG. 12

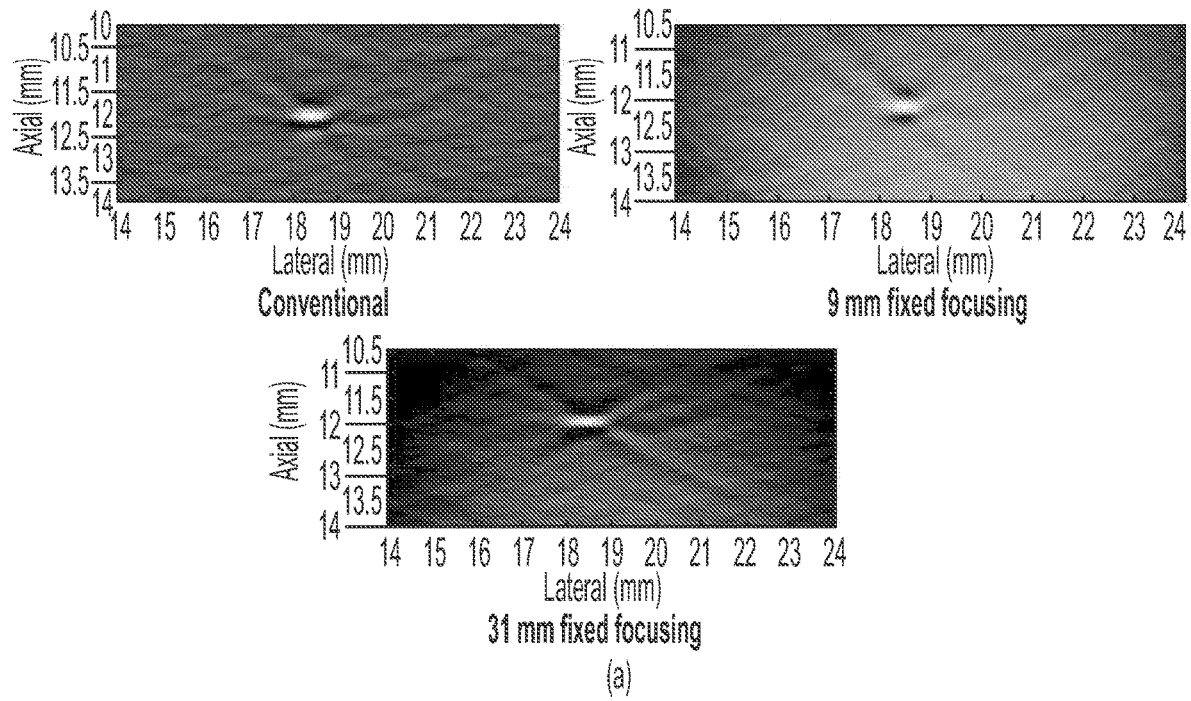
(a)
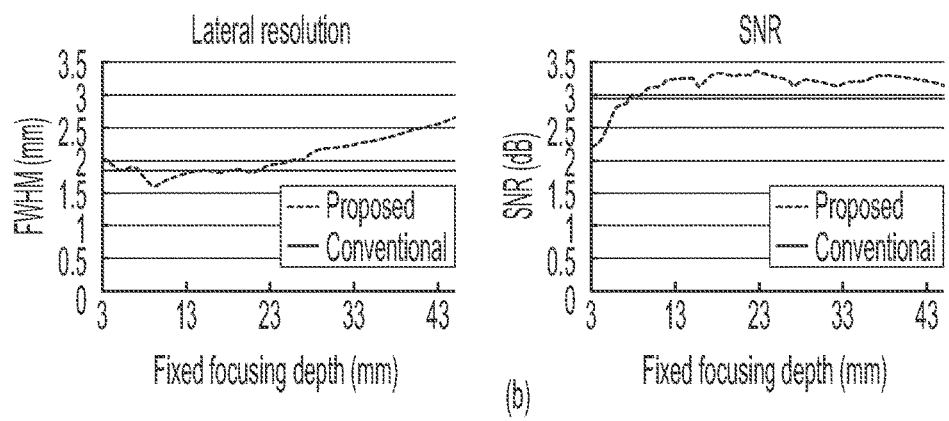
(b)
FIG. 36
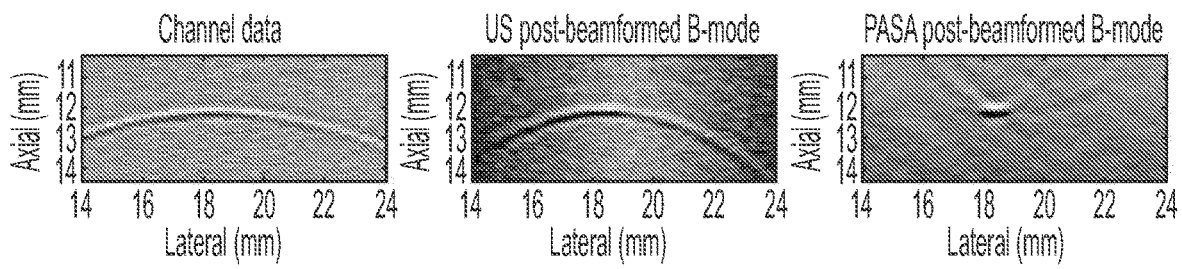
FIG. 37

$$w_i^2 = (e_{ix} - p_x)^2 + (e_{iy} - p_y)^2 + (e_{iz} - p_z)^2$$

$$e_i = [i * pitch, 0, 0]$$

$$w_i^2 = (e_{ix} - p_x)^2 + p_y^2 + p_z^2$$

| Precision | |
|---|---|
| RMSE | 0.8608 mm |
| Std Dev. | 0.8600 mm |

PHOTOACOUSTIC TRACKING AND REGISTRATION IN INTERVENTIONAL ULTRASOUND

This application claims priority to U.S. Provisional Application No. 62/113,918 filed Feb. 9, 2015, the entire content of which is hereby incorporated by reference.

This invention was made with Government support of Grant No. EB015638, awarded by the National Institute of Biomedical Imaging and Bioengineering—National Institutes of Health, and Grant No. IIS-1162095, awarded by the National Science Foundation. The U.S. Government has certain rights in this invention.

BACKGROUND

1. Technical Field

The field of the currently claimed embodiments of this invention relates to ultrasound systems and methods, and more particularly to ultrasound imaging systems and methods having real-time tracking and image registration.

2. Discussion of Related Art

Photoacoustic (PA) imaging is becoming an important tool for various clinical and pre-clinical applications. Acquiring pre-beamformed channel ultrasound data is essential to reconstruct PA images. Accessing these pre-beamformed channel data requires custom hardware to allow parallel beam-forming, and is available for only a few research ultrasound platforms or dedicated channel data extension device such as data acquisition (DAQ) system. These systems are generally expensive and extensive systems take time to transfer data from the ultrasound machine, so it becomes a limitation of real-time imaging. This fact can be an obstacle of smooth transaction for clinical application, and there is a strong demand to develop a beamforming algorithm utilizing post-beamformed radio frequency (RF) data. T. Harrison et al. has focused the same issue and their solution was to change the speed of sound value inside the clinical ultrasound system. A limitation of the approach is that not all clinical ultrasound systems provide accessibility to the speed of sound for beamforming. On the other hand, post-beamformed RF data is generally readily available in real-time and in several clinical and research ultrasound platforms.

SUMMARY

According to some embodiments of the invention, an ultrasound imaging system having real-time tracking and image registration includes a fiducial-marker system comprising an ultrasound transmitter, wherein the ultrasound transmitter is structured to provide a localized ultrasound pulse at an optically observable localized spot on a body of interest to provide a combined ultrasound and optical fiducial marker at the localized spot. The ultrasound imaging system further includes an optical imaging system structured to be arranged proximate the body of interest in view of the localized spot on the body of interest, and a two-dimensional ultrasound imaging system comprising an ultrasound probe structured to be acoustically coupled to the body of interest to receive the localized ultrasound pulse from the localized spot on the body of interest. The ultrasound imaging system further includes an optical image processing system configured to communicate with the optical imaging system to receive an optical image of at least a portion of the body of interest that includes the combined ultrasound and optical fiducial marker within the optical image, the optical image processing system being further configured to process the optical image to determine a spatial location of the combined ultrasound and optical fiducial marker. The ultrasound imaging system further includes an ultrasound image processing system configured to communicate with the two-dimensional ultrasound imaging system to receive a two-dimensional ultrasound image of at least a portion of the body of interest that includes the combined ultrasound and optical fiducial marker observed within the two-dimensional ultrasound image, the ultrasound image processing system being further configured to process the two-dimensional ultrasound image to determine a spatial location of the combined ultrasound and optical fiducial marker. The ultrasound imaging system further includes a registration system configured to communicate with the optical image processing system and the ultrasound image processing system to receive information concerning the spatial locations determined for the combined ultrasound and optical fiducial marker observed in the optical image and in the two-dimensional ultrasound image, the registration system being further configured to determine a coordinate transformation that registers the optical image with the two-dimensional ultrasound image based at least partially on the information concerning the spatial locations determined for the combined ultrasound and optical fiducial marker observed in the optical image and in the two-dimensional ultrasound image.

According to some embodiments of the invention, an ultrasound imaging system having real-time tracking and image registration, includes a fiducial-marker system comprising an ultrasound transmitter, wherein the ultrasound transmitter is structured to provide a localized ultrasound pulse at an optically observable localized spot on a body of interest to provide a combined ultrasound and optical fiducial marker at the localized spot. The ultrasound imaging system further includes an optical imaging system structured to be arranged proximate the body of interest in view of the localized spot on the body of interest. The ultrasound imaging system further includes an ultrasound imaging system comprising an ultrasound probe structured to be acoustically coupled to the body of interest to receive the localized ultrasound pulse from the localized spot on the body of interest. The ultrasound imaging system further includes an optical image processing system configured to communicate with the optical imaging system to receive an optical image of at least a portion of the body of interest that includes the combined ultrasound and optical fiducial marker observed within the optical image, the optical image processing system being further configured to process the optical image to determine a spatial location of the combined ultrasound and optical fiducial marker. The ultrasound imaging system further includes an ultrasound image processing system configured to communicate with the ultrasound imaging system to receive an ultrasound image of at least a portion of the body of interest that includes the combined ultrasound and optical fiducial marker within the ultrasound image, the ultrasound image processing system being further configured to process the ultrasound image to determine a spatial location of the combined ultrasound and optical fiducial marker. The ultrasound imaging system further includes a registration system configured to communicate with the optical image processing system and the ultrasound image processing system to receive information concerning the spatial locations determined for the combined ultrasound and optical fiducial marker observed in the optical image and in the ultrasound image, the registration system being further configured to determine a coordinate transformation that registers the optical image with the ultrasound image based at least partially on the information concerning the spatial locations determined for the combined ultrasound and optical fiducial marker observed in the optical image and in the ultrasound image. The ultrasound image processing system is configured to perform synthetic aperture imaging using post-beamformed RF data in an inverse beamforming calculation so as to be approximately equal to pre-beamformed RF data.

BRIEF DESCRIPTION OF THE DRAWINGS

Further objectives and advantages will become apparent from a consideration of the description, drawings, and examples.

FIG. 9A shows a simulated image of conventional PA beamforming;

FIG. 9B shows a simulated image of PA beamforming according to some embodiments of the invention with a fixed focus at 15 mm;

FIG. 9C shows a simulated image of PA beamforming according to some embodiments of the invention with a fixed focus at 35 mm;

FIG. 10 shows the full width at half maximum for each depth point with varying fixed focus depths;

FIG. 11A shows simulated images with noise for conventional PA beamforming;

FIG. 11B shows simulated images with noise for PA beamforming according to some embodiments of the invention with a fixed focus at 15 mm;

FIG. 11C shows simulated images with noise for PA beamforming according to some embodiments of the invention with a fixed focus at 35 mm;

FIG. 12 shows the signal-to-noise ratio (SNR) for each depth point with varying fixed focus depths;

FIG. 36 shows the SA re-beamforming results from ultrasound beamforming with a single focal point;

FIG. 37 shows the PASA beamforming results from dynamically focused ultrasound beamforming;

DETAILED DESCRIPTION

Figure 1:
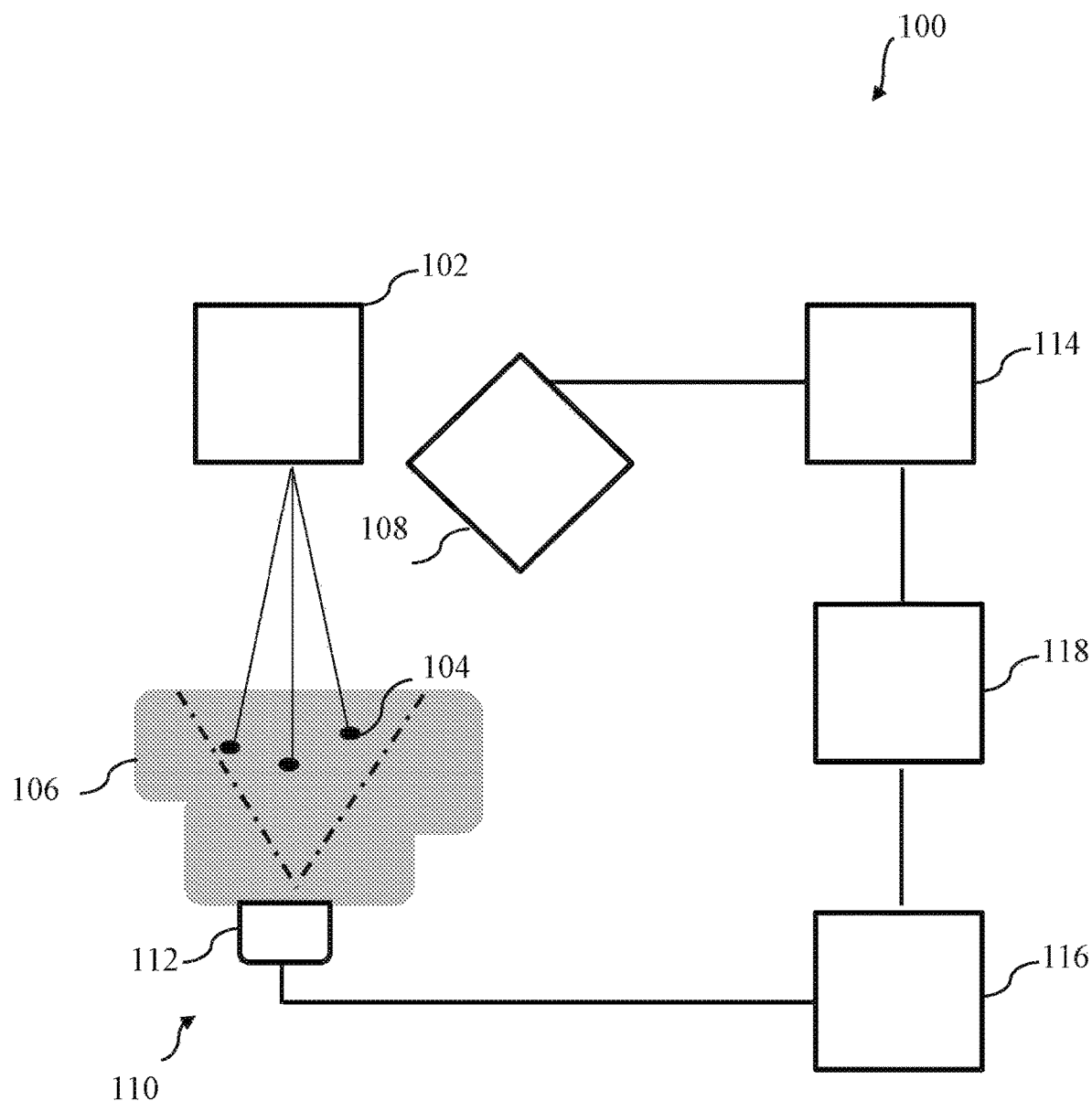
FIG. 1 is a schematic illustration of an ultrasound imaging system having real-time tracking and image registration according to an embodiment of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The terms "light" and "optical" are intended to have a broad meaning. They can include, but are not limited to, the visible regions of the electromagnetic spectrum. They can include nonvisible regions of the electromagnetic spectrum such as infrared and ultraviolet light, and even x-ray and microwave regions. As long as the electromagnetic radiation can deposit a localized spot of energy that generates ultrasound, and the spot can be detected along with a corresponding image, it can be included in some embodiments.

The term "photoacoustic" is intended to have a broad definition which can be photons at any energy suitable for the particular application that deposit energy that generates an acoustic signal in a body of interest. This is intended to be sufficiently broad to include photons of microwave energy. The term "thermoacoustic" effect is often used with reference to microwave energies. The term photoacoustic as used herein is intended to include thermoacoustic in the broad definition.

The term "body" refers generally to a mass, and not specifically to a human or animal body. In some applications, the body of interest can be a human or animal organ, or a portion thereof.

The term "spot" is intended to have a broad meaning. It can be point-like or a small circular or oval shape. However, it can also can be a pattern, such as, but not limited to an x shape, a v shape, a Z shape, and N shape, etc.

The term "substantially localized spot" means a spot of a size and of defined boundaries sufficient for the particular application. (In the case of a pattern, the localization can be with respect to one sub-feature of the pattern.) For example, most surgeries may require spot sizes from 0.5 to 2 mm. However, some surgeries may require more precision than other surgeries and the imaging geometries may vary. Consequently, the general concepts of the current invention are not limited to particular sizes and location precision of the spots.

The term "interstitial" means to be inserted into tissue, such as, but not limited to, a needle inserted into tissue with the inserted tip being surrounded by the tissue.

The term "real-time" is intended to mean that the images can be provided to the user during use of the system. In other words, any noticeable time delay between detection and image display to a user is sufficiently short for the particular application at hand. In some cases, the time delay can be so short as to be unnoticeable by a user.

We use "3DPA" to mean 3D photoacoustic images and "3DUS" to mean conventional 3D ultrasound images or the overall system. The same transducer can be used for both and both have the same coordinate system, and we can use "3DUS coordinates" and "3DPA coordinates" interchangeably.

The control protocol and algorithms described herein may be implemented by a processor. The processor may be referred to as signal processor, or may include an optical detection apparatus, and may be referred to as an optical detection and processing system. The processor can be a dedicated "hard-wired" device, or it can be a programmable device. For example, it can be, but is not limited to, a personal computer, a work station, or any other suitable electronic device for the particular application. In some embodiments, it can be integrated into a unit or it can be attachable, remote, and/or distributed.

This application is related to International Application No. PCT/US2013/030273, which is incorporated by reference herein in its entirety.

An ultrasound imaging system having real-time tracking and image registration according to some embodiments of the invention is shown in FIG. 1. According to some embodiments of the invention, the ultrasound imaging system 100 includes a fiducial-marker system 102 comprising an ultrasound transmitter, wherein the ultrasound transmitter is structured to provide a localized ultrasound pulse at an optically observable localized spot 104 on a body of interest 106 to provide a combined ultrasound and optical fiducial marker at the localized spot 104. The ultrasound imaging system 100 further includes an optical imaging system 108 structured to be arranged proximate the body of interest 106 in view of the localized spot 104 on the body of interest 106. The ultrasound imaging system 100 further includes a two-dimensional ultrasound imaging system 110 that includes an ultrasound probe 112 structured to be acoustically coupled to the body of interest 106 to receive the localized ultrasound pulse from the localized spot 104 on the body of interest 106. The ultrasound imaging system 100 further includes an optical image processing system 114 configured to communicate with the optical imaging system 108 to receive an optical image of at least a portion of the body of interest 106 that includes the combined ultrasound and optical fiducial marker within the optical image, the optical image processing system 114 being further configured to process the optical image to determine a spatial location of the combined ultrasound and optical fiducial marker. The ultrasound imaging system 100 further includes an ultrasound image processing system 116 configured to communicate with the two-dimensional ultrasound imaging system 110 to receive a two-dimensional ultrasound image of at least a portion of the body of interest 106 that includes the combined ultrasound and optical fiducial marker within the two-dimensional ultrasound image, the ultrasound image processing system 116 being further configured to process the two-dimensional ultrasound image to determine a spatial location of the combined ultrasound and optical fiducial marker. The ultrasound imaging system 100 further includes a registration system 118 configured to communicate with the optical image processing system 114 and the ultrasound image processing system 116 to receive information concerning the spatial locations determined for the combined ultrasound and optical fiducial marker in the optical image and in the two-dimensional ultrasound image, the registration system 118 being further configured to determine a coordinate transformation that registers the optical image with the two-dimensional ultrasound image based at least partially on the information concerning the spatial locations determined for the combined ultrasound and optical fiducial marker in the optical image and in the two-dimensional ultrasound image.

According to some embodiments of the invention, the optical image processing system 114, ultrasound image processing system 116, and registration system 118 can be implemented in software and/or hardware. For example, they could all be implemented in software on the same computer and/or network of computers in some embodiments. In some embodiments, one or more of the optical image processing system 114, ultrasound image processing system 116, and registration system 118 can be implemented in separate hardware components, for example, making use of ASICs (application-specific integrated circuit), FPGAs (field programmable gate array) and/or other dedicated circuitry.

According to some embodiments of the invention, the fiducial-marker system 102 can be one or more photoacoustic transmitters and/or localized transducers such as a transducer at the tip of a surgical instrument. When photoacoustic transmitters are used, fiducial-marker system 102 can also include a photoacoustic material acoustically coupled to the body of interest 106. The optical imaging system 108 can be a single camera with additional information provided, or stereo cameras. The optical imaging system 108 can be at a fixed position in the room frame, or attached to the ultrasound probe, for example.

According to some embodiments, the ultrasound transmitter is a photoacoustic transmitter comprising a pulsed light source configured to provide said combined ultrasound and optical fiducial marker at said localized spot. According to some embodiments, the pulsed light source is a pulsed laser diode, a high power LED (light emitting diode), a Xeon flash lamp, a microwave energy source, or a Q-switch laser. Either photonic or electromagnetic energy can be utilized to create the thermoacoustic effect.

An ultrasound imaging system having real-time tracking and image registration according to some further embodiments of the invention is also described in connection with FIG. 1. This embodiment can use two-dimensional or three-dimensional ultrasound imaging. According to some embodiments of the invention, the ultrasound imaging system 100 includes a fiducial-marker system 102 comprising an ultrasound transmitter, wherein the ultrasound transmitter is structured to provide a localized ultrasound pulse at an optically observable localized spot 104 on a body of interest 106 to provide a combined ultrasound and optical fiducial marker at the localized spot 104. The ultrasound imaging system 100 further includes an optical imaging system 108 structured to be arranged proximate the body of interest 106 in view of the localized spot 104 on the body of interest 106. The ultrasound imaging system 100 further includes an ultrasound imaging system 110 that includes an ultrasound probe 112 structured to be acoustically coupled to the body of interest 106 to receive the localized ultrasound pulse from the localized spot 104 on the body of interest 106. The ultrasound imaging system 100 further includes an optical image processing system 114 configured to communicate with the optical imaging system 108 to receive an optical image of at least a portion of the body of interest 106 that includes the combined ultrasound and optical fiducial marker within the optical image, the optical image processing system 114 being further configured to process the optical image to determine a spatial location of the combined ultrasound and optical fiducial marker. The ultrasound imaging system 100 further includes an ultrasound image processing system 116 configured to communicate with the ultrasound imaging system 110 to receive an ultrasound image of at least a portion of the body of interest 106 that includes the combined ultrasound and optical fiducial marker within the ultrasound image, the ultrasound image processing system 116 being further configured to process the ultrasound image to determine a spatial location of the combined ultrasound and optical fiducial marker. The ultrasound image processing system 116 is configured to perform synthetic aperture imaging using post-beamformed RF data in an inverse beamforming calculation so as to be approximately equal to pre-beamformed RF data.

The ultrasound imaging system 100 further includes a registration system 118 configured to communicate with the optical image processing system 114 and the ultrasound image processing system 116 to receive information concerning the spatial locations determined for the combined ultrasound and optical fiducial marker in the optical image and in the ultrasound image, the registration system 118 being further configured to determine a coordinate transformation that registers the optical image with the ultrasound image based at least partially on the information concerning the spatial locations determined for the combined ultrasound and optical fiducial marker in the optical image and in the ultrasound image.

According to some embodiments of the invention, the optical image processing system 114, ultrasound image processing system 116, and registration system 118 can be implemented in software and/or hardware. For example, they could all be implemented in software on the same computer and/or network of computers in some embodiments. In some embodiments, one or more of the optical image processing system 114, ultrasound image processing system 116, and registration system 118 can be implemented in separate hardware components, for example, making use of ASICs, FPGAs and/or other dedicated circuitry.

According to some embodiments of the invention, the fiducial-marker system 102 can be one or more photoacoustic transmitters and/or localized transducers such as a transducer at the tip of a surgical instrument. When photoacoustic transmitters are used, fiducial-marker system 102 can also include a photoacoustic material acoustically coupled to the body of interest 106. The optical imaging system 108 can be a single camera with additional information provided, or stereo cameras. The optical imaging system 108 can be at a fixed position in the room frame, or attached to the ultrasound probe, for example.

The following examples describe some embodiments in more detail. The broad concepts of the current invention are not intended to be limited to the particular examples. Further, concepts from each example are not limited to that example, but may be combined with other embodiments of the system.

EXAMPLES

Example 1

Direct Ultrasound to Video Registration using Photoacoustic Markers from a Single Image Pose Modern surgical procedures including open, laparoscopic, and robotic surgeries are often aided by interventional guidance systems. [1] There is a need for these systems as surgical environments are constantly changing and tumors may only be visible under medical imaging guidance, or move in and out of the camera's field of view. Interventional guidance systems provide a fusion of video and other imaging modalities, such as interoperative ultrasound (US), to alleviate some of these concerns. This video and medical imaging fusion can support surgeons in finding and tracking tumors or other objects of interest. A registration process between surgical tools and devices, such as stereoscopic endoscopes and US transducers, is necessary to enable these guidance systems.

This example focuses on the registration between stereoscopic video and US imaging. Many surgeries require real-time US imaging including liver resections, partial nephrectomies, and prostatectomies. Real-time fusion of US and video, is crucial to the success of these operations and registration is a crucial component to enable real-time fusion. The registration between US images and video is an active area of research and significant challenges remain. Typically, electromagnetic (EM) or optical navigational trackers [2, 3] are used to provide the real-time pose, position and orientation, of tools such as US transducers. This approach is subject to serious limitations and prone to error buildup from multiple concatenated tracking and calibration errors.

The two main types of surgical navigation and tracking systems are based on EM [3, 4] or optical trackers. Each of these trackers have their respective advantages and disadvantages. The main advantage for EM-based surgical navigation systems is that a clear line of sight to the EM sensor is unnecessary. This reduces the surgical field setup constraints, however, other drawbacks must be considered and accounted for. Firstly, EM tracking systems require wired EM sensors to be placed on the tracked tool. This is disadvantageous as it clutters the surgical environment and modifies the tools, possibly decreasing the surgeon's comfort while potentially increasing handling and sterilizing costs. Secondly, EM tracking systems require a large and intrusive EM field generator to be placed in close proximity to the tracked EM sensors. The space around the operating table is limited, thus the surgeon must consider if this the most effective use of a limited resource. Finally, EM-based systems suffer from magnetic field distortions when metallic objects are placed within its field. This serves as one of the main limitations as it degrades the system's accuracy, thereby decreasing the value that surgeons can derive from the system.

Optical tacking systems do not suffer from magnetic field distortion and generally do not require wired sensors. While, optical tracking systems can detect optical markers with sub-millimeter accuracy, [5, 6] line of sight is a requirement that must be satisfied. This places a restrictive constraint on the number and placement of other tools in the surgical field, making such systems often impractical for laparoscopic procedures. These concerns can be somewhat addressed by placing the optical markers outside the body, but the tracking accuracy of long and flexible tools will degrade as their tips are now much farther away from the optical markers and prone to deflection or bending errors.

One drawback that affects both typical EM and optical-based navigation systems is that the transformation registering surgical tools with the navigation system is acquired indirectly. This means that the coordinate systems of the surgical tool and the navigation system are linked by a chain of transformations that must be computed. An example of an indirect transformation is the one necessary to enable interventional US guidance. The desired transformation between the two coordinate systems is composed of the pose acquired from the tracking system and the US calibration transformation between the sensor or marker and the US image plane. By composing a chain of transformations, their respective errors are magnified. Thus, it is beneficial to have a method which can acquire the desired transformation directly without composing a series of transformations.

Another drawback of these navigation systems is specific to interventional US guidance systems. As was previously mentioned, US calibration is necessary to enable these systems. It is an active topic of research and many authors have presented methods to achieve better accuracy and lower errors. [7, 8] Their results have shown that the overall registration error is dominated by the calibration process as its error is much larger than the error of the tracking systems. Overall registration errors of approximately 1.7 to 3 mm for artificial phantoms and 3 to 5 mm for tissue have been shown. [3, 4, 9, 10]

Vyas et al. [11] and Cheng et al. [12-14] demonstrated a direct three-dimensional US to video registration method using photoacoustic (PA) markers. This novel method used PA markers generated on an air-tissue interface, visible to both a stereocamera (SC) system and US, as fiducials to directly acquire the registration between video and three-dimensional US. Previous work [15, 16] showed that a pulsed laser source is capable of generating a PA signal in tissue. The resulting acoustic wave from the PA signal can be detected by a conventional US transducer. [17, 18] The laser source is also visible to the SC system, so the PA markers are also visible. This enables PA markers to be used as fiducials as the same point can be represented in both the SC system's coordinate system and the US image's coordinate system.

This method addresses the drawbacks present in EM and optical-based navigation systems. Firstly, this method does not require wired sensors so no modifications are made to the surgeon's tools. This allows the tools to maintain their present handling and sterilizing procedures. Since there are no attached wired sensors, US calibration is also unnecessary with this method. This is a major advantage as the registration error can be much lower by avoiding the US calibration process. [12, 13] While this method requires line of sight between the PA markers and the SC system, this requirement is less stringent than the requirement for optical trackers. The PA markers are projected onto the surface of a region of interest, so it will naturally be within the SC system's field of view.

Figure 2:
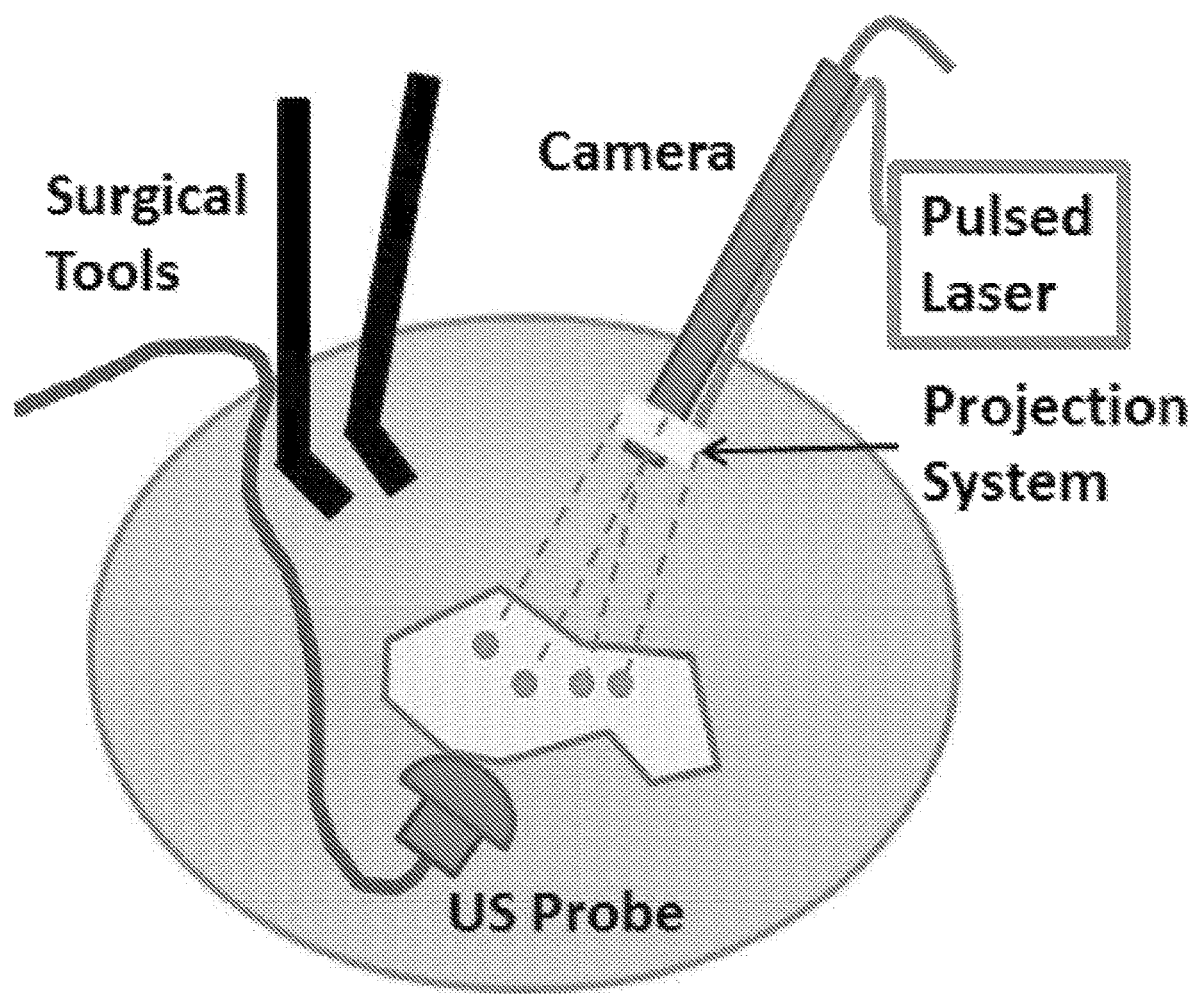
FIG. 2 illustrates a clinical scenario using photoacoustic (PA) markers to acquire this video to ultrasound (US) registration with a two-dimensional curvilinear transducer.

This work extends the earlier work of Vyas et al. [11] and Cheng et al., [12-14] and serves as another step towards realizing a practical clinical system shown in FIG. 2. The main contribution of this work is to recover the video to ultrasound registration with two-dimensional images from a single pose. Naturally, this means that this method can be extended to two-dimensional US transducers and is no longer limited to three-dimensional US probes. There are both advantages and disadvantages of using two-dimensional US transducers versus three-dimensional US transducers. Three-dimensional transducers are capable of providing an entire volume at the expense of acquisition time. On the other hand, two-dimensional transducers are much faster, but the registration between two-dimensional US images and three-dimensional video is considerably more difficult. Using a two-dimensional transducer will also allow us to relax the assumption that the surgical environment remains static during data acquisition as a volume is no longer necessary.

In this example, we show that it is possible to recover some out-of-plane information from a single two-dimensional curvilinear US image when using PA markers. We detail the ideas and algorithms that facilitate the process of registering two-dimensional US images with three-dimensional video. Preliminary results using a synthetic phantom with excellent light absorption characteristics will also be shown.

Algorithms

There are two main components that allow us to recover the registration between video and ultrasound with a single US image. First of all, a wavefront segmentation algorithm is necessary as the wavefront allows us to recover some out-of-plane information. This wavefront represents the time of flight (ToF) readings from the active PA marker to each of the US transducer elements. Second of all, to be able to register PA markers between two-dimensional US and video, we show how the ToF readings can be used to recover out-of-plane information. Before we present these two components, we will discuss the model that we use to derive the subsequent algorithms.

Wavefront Modeling

Figure 3:
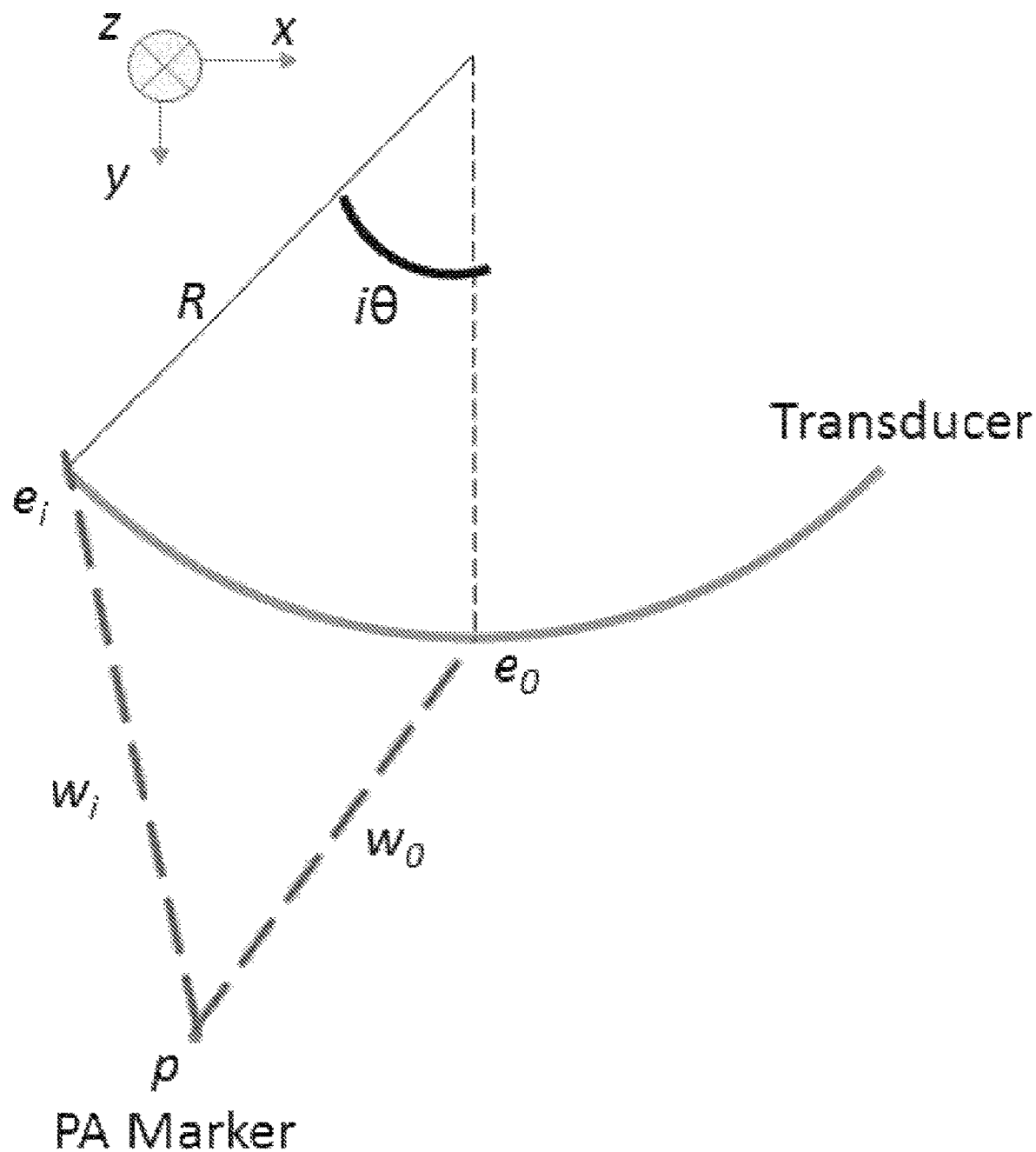
FIG. 3 shows a wavefront model.

As we previously mentioned, the wavefront from a single PA marker can represent the ToF between the PA marker and each transducer element. As shown in FIG. 3, we have a set of transducer elements from a curvilinear transducer, $e_i$, and a single PA marker, p. R represents the transducer curvature and $\theta$ represents the element pitch. The set of distances between each element $e_i$ and p is represented by $w_i$. As we can see from this model, we are making the assumption that each of the transducer elements and the PA marker itself are acting as point receivers and a point source respectively.

Wavefront Segmentation

Figure 4:
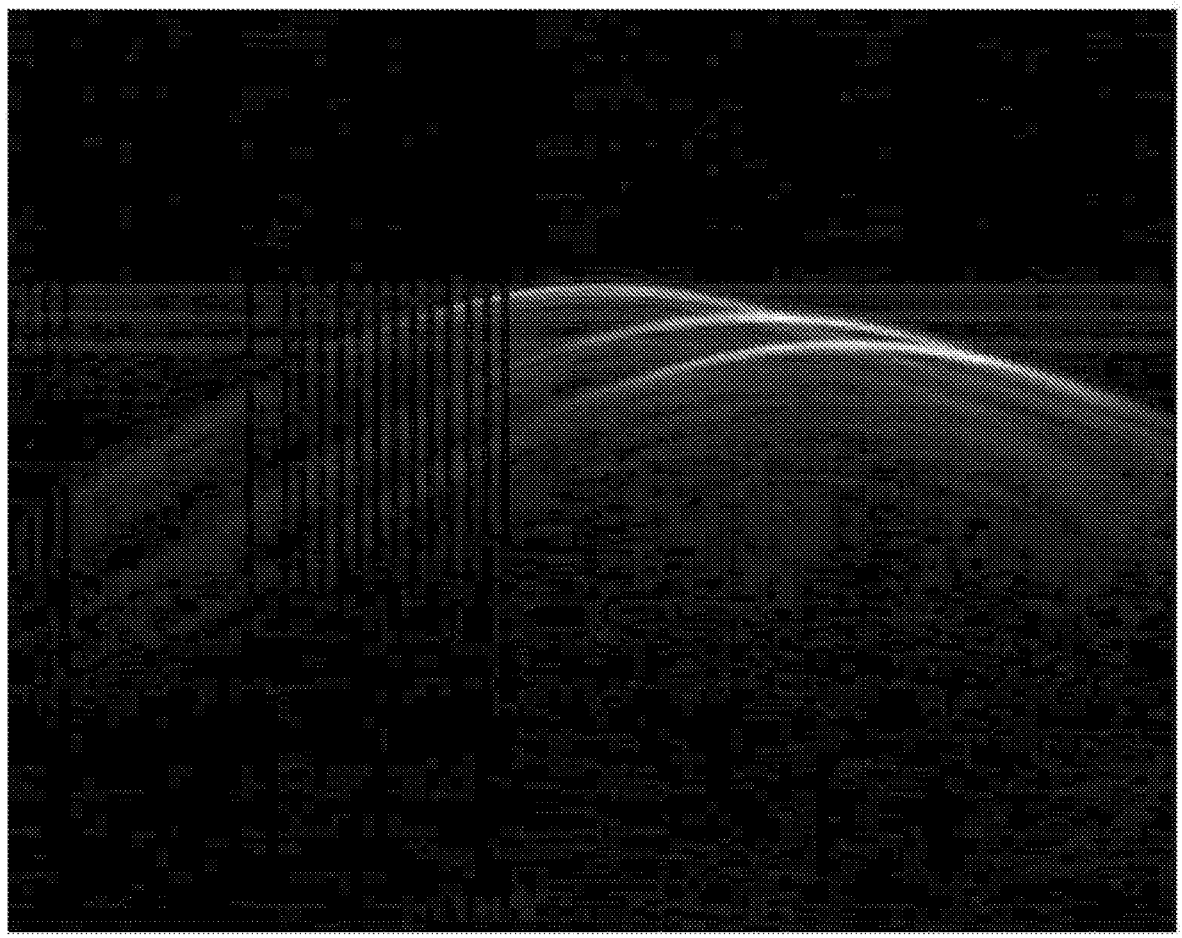
FIG. 4 shows a sample pre-beamformed PA image with PA markers present without segmentation.
Figure 5:
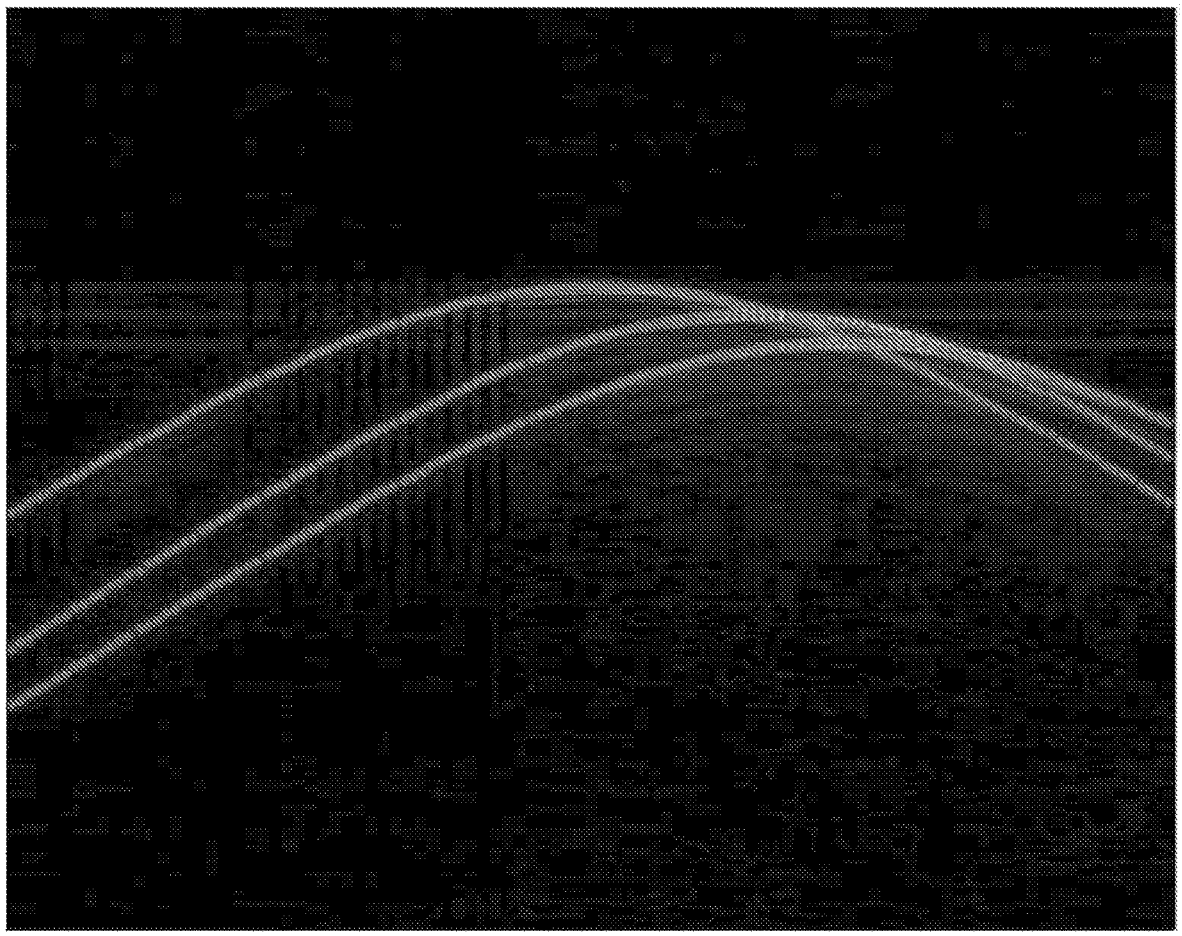
FIG. 5 shows a sample pre-beamformed PA image with PA markers present with segmentation.

Segmentation of a point source in a PA image is generally much easier than in an US B-mode image. In most cases, an algorithm utilizing intensity thresholds is sufficient in segmenting the desired wavefront. One can then look at the radio-frequency (RF) signal for each element and pick the earliest signal as the wavefront's ToF for that particular element. Naturally, this will only work when there is a single wavefront present in the PA image. When there are wavefronts from multiple PA markers present in a single PA image as seen in FIGS. 4 and 5, we can no longer just pick the earliest signal as the wavefront's ToF.

$$w_{ij}^2 = a_j + \cos(i\theta)b_j + \sin(i\theta)c_j \quad (1.1)$$

Based on the wavefront model shown in FIG. 3, each wavefront from a unique PA marker can be represented by equation (1.1). There is a slight change of notation where $w_{ij}$ is the axial position of the wavefront j for element i. In addition, $a_j$, $b_j$, and $c_j$ are constants unique to PA marker j. From the initial intensity thresholding algorithm, we acquire a set of $w_i$ with unknown correspondence to a set of PA markers. This means that there may be multiple $w_i$ values for any particular element i. We combine equation (1.1) with a RANSAC (random sample consensus) approach [19] to separate these $w_i$ into $w_{ij}$. A set of $w_i$ for different i's are selected randomly. We then solve for a, b, and c, which will uniquely define the equation for a wavefront in the PA image. We then find all $w_i$ that satisfy this wavefront and determine if there are enough votes from $w_i$ to state that this wavefront corresponds with a unique PA marker j. If so, this set of $w_i$ is removed from the complete set and denoted as $w_{ij}$. The derivation for equation (1.1) will be presented in the next section.

Out-of-Plane Position Recovery

The segmented wavefronts can be used to recover some information about the PA marker's position relative to the US transducer. As was previously mentioned, each $w_i$ represents the ToF and corresponding distance between element i and the PA marker's three-dimensional position. If we consider the ideal case, where the transducer elements are ideal point sources, we can represent this relationship with equation (1.2) where $e_i$ is the position of element i and p is the position of the PA marker. Since we are using curvilinear transducers, $e_i$ can be described by equation (1.3) where R is the radius of the curvilinear transducer. Substituting $e_i$ into equation (1.2) will result in a form that satisfies equation (1.1). Theoretically, $p_i$ can be uniquely solved up to sign in this situation given a minimum of three valid $w_i$. There are several approaches to solve this equation. One approach is to directly solve equation (1.2) with a non-linear optimization approach. Another approach is to use the unique constants a, b, and c, from equation (1.1) and solve for the p terms within those constants. The unknown sign means that the point can either be in front or behind of the image plane.

$$w_i^2 = (e_{ix} - p_x)^2 + (e_{iy} - p_y)^2 + (e_{iz} - p_z)^2 \quad (1.2)$$

$$e_i = [R \sin(i\theta), R \cos(i\theta), 0] \quad (1.3)$$

Methods

In these experiments, we used a Q-switched neodymium-doped yttrium aluminum garnet (Nd:YAG) Brilliant (Quantel Laser, France) laser to generate the PA marker. We used a wavelength of 1064 nm and an energy density between 5 to 10 mJ/cm$^2$ on the synthetic phantom. These values are below the maximum permissible exposure (MPE), 100 mJ/cm$^2$, as calculated from the IEC 60825-1 laser safety standard [20] based on a 0.25 s exposure time, a 4 ns pulse width, and a frequency of 10 Hz. We used a Sonix Touch US system and a 4DC3-7/40 US transducer developed by Ultrasonix Medical Corporation (Richmond, Canada) to collect two-dimensional images. This three-dimensional US transducer consists of a curvilinear US array, with a motor actuated to move angularly around an internal pivot point. For the purposes of this work, we used it as a two-dimensional transducer and did not actuate the motor. It has a bandwidth of 3 to 7 MHz and the transducer radius is approximately 40 mm. The Sonix DAQ device, developed by the University of Hong Kong and Ultrasonix, and the MUSiiC toolkit [21] are used to acquire prebeamformed radio-frequency (RF) data from the US machine. The SC setup consists of two CMLN-13S2C cameras (Point Grey Research, Richmond, Canada) to capture images at 18 Hz. The camera calibration process using the Camera Calibration Toolbox for MATLAB® [22] generates a calibration file for the SC setup, allowing us to perform three-dimensional triangulation. These experiments were performed on a synthetic black plastisol phantom.

Figure 6:
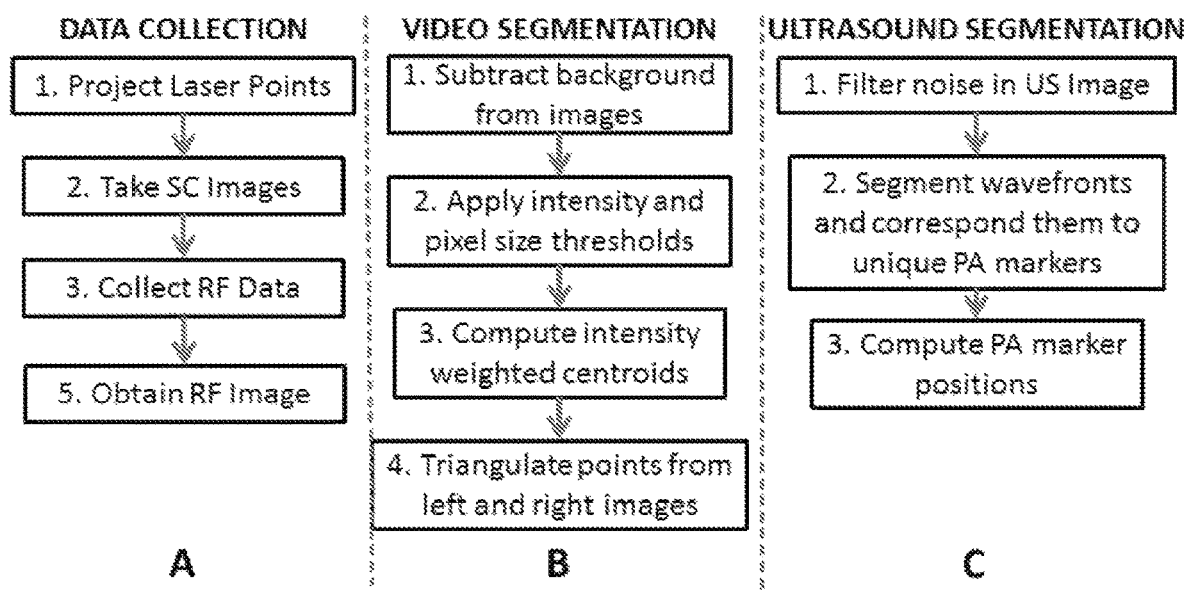
FIG. 6 illustrates workflows for the A) Data Collection, B) Video Segmentation, and C) Ultrasound Segmentation.

The experiments can be separated into three phases: data collection, data processing, and registration. The data collection phase consists of collecting a pair of SC images and a two-dimensional prebeamformed PA image. The data processing phase will then process the PA image using the aforementioned wavefront segmentation and out-of-plane position recovery algorithms to generate two $p_i$ for each PA marker. The PA markers are segmented from the SC images using the same methods described in previous work. [12-14] These two sets of information are registered together in the registration phase to finally output the transformation registering the SC frame to the US frame. The new workflows can be seen in FIG. 6.

The key difference in these phases between this work and previous work is the registration phase. Since each PA marker in the US coordinate system can only be solved up to a sign, there are now a pair of possible points for each PA marker. We use all of these points in the US coordinate system and register them with the PA markers in the SC coordinate system using the coherent point drift algorithm. This algorithm is ideal for these cases where point correspondence is unknown and the number of points in each dataset are different. The one thing that must be noted is that we must check that the resulting transformation is in the special Euclidian group SE(3) and is not a reflection.

Results

The registration results of our experiments on the synthetic phantom are validated using the target registration error (TRE) metric defined in equation (1.4). Fscus is the transformation between the SC frame and the US frame computed with all of the SC and US points except for one. The TRE is the difference between the actual US test point and the transformed SC test point in the US frame. N is the number of points in the experiment and N-1 points are used to compute FSCUS. This computation is repeated with each of the N points, six in this case, as test points. The resulting TRE for this experiment was 2.47 mm and the standard deviation was 1.29 mm, which is comparable to current available systems.

$$\vec{TRE} = F_{SC\_US} * \vec{SC}_{test} - \vec{US}_{test} \qquad (1.4)$$

Discussion

The experimental results show that this three-dimensional US to video registration method using PA markers from a single image has comparable accuracy to state of the art surgical navigation systems. While there is some concern that they are worse than the results shown previously, [12-14] it is also expected as there is much less information present in a single PA image as opposed to an entire volume. Besides this reason, there may be several explanations for this occurrence. Errors in both the wavefront segmentation and out-of-plane position recovery algorithms will naturally propagate to the PA marker positions. Since the position is recovered based on ToF, the segmented wavefront is ideally the earliest arrival of acoustic pressure. However, what ends up being detected may be the earliest arrival of acoustic pressure that is greater than noise. Also, some speed of sound must be used to convert the ToF for out-of-plane position recovery. The largest source of error likely stems from the initial assumptions that were made. In this work, we assume that the US transducer consists of ideal point source receivers. Future work is currently aimed at devising a more suitable model without making such strong assumptions.

There are also some considerations in moving this system to in vivo experiments. One advantage of using two-dimensional US images versus a three-dimensional US volume is that the data-acquisition time is shortened drastically. Previously, the assumption that the environment is static while the volume is being collected had to be made. However, with a registration method that uses a single US image, we no longer have to make this assumption. This greatly decreases the barrier between this method and in vivo experiments.

Conclusion

We demonstrated an extension to an innovative three-dimensional US-to-video direct registration medical tracking technology based on PA markers using US images from a single pose. We demonstrated the feasibility of this method on a synthetic phantom. We showed that this method has comparable accuracy with state of the art surgical navigation systems.

REFERENCES—EXAMPLE 1

[1] Y. Wang, S. Butner, and A. Darzi, "The developing market for medical robotics," Proc. IEEE 94(9), 1763¬1771 (2006).

[2] R. Taylor et al., Computer Integrated Surgery, MIT Press, Cambridge, Massachusetts (1996).

[3] P. J. Stolka et al., "A 3D-elastography-guided system for laparoscopic partial nephrectomies," Proc. SPIE 7625, 762511 (2010).

[4] C. L. Cheung et al., "Fused video and ultrasound images for minimally invasive partial nephrectomy: a phantom study," Med. Image. Comput. Comput. Assist. Interv. 13(3), 408-415 (2010).

[5] N. Navab, M. Mitschke, and O. Schutz, "Camera-augmented mobile C-arm (CAMC) application: 3D recon¬struction using low cost mobile C-arm," Med. Image. Comput. Comput. Assist. Interv. 1679, 688-697 (1999).

[6] A. Wiles, D. Thompson, and D. Frantz, "Accuracy assessment and interpretation for optical tracking sys¬tems," Proc. SPIE 5367, 421-432 (2004).

[7] E. Boctor et al., "A novel closed form solution for ultrasound calibration," in Int. Symp. Biomed. Image., pp. 527-530, IEEE, Arlington, (2004).

[8] T. Poon and R. Rohling, "Comparison of calibration methods for spatial tracking of a 3-D ultrasound prove," Ultrasound Med. Biol. 31(8), 1095-1108 (2005).

[9] J. Leven et al., "DaVinci canvas: a telerobotic surgical system with integrated, robot-assisted, laparoscopic ultrasound capability," Med. Image. Comput. Comput. Assist. Interv. 8(1), 811-818 (2005).

[10] M. C. Yip et al., "3D ultrasound to stereoscopic camera registration through an air-tissue boundary," Med. Image. Comput. Comput. Assist. Interv. 13(2), 626-634 (2010).

[11] S. Vyas et al., "Interoperative ultrasound to stereo-camera registration using interventional photoacoustic imaging," Proc. SPIE 8316, 83160S (2012).

[12] A. Cheng et al., Direct 3D ultrasound to video registration using photoacoustic effect, Med. Image. Comput. Comput. Assist. Interv. 2, 552559 (2012).

[13] A. Cheng et al., Direct 3D ultrasound to video registration using photoacoustic markers, J. Biomed. Opt. 18(6), 066013 (2013).

[14] A. Cheng et al., Concurrent Photoacoustic Markers for Direct three-dimensional Ultrasound to Video Reg¬istration, Proc. SPIE BiOS, 89435J-89435J-9 (2014).

[15] R. Kolkman, W. Steenbergen, and T. van Leeuwen, "In vivo photoacoustic imaging of blood vessels with a pulsed laser diode," Laser. Med. Sci. 21(3), 134-139 (2006).

[16] N. Kuo et al., "Photoacoustic imaging of prostate brachtherapy seeds in ex vivo prostate," Proc. SPIE 7964, 796409 (2011).

[17] M. Xu and L. Wang, "Photoacoustic imaging in biomedicine," Rev. Sci. Instrum. 77, 041101 (2006).

[18] C. Hoelen et al., "Three-dimensional photoacoustic imaging of blood vessels in tissue," Opt. Lett. 23(8), 648-650 (1998).

[19] M. A. Fischler and R. C. Bolles, "Random sample consensus: a paradigm for model fitting with applications to image analysis and automated cartography," Communications of the ACM. 24(6), 381-395 (1981).

[20] IEC60825-1:1993+A1 :1997+A2:2001: Safety of Laser Products-Part 1: Equipment Classification and Requirements, International Electrotechnical Commission, Geneva, 2001, IEC safety standard for lasers.

[21] H. J. Kang et al., Software framework of a real-time pre-beamformed RF data acquisition of an ultrasound research scanner, Proc. SPIE 8320, 83201F (2012).

[22] J. Bouguet, Camera calibration toolbox for MAT-LAB®.

[23] A. Myronenko and X. Song, Point-set registration: coherent point drift, IEEE Trans. Pattern Anal. Mach. Intell., 32(12), 22622275 (2010).

EXAMPLE 2

Photoacoustic Reconstruction Using Beamformed RF Data: A Synthetic Aperture Imaging Approach Photoacoustic (PA) imaging is becoming an important tool for various clinical and pre-clinical applications. Acquiring pre-beamformed channel ultrasound data is essential to reconstruct PA images [1-2]. Accessing these pre-beamformed channel data requires custom hardware to allow parallel beam-forming, and is available for only a few research ultrasound platforms or dedicated channel data extension device such as DAQ system. These systems are generally expensive and extensive systems takes time to transfer data from ultrasound machine, so it becomes a limitation of real-time imaging. This fact can be an obstacle of smooth transaction for clinical application, and there is a strong demand to develop a beamforming algorithm utilizing post-beamformed radio frequency (RF) data. T. Harrison et al. has focused the same issue and there solution was change the speed of sound number inside of clinical ultrasound system [3]. The limitation of the approach is that not all clinical ultrasound system provides the accessibility of the speed of sound for beamforming. On the other hand, post-beamformed RF data is generally readily available in real-time and in several clinical and research ultrasound platforms. To broaden the impact of clinical PA imaging, our goal is to devise new PA reconstruction approach based on these post-beamformed RF data.

We generate PA image by using a single receive focus beamformed RF data. These beamformed RF data are considered as pre-beamformed input data to a synthetic aperture beamforming algorithm, where the focal point per received RF line is a virtual element. Since post-beamformed RF data becomes a set of pre-beamformed RF data, the signal property follows that of signals that are received by a large size element [4-6]. Since there is a wide region to receive signal, the improvement of signal-to-noise ratio (SNR) compared to simple photoacoustic delay-and-sum is expected.

In this example, simulation analyses are conducted to confirm the performance of the proposed method, and an experiment is performed to validate its feasibility for real usage.

Method

Ultrasound Beamformer with a Single Fixed Focus

In conventional ultrasound image reconstruction, the distance between receivers to the target is used as the input. The acoustic wave is first generated by transducer, and then it transfers to the target. The signals are reflected at target with impedance mismatch, and finally those signals are received by the ultrasound transducer. At that time, the acoustic time-of-flight (TOF) can be formulated as, $$t(\vec{r_F}) = \frac{1}{c}(|\vec{r_T}| + |\vec{r_R}|) \quad (2.1)$$

where $\vec{r}_F$ is the focus point, $\vec{r}_T$ is the vector from transmit element to the target, and $\vec{r}_R$ represents the vector from the target to the receive element. In clinical ultrasound system, sequential beamforming with dynamic focus or fixed focus are applied as delay-and-sum. In dynamic focusing, the axial focusing point varies corresponding to the depth, while fixed depth focus is used for fixed focusing.

On the other hand, the acoustic TOF of photoacoustic signals are generally half of that of ultrasound because the transmission side of time travel is negligible. Therefore, the acoustic TOF for photoacoustic imaging becomes $$t(\vec{r_F}) = \frac{|\vec{r_R}|}{c}. \quad (2.2)$$

Figure 7:
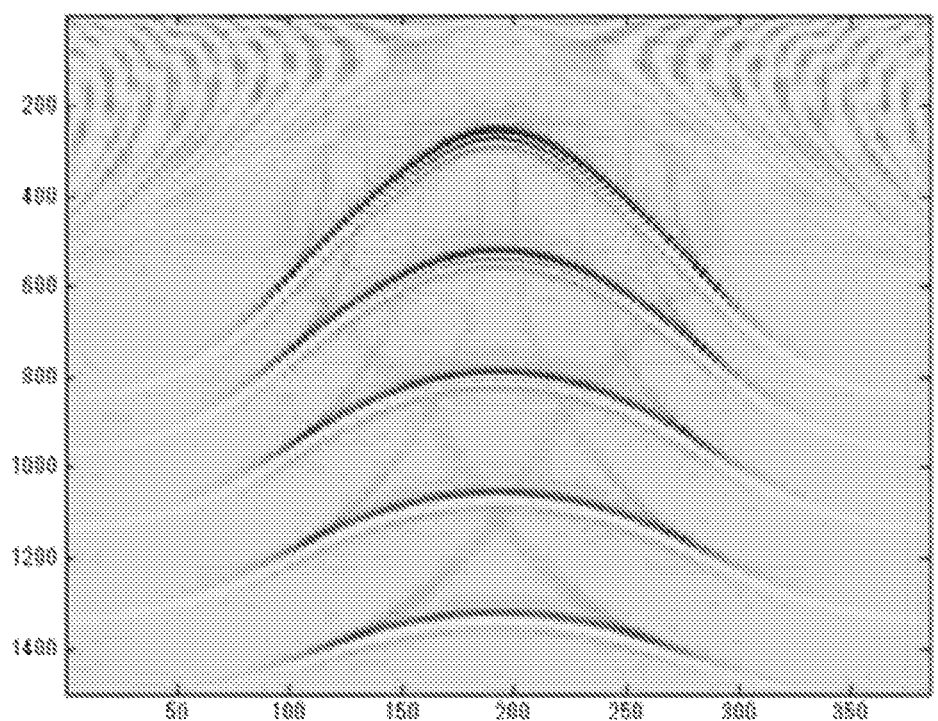
FIG. 7 shows an example of ultrasound beamforming for photoacoustic signals.
Figure 8:
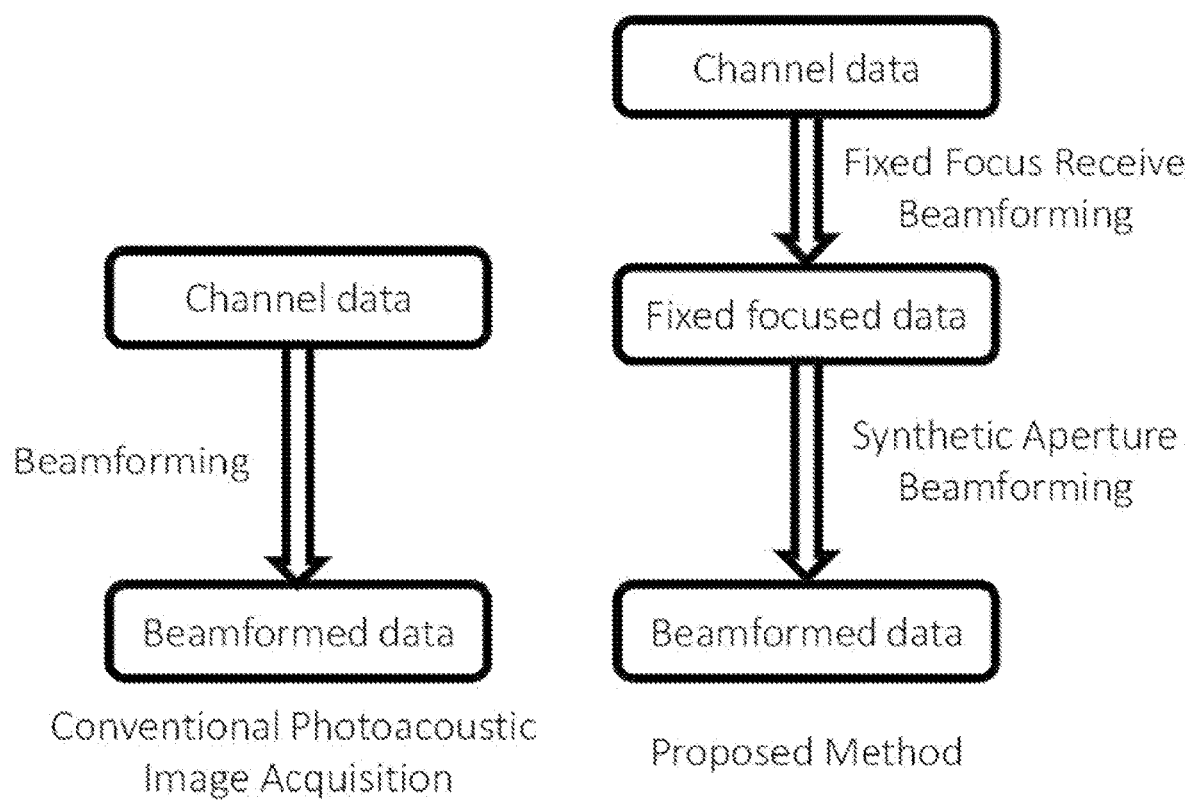
FIG. 8 shows a diagram of a synthetic aperture beamforming method according to some embodiments of the invention.

Since the TOF used in beamforming is different from that of ultrasound, when beamforming is applied to the received PA signals using ultrasound delay, the beamformed RF signals cannot be focused well (FIG. 7). A diagram of a synthetic aperture beamforming method according to some embodiments of the invention is shown in FIG. 8.

Synthetic Aperture Beamformer for Beamformed RF Data

As discussed in previous section, when fixed focusing is applied, the focusing point in axial direction is fixed all the time to construct a post-beamformed line. This indicates that the specific focal depth has a perfect focusing, and surrounding depth is gradually defocused corresponding to the distance from the focal depth. This situation is identical to transmit signals from the focal point, in other word, virtual element. Therefore, the post-beamformed RF data can be regarded as pre-beamformed RF data transmitted from the virtual element. The TOF when fixed focus at z_F is applied becomes $$t(\vec{r_F}) = \frac{|\vec{r'_R}|}{c} \quad (2.3)$$

where $|\vec{r'_R}| = \sqrt{(x_R)^2 + (z_R - z_F)^2}$, and $x_R$, $z_R$ is the lateral and axial location of the receive element, respectively. The delay will be applied in positive axial direction when $z_R \geq z_F$, and negative delay will be applied when $z_R < z_F$. The aperture used in the first beamforming can be used as the sub aperture for the second beamforming, so that a synthetized large aperture information is included in the final product. Since the information a line carry is determined by the aperture size used in fixed focusing, there is no meaning to beamform beyond that line for the second dynamic focusing. Therefore, we define the aperture size for the synthetic aperture beamforming as $$K(z_R) = \frac{2(z_R - z_F)\tan(\alpha/2)}{\Delta} \quad (2.4)$$

where $\Delta$ is the scanning pitch for beamforming. $\alpha$ is the opening angle of the virtual element defined as $$\alpha = 2\arctan\frac{L_A}{2z_F},$$

where $L_A$ is the size of sub aperture for the fixed focusing.

An additional benefit of the approach described herein is its property of SNR improvement because the post beamformed RF data of fixed focusing is similar to that of using a big size element with an acoustic lens. Since different random noise is added for each line beamforming, the effect of noise suppression in proposed method is better than direct dynamic focusing to the channel data. This indicates that the wider aperture used in fixed focusing, the more SNR improvement is expected.

Simulation Analysis
Resolution Analysis

We evaluated the properties of the proposed method through simulation. The purpose of the first analysis is to see the effect on lateral resolution through measuring the full width at the half maximum (FWHM). Five photoacoustic sources are placed at 10 mm, 20 mm, 30 mm, 40 mm, and 50 mm, respectively. As the receiver, 128 elements with 0.48 pitch linear array transducer is assumed. The sampling frequency of 40 MHz is used. The result of photoacoustic images are shown in FIGS. 9A-9C. As a positive control, the result of conventional dynamic receive beamforming to channel data is shown in FIG. 9A. The reconstructed points of synthetic aperture focusing are well focused, but the structure varies depending on the depth of fixed focusing. Moreover, a characteristic could been seen that the lateral width degrades when the focus located at the deep region.

The FWHM for each depth point source by varying fixed focusing depth is shown in FIG. 10. The FWHM of the result using fixed focusing at near field is better than that of dynamic focusing to the channel data, but in the far field, it will be worse. This property could be seen more in the point source located at the near field. The reason why resolution of the reconstruct on far field with far field fixed focus is because the signals to be focused at that point is assumed that is received at the fixed focus depth. Thus, if the distance from fixed focus point and the point source is far away, the resolution becomes worse as expected.

Here we describe the performance of SNR improvement of proposed method. In addition to the simulation condition mentioned in the previous section, a noise which standard deviation is equal to the amplitude of generated photoacoustic signals was added. The resulted images are shown in FIGS. 11A-11C. Due to the effect of noise, the signal at 50 mm depth is hardly visible for conventional PA beamforming, but the image quality of proposed method is clearly improved for that point. Although the background level looks different for different fixed focusing depth, this can be attributed to the invariant scale of the image, which means that can be compensated by normalization.

In FIG. 12, the level of SNR for each depth point source by varying fixed focusing depth is shown. It could be confirmed that the SNR of proposed method is generally better than that of conventional method, but the effect is more obvious when the fixed focusing depth is in far region.

Experimental Setup

Figure 13:
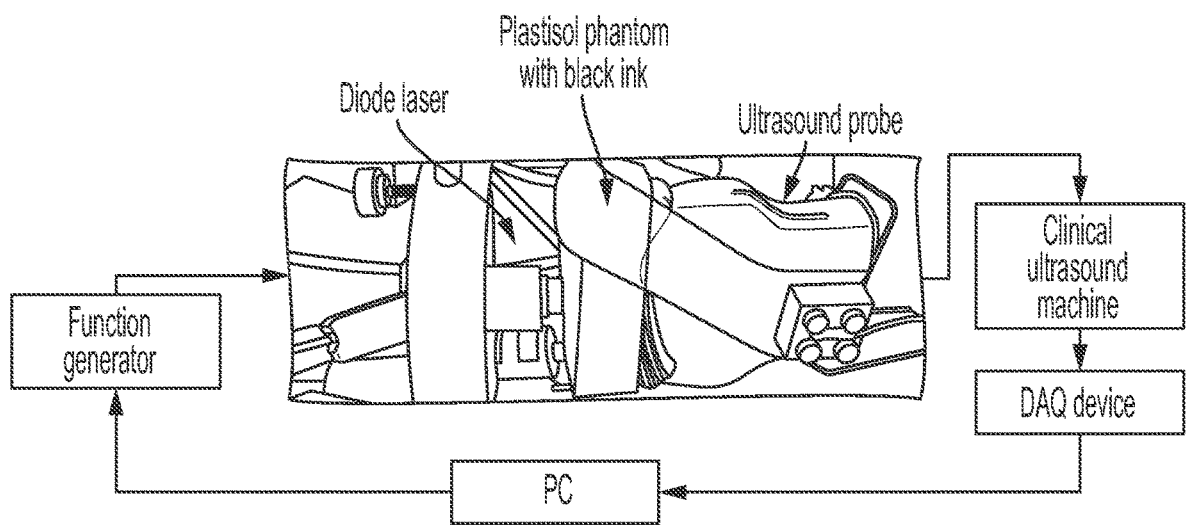
FIG. 13 shows the experimental setup according to some embodiments of the invention.

We validated the proposed method through experiment. The experimental setup is shown in FIG. 13. A 905 nm wavelength pulsed laser diode was used irradiate a plastisol phantom with black ink. The diode laser is driven by a laser driver which is able to generate an electrical driving current that is programmed through a PC. Since the light was absorbed by the surface of the phantom because of the high absorption coefficient of the black ink, PA signals could be generated from a tiny spot in the phantom, which could be regarded as a point source. The generated PA was received by a 0.3 mm pitch 128 elements linear array ultrasound transducer. The received channel data was transferred to a channel data collection device (DAQ) via clinical ultrasound machine (Sonix Touch, Ultrasonix), and saved to the PC. Beamforming algorithms are applied to the collected channel data.

Results

Figure 14:
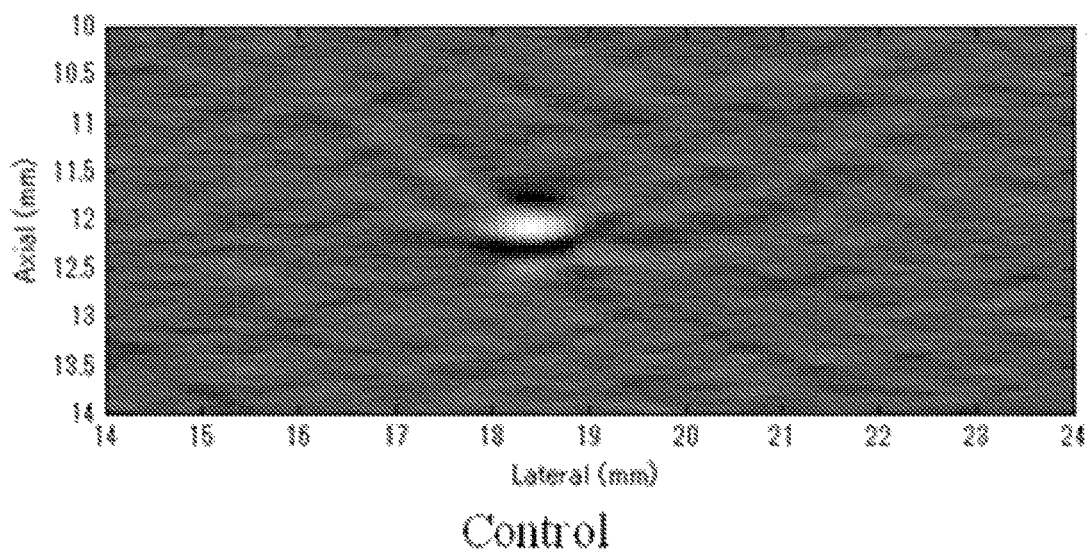
FIG. 14 shows reconstructed photoacoustic images for a control (dynamic focusing for channel data)
Figure 15:
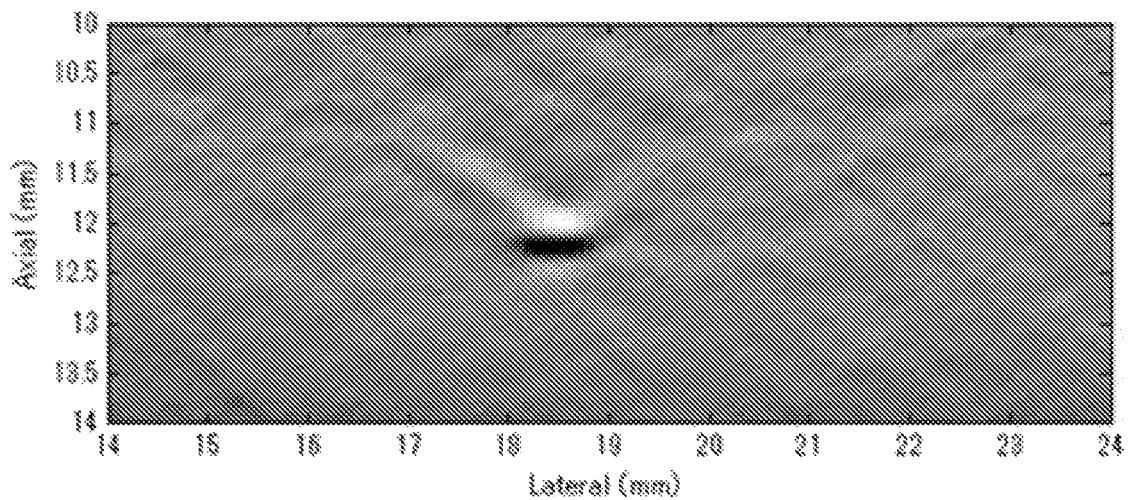
FIG. 15 shows reconstructed photoacoustic images with 9 mm fixed focusing.
Figure 16:
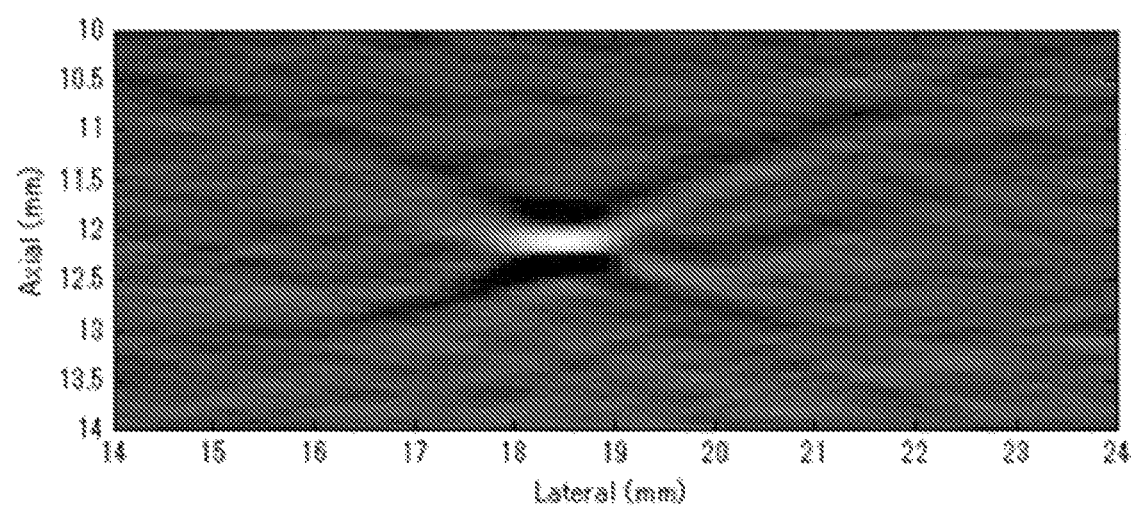
FIG. 16 shows reconstructed photoacoustic images with 21 mm fixed focusing.
Figure 17:
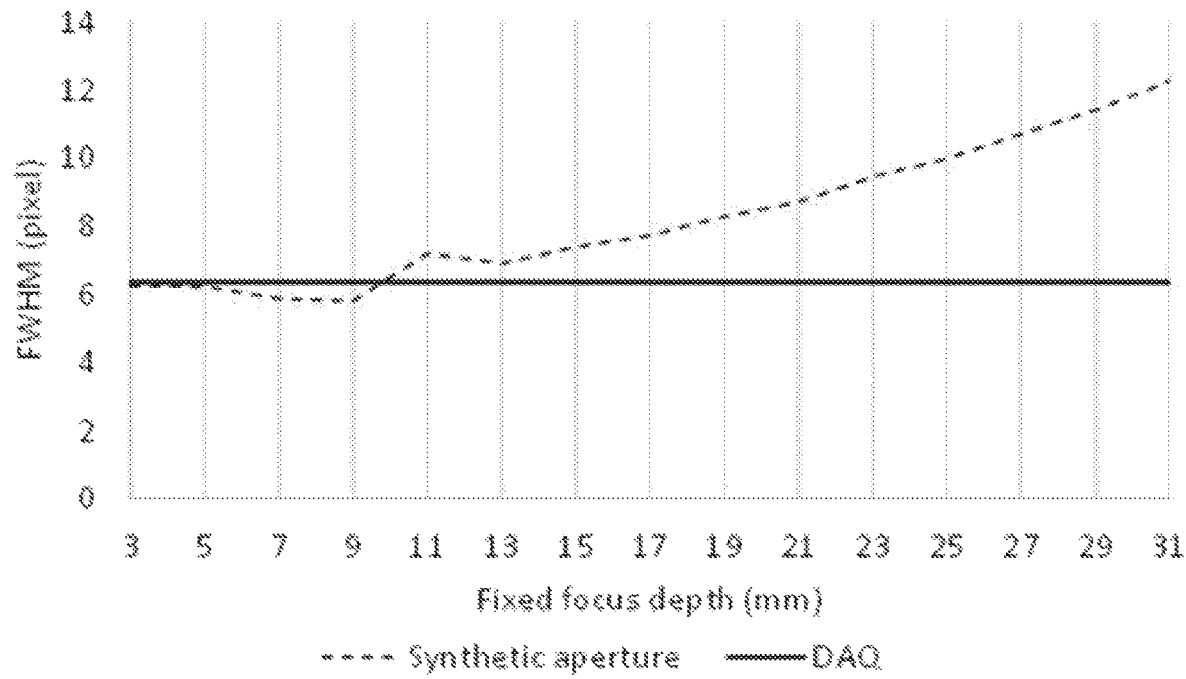
FIG. 17 shows measured FWHM for different fixed focus depths.

The reconstructed results are shown in FIGS. 14-16. The photoacoustic point source could be reconstructed for all fixed focus in the range of 3 mm to 31 mm. FIG. 17 shows that the FWHM of the fixed focusing until 9 mm was better than that of dynamic focusing result to channel data, since wider final synthetized aperture could be used. When applied fixed focusing depth is far from the target such as 21 mm result shown, the reconstructed point was extended in lateral direction. A linear degradation of FWHM could be confirmed by making the fixed focus depth far from the target.

REFERENCES FOR EXAMPLE 2:

[1] Park S., Aglyamov S. R., and Emelianov S., "Beamforming for photoacoustic imaging using linear array transducer," in IEEE Ultrasonics Symp. Proc., 2007, pp. 856-859.

[2] Niederhauser J. J., Jaeger M., and Frenz M., "Comparision of laser-induced and classical ultrasound," Proc. SPIE, vol. 4960, pp. 118-123, 2003.

[3] Harrison T. and Zemp R. J., "The applicability of ultrasound dynamic receive beamformers to photoacoustic imaging," IEEE Trans. Ultrason. Ferroelectr. Freq. Control 58(10), 2259-2263 (2011).

[4] Kortbek J., Jensen J. A., Gammelmark K. L., "Synthetic Aperture Sequential Beamforming," IEEE IUS, 2008.

[5] Frazier C. H. and O'Brien W. D., "Synthetic aperture techniques with a virtual source element," IEEE Trans. Ultrason., Ferroelec., Freq. Contr., 45:196-207, 1998.

[6] Nikolov S. I. and Jensen J. A., "Virtual ultrasound sources in highresolution ultrasound imaging," In Proc. SPIE—Progress in biomedical optics and imaging, volume 3, pages 395-405, 2002.

EXAMPLE 3

Figure 18:
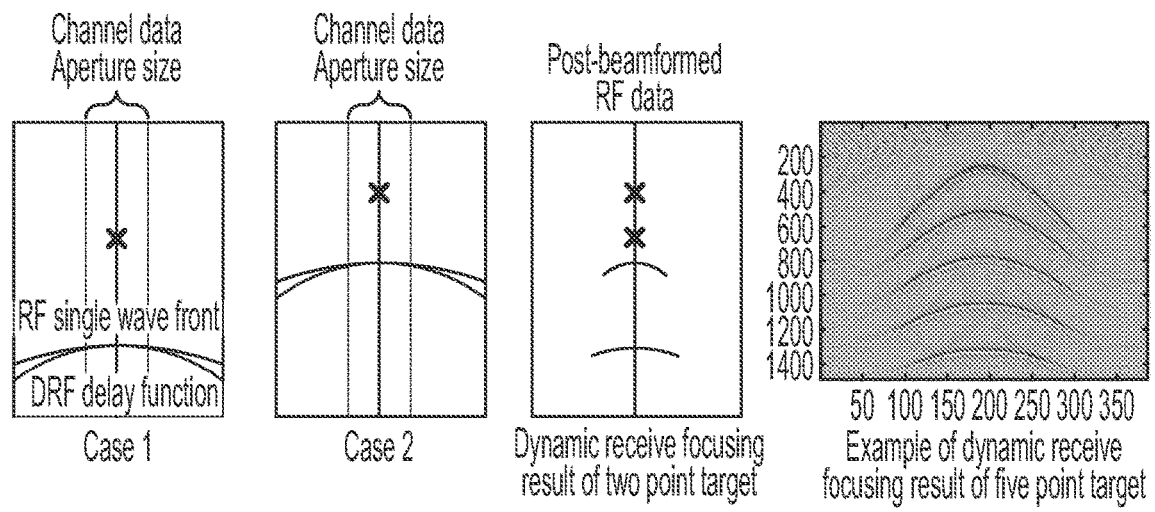
FIG. 18 illustrates a wrong TOF condition for US dynamic receive focusing for photoacoustic data.

Back Projection Based Synthetic Aperture Beamforming using Post-Beamformed RF Data Utilizing Dynamic Receive Beamforming Data As shown in FIG. 18, even if we want to beamform photoacoustic raw pre-beamformed data using an US delay and sum algorithm, it may not work because the time of flight (TOF) is different, and the delay function will be different. However, we know the delay function assuming double TOF, we know that it is similar as our focusing point is always half distance from the true depth we would like to beamform.

Figure 19:
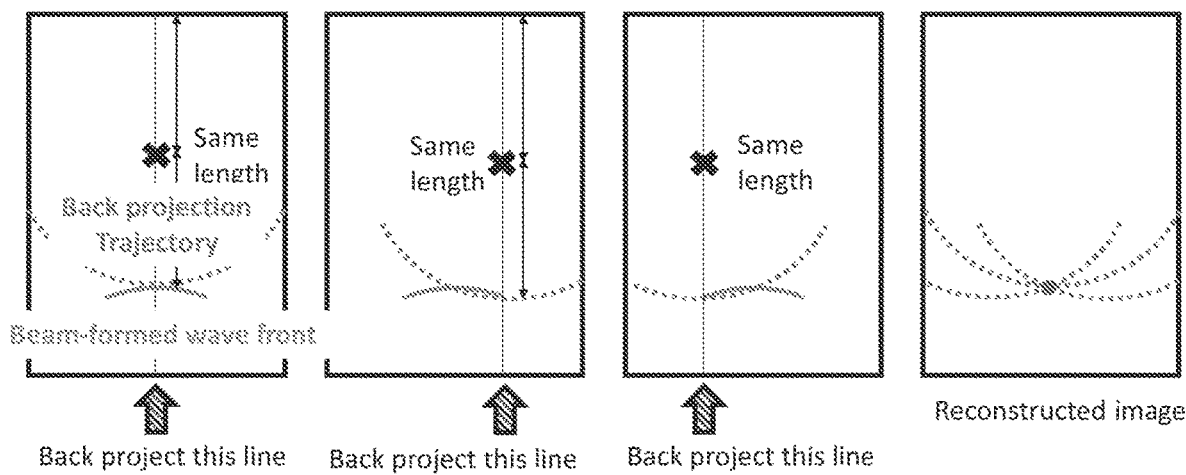
FIG. 19 illustrates the concept of back projection.

The beamformed PA signals under ultrasound beamforming is defocused due to incorrect delay function. In our previous work, we proposed a synthetic aperture based PA beamformer using ultrasound post-beamformed RF data. Ultrasound beamformed RF data are considered as pre-beamformed input data, where its focal point is considered as a virtual element, and a new delay function is applied based on the acoustic wave travel starts from the virtual element. Since, the delay function in dynamically focused ultrasound beamforming takes into account the round trip between the transmitter and the reflecting point, the focus point at each depth becomes the half distance for that in PA beamforming. Thus, it is possible to consider that the virtual point source is swept dynamically in the half distance of the true focal point. FIG. 19 shows an example of implementing proposed algorithm based on back projection.

Figure 20:
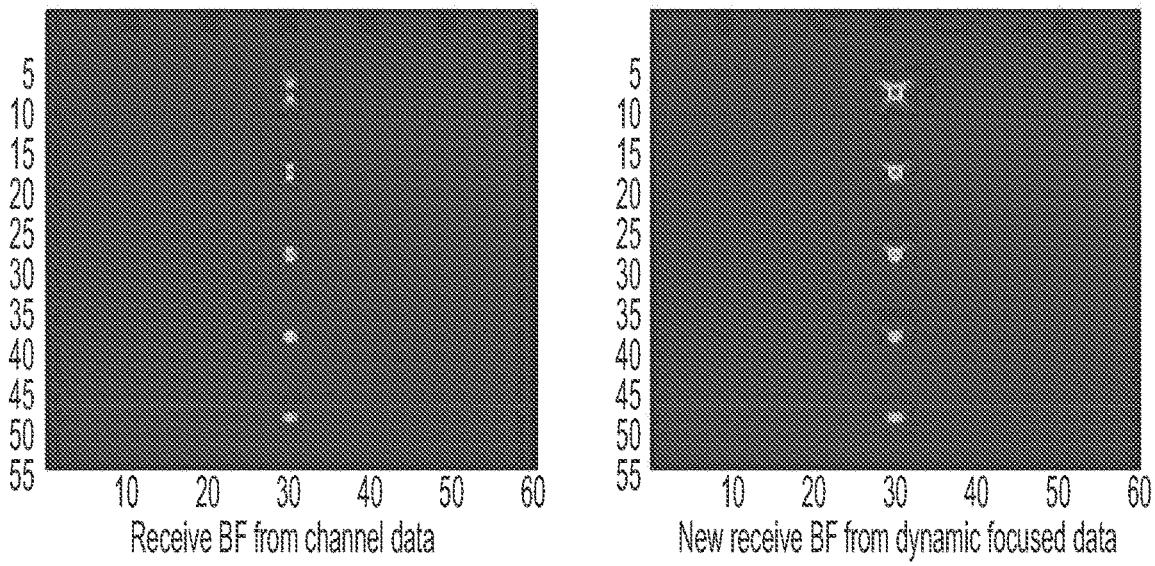
FIG. 20 shows simulation results for a receive beamform from channel data and from dynamic focused data for five point sources.

FIG. 20 shows simulation results for a receive beamform from channel data and from dynamic focused data for five point sources.

EXAMPLE 4

From 2D to 3D: Tracking Outside the Ultrasound Image Plane

Today, most ultrasound systems used in clinic are essentially 2D imaging device. The commonly used 3D volume scan can also be considered as a series of 2D image. Due to the requirement of medical ultrasound image formation, imaging probes are designed to transmit and receive nearly collimated beam along the elevational direction. This means the elevational detection capability of the traditional ultrasound is very limited.

Using the mid-plane detection technique, an integrated active element can be precisely located to the ultrasound image plane. The elevation detection range can be extended to 1-2 cm, since the probe reception angle is not a limitation anymore in this case. However, the active element still need to receive the imaging pulses from the probe, so the active ultrasound element still cannot operate far from the probe mid-plane. This is an undesired limitation in some applications. One example is the image-guided surgery (IGS) system, which is often used in modern surgical procedures to provide surgeons with additional information support and guidance leading to less trauma for the patient. Specific benefits to the patient can include cost reduction of the procedure, reduced morbidity rates, and shorter recovery times. In IGS systems, ultrasound is often used to provide a visualization of underlying tissue structures or anatomy that cannot be seen with the naked eye. When integrating ultrasound with this kind of multi-modality system, off-plane detection is desired not only because of the tool tracking propose, but also the calibration requirement.

To perform advanced forms of guidance with ultrasound, such as virtual image overlays or automated robotic actuation, an ultrasound calibration process must be performed. This process recovers the rigid body transformation between a tracked marker attached to the transducer and the ultrasound image.

Basic Principle and Methods: Off-Plane Point Detection

Figure 21:
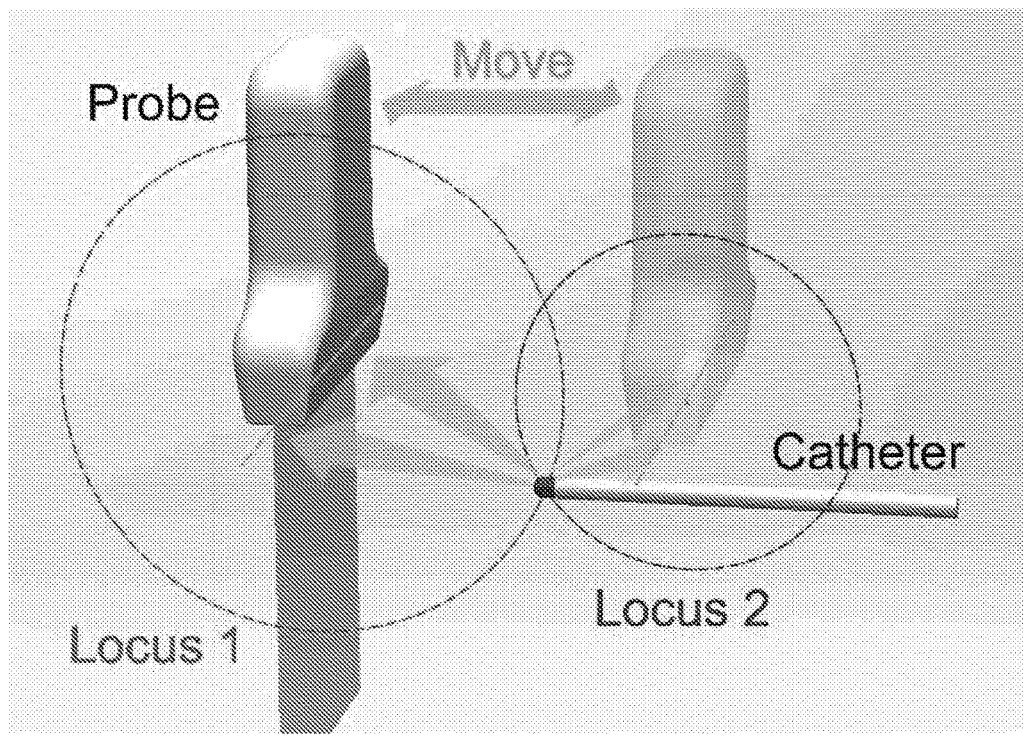
FIG. 21 shows the configuration of the off-plane ultrasound point detection.

Since the transmitted beam from the imaging probe has a fixed small divergence along the elevational direction, it is not possible to detect it when the receiver is far away from the beam. However, the active ultrasound element can be designed with an omnidirectional transmission angle, which means it is possible to receive ultrasound pulses sent from the active element by the probe even in an off-plane configuration. FIG. 21 shows the configuration of the off-plane ultrasound point detection.

Asynchronous Homodyne Ultrasound Wavefront Detection

In the off-plane tracking method, the ultrasound probe receives the signal from a point ultrasound source far away from mid-plane. Due to the receiver element directionality, the detected signal can be very weak. Since the goal is to localize the signal source position, and the signal source is known to be a point source, in this case the distance between the signal point source and the imaging array uniquely determines the acoustic wavefront shape. So once the wavefront is detected, the distance between the source and image array can be derived without knowing the time of flight. In other words, the ultrasound transmission and reception do not need to be synchronized. For these applications, we developed an asynchronous homodyne ultrasound wavefront detection method to improve the received signal quality.

In this method, the point signal source is modulated with a pre-determined frequency, the produced ultrasound wave will also be a pulse sequence with the exactly same modulation frequency, so homodyne detection can be performed on the acquired pre-beamforming images. By extracting the phase and amplitude of the modulation signal from each channel, and the ultrasound wavefront can be recovered. The method is essentially a software implemented lock-in amplifier. So even in the very noisy cases, like the SNR<1, the system may still be able to extract the ultrasound wave front.

Figure 22:
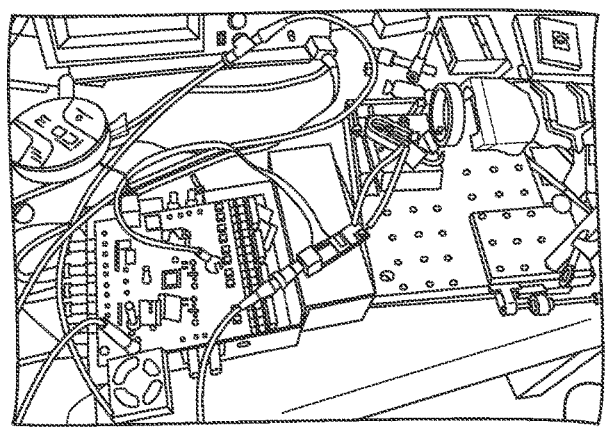
FIG. 22 shows the system setup to validate the asynchronous homodyne ultrasound wave front detection method.
Figure 23:
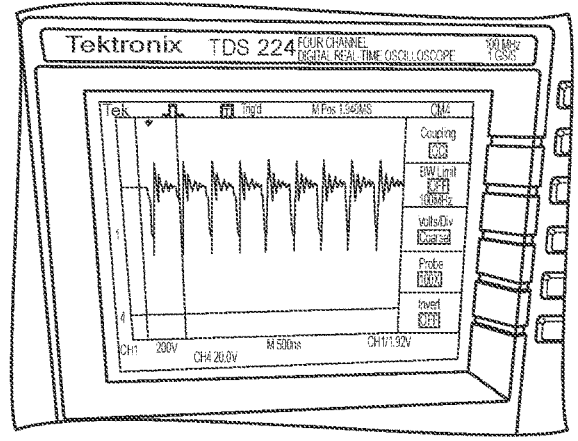
FIG. 23 shows the modulation signal of the laser. The PLD is driven by a customized electronic system.

In the validation experiment, a PLD based photoacoustic system is used to generate a low intensity point ultrasound source. FIG. 22 shows the system setup to validate the asynchronous homodyne ultrasound wave front detection method. The light source is a Laser Components Inc. 905D3S3J09R PLD with an aspherical pair focusing lens. A piece of black plastisol phantom is attached to the Sonix L14-5W probe as the photoacoustic target material and the coupling medium. A SonixDAQ system is used for the pre-beamforming data collection. FIG. 23 shows the modulation signal of the laser. The PLD is driven by a customized electronic system. The pulse energy is configured to 1.5 µJ per pulse, and a soft plastisol block is used as the photoacoustic target material. With this configurations, the produced photoacoustic signal is weak and result in a low SNR. In addition, a 5-14 MHz frequency linear probe is used to receive the signal. According to the results presented in the previous sections, the majority of the PLD photoacoustic signal energy is lower than the probe frequency range. This makes the detected signal even weaker. The purpose of all this setup is to generate a low quality pre-beamforming image and test the proposed method in the low SNR conditions.

Figure 24:
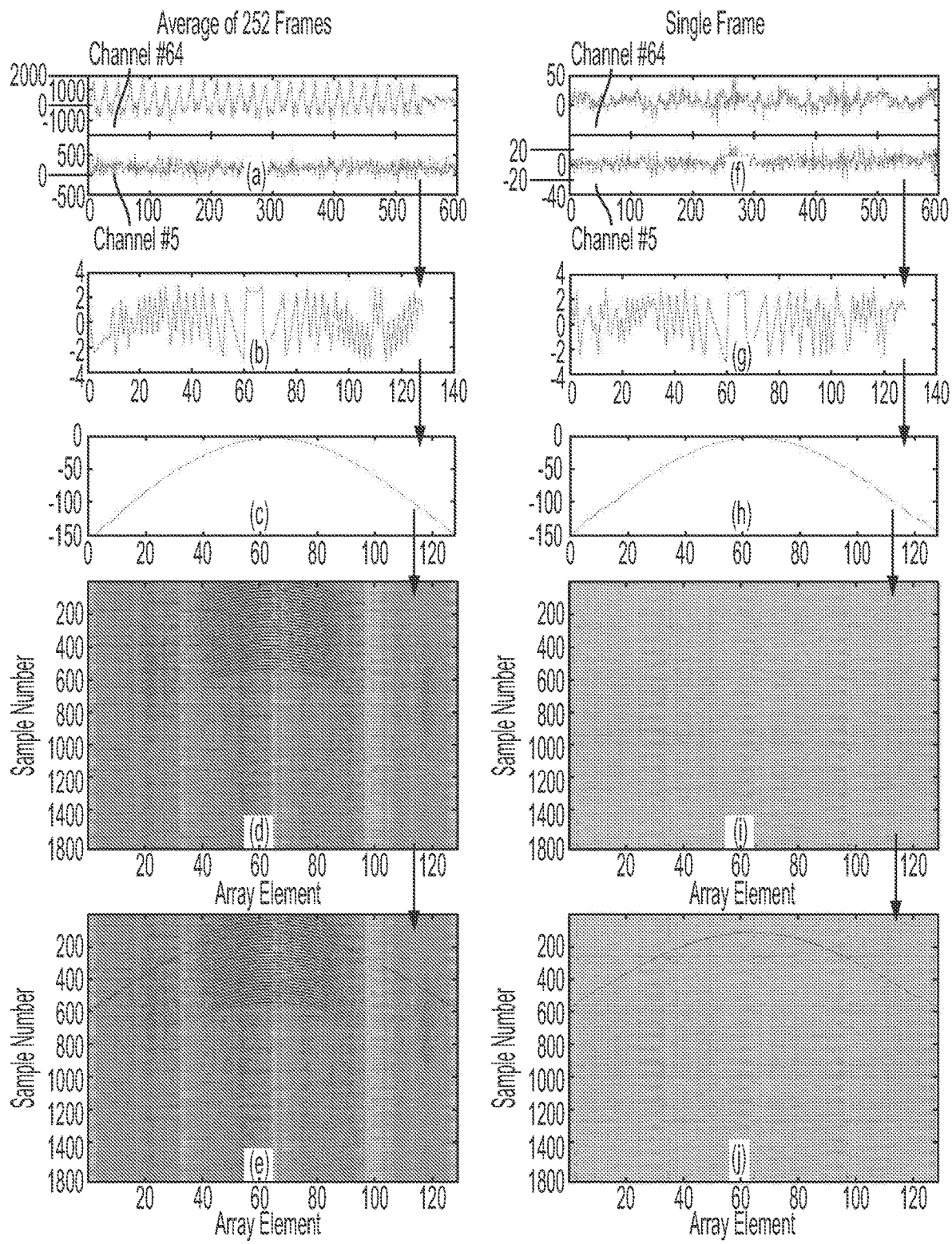
FIG. 24 shows the data processing procedures and the result comparison of the wavefront detection with different SNR.

FIG. 24 shows the data processing procedures and the result comparison of the wavefront detection with different SNR. The right column (f-j) shows the proposed data processing method with a single pre-beamforming image. The left column (a-e) shows the same method with the averaged data from 252 frames, as a comparison. Theoretically, the average will improve the data SNR by around 16 times. In the first row (a and f), the received channel signal from element #5 and #64 are plotted. Since line #64 is closer to the photoacoustic spot, the plot shows higher signal amplitude. From a, the channel #64 plot shows a very clear photoacoustic pulse sequence with the pre-programmed 2 MHz laser repetition frequency. On channel #5, the signal is too weak to be distinguished. In the single frame data shown in figure f, even on channel #64 the pulse sequence is not clear due to the low SNR. The second row (figure b and g) shows the signal phase of the received 128 waveforms, at the frequency of 2 MHz, the laser modulation frequency. The third row (figure c and h) shows the unwrapped phase. Since all the channels are sampled at the same frequency, which is $f_s$=40 MHz, the unwrapped phase curve should have the same shape as the photoacoustic signal wavefront. Knowing the signal modulation frequency $f_m$=2 MHz, it is easy to calculate the sample points n from the phase Φ:

$$n = \frac{\Phi}{2\pi} \frac{f_s}{f_m}.$$

The fourth row (d and i) shows the pre-beamforming images. From the averaged data, the wavefront sequence can be clearly seen in the central channels that are closer to the photoacoustic signal source. From the single frame image, since the SNR is close or lower than 1, the wavefront sequence cannot be distinguished. Conventional wavefront detection will fail with this kind of image quality. The last row plots the wavefronts detected by the proposed method on top of the pre-beamforming images. From e, it can be seen that the detected wavefront matches the shape of the curve on the image, this indicates that the wavefront is detected correctly. On the right column, although the SNR is very low, a same wavefront is also correctly detected.

The result indicates that the proposed unsynchronized homodyne ultrasound wavefront detection method is capable to extract the photoacoustic wavefront from a very low SNR pre-beamforming data. This method potentially enables the use of low energy PLD laser in iPASS, off-plane catheter detection and many other photoacoustic tracking and calibration applications.

Channel Data Acquisition using a Clinic System: Channel Mask and Inversed Beamforming Another requirement in the off-plane tracking is to acquire the pre-beamforming ultrasound data from the imaging probe. An ultrasound DAQ system can be used for this purpose. A typical example is the SonixDAQ system from Ultrasonix Inc. It is a device with 128 receiving channel ultrasound analog frontend, ADC, buffer and USB2.0 data interface, designed to interface ultrasound probes directly. However, this type of devices are built for research purpose, and not commonly available in clinic facilities. To make the off-plane tracking generally deployable in the real world healthcare environment, there is a demand of using conventional clinical ultrasound systems to acquire the data. The major challenge is that almost all modern clinical ultrasound systems have a hardware beamformer or low level embedded software beamformer. The raw signal acquired from each probe element is not accessible for the users.

One method to solve this problem is to bypass the integrated beamformer. Since ultrasound reception beamforming is essentially the delay and sum between different channels, if the channel number is reduced to 1, the beamformer will not have any effect to the raw element data. Since the clinic ultrasound system acquires one RF line every time, theoretically the RF line waveform should be the same as the raw signal received by the corresponding element. Using this method, a 2D pre-beamforming image can be acquired by scanning the RF lines over the field of view.

This method requires the signal source transmit for each RF line in the ultrasound image acquisition, and the firing need to be controlled by the ultrasound line trigger. A 905D3S3J09R PLD is used in the experiment setup due to its high repetition rate and random time firing capability. The laser is focused on a black plastisol phantom, which is used as the photoacoustic target material. A SonixTouch clinical ultrasound imaging system with a L14-5W probe is used for the data acquisition. A customized data acquisition software (MUSiiC Software Kit) based on the Texo SDK is used to configure the ultrasound receiving aperture. For comparison purpose, a SonixDAQ system is also connected to the same probe to acquire the raw channel data.

Figure 25:
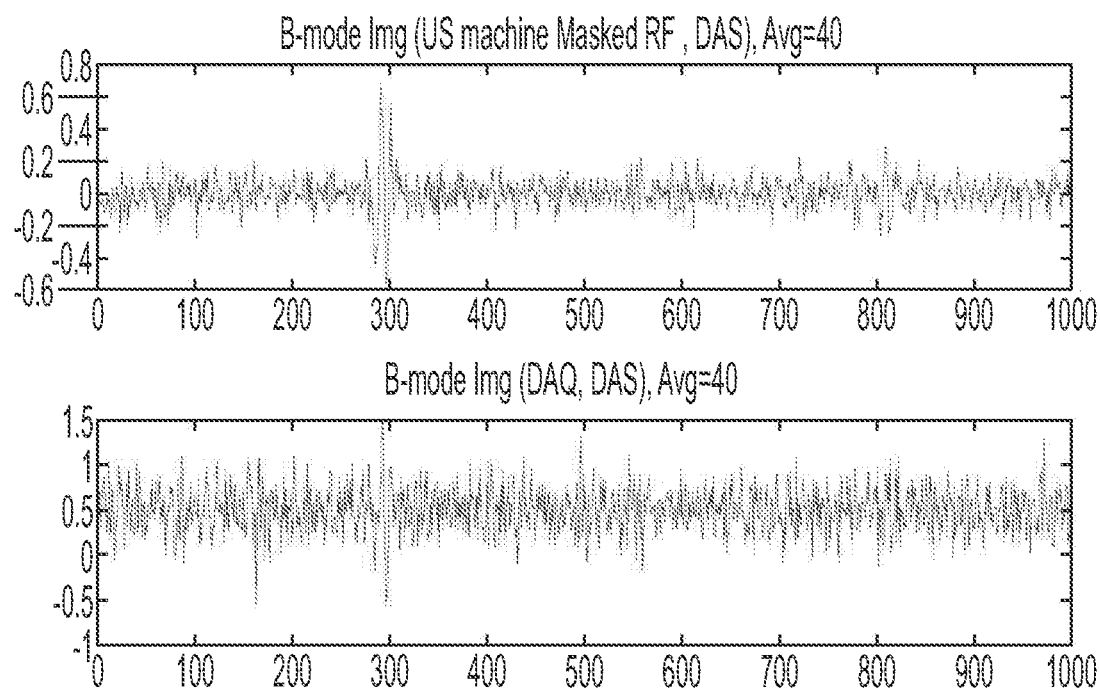
FIG. 25 shows the signal comparison of the same channel between the DAQ and the clinical ultrasound system bypassing the beamformer.

FIG. 25 shows the signal comparison of the same channel between the DAQ and the clinical ultrasound system bypassing the beamformer. The top plot shows the data acquired by the clinical ultrasound system with the beamformer bypassed. The bottom plot shows the data acquired by the SonixDAQ system. The peak position of the utrasound signal is very close, and the waveform is hard to compare due to the high noise. The signal from the clinical ultrasound system has a slightly better SNR.

Figure 26:
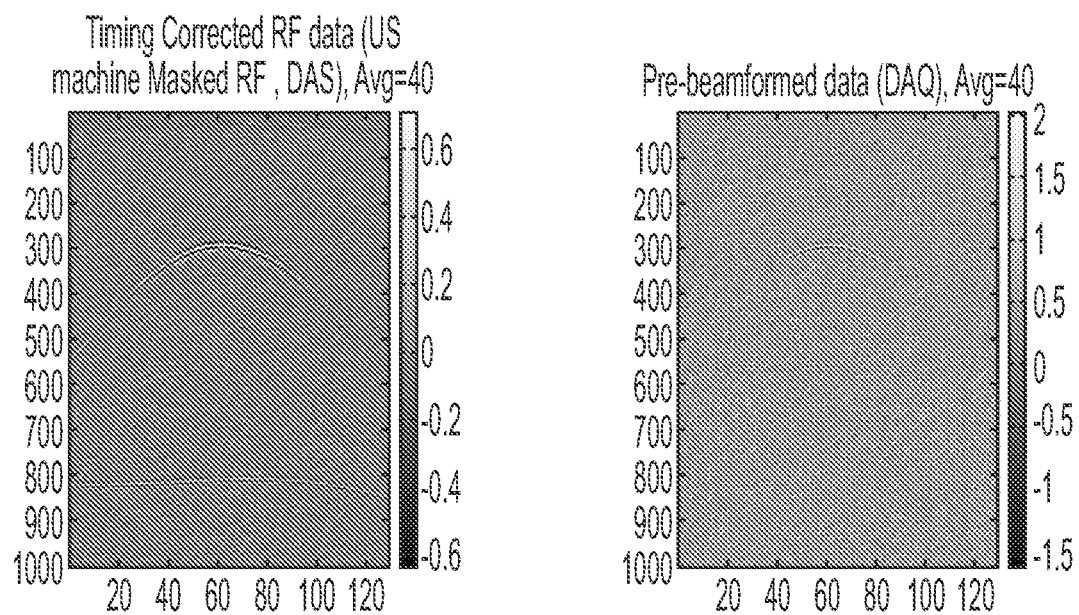
FIG. 26 shows the comparison of the pre-beamforming images.
Figure 27:
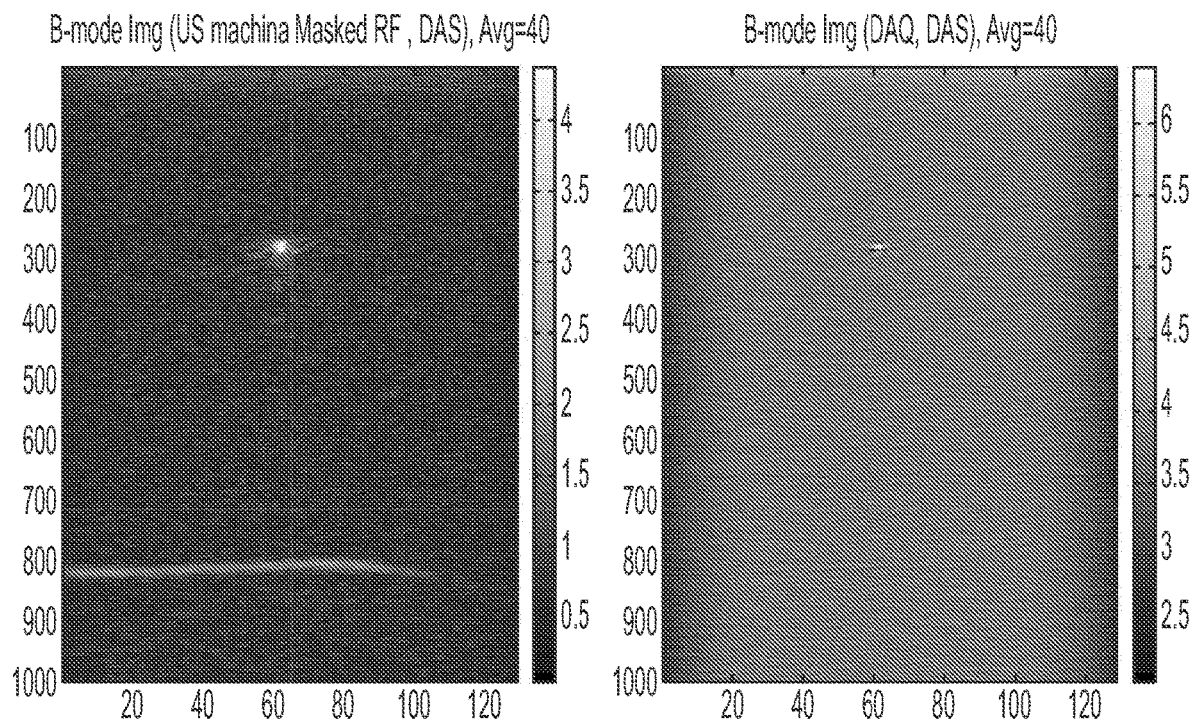
FIG. 27 shows the beamformed images.

FIG. 26 shows the comparison of the pre-beamforming images. The left image shows the data acquired by the clinical ultrasound system with the beamformer bypassed. The right image shows the data acquired by the SonixDAQ system. It is clearer that the image acquired by the clinical system has an even better SNR than the DAQ system. The beamformed images are shown in FIG. 27. The left image is based on the clinical ultrasound system data. The right image is based on the DAQ data. This result indicates that using clinical ultrasound system with a reduced receiving aperture is a feasible way to acquire the pre-beamforming signal.

There are two possible limitations of the first method. The first one is that reducing the receiving aperture to 1 is not a commonly available function in clinical ultrasound systems. In our experiment, this is achieved by using a customized software and channel mask method. The second limitation is the low efficiency. Since every laser firing there is only one element is receiving, most of the ultrasound wave reaches the probe is not captured. So more laser pulses is needed to achieve the desired SNR.

We now describe a second method called the inverse beamforming to address these problems. The idea of this method is based on the Huygens-Fresnel principle. If a clinical ultrasound system running in the conventional receiving mode is used to acquire the signal, the captured image is neither a pre-beamforming image, nor a B-mode image, because the beamforming is incorrect due to the single-travel issue. However, all information is still preserved in the incorrectly beamformed image. It can be considered as a snapshot of a propagating wavefront at a certain timing. According to Huygens-Fresnel principle, giving any wavefront, we can assume that each point on this wavefront is a sub-signal source. So it is possible to reverse the beam propagation process of any wave from a wavefront snapshot. In this specific case, each pixel on this image can be considered as a sub-signal source. The value of the pixel represents the signal amplitude. We can "fire" an ultrasound pulse from each pixel, and let the wavefront propagate with a negative time flow (time reversal). By summing up all the time reversal wavefronts, and correct the known distortion caused by the incorrect beamforming, the original channel data can be derived.

Figure 28:
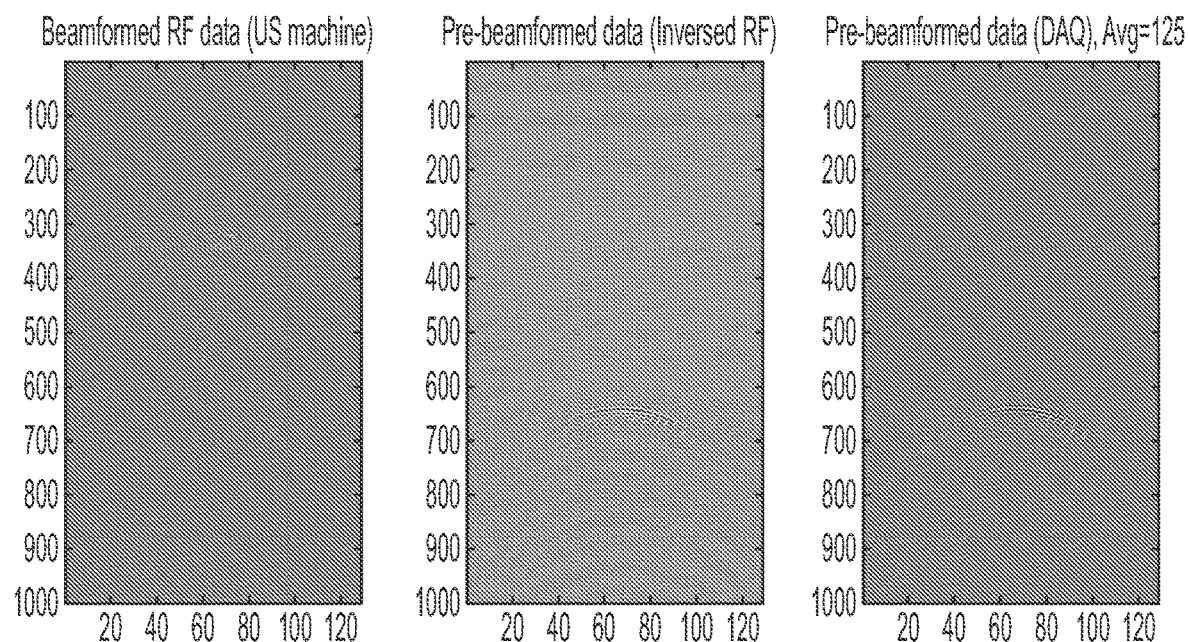
FIG. 28 shows the comparison of the proposed method and the DAQ reference.

FIG. 28 shows the comparison of the proposed method and the DAQ reference. The left-hand image is the incorrectly beamformed photoacoustic image acquired by the clinical ultrasound system. The middle image is the pre-beamforming image processed from the left image using the proposed inverse beamforming method. The image is acquired with a receiving aperture size of 64. The right-hand image is the pre-beamforming image acquired by the DAQ. In the inverse beamformed image, the wavefront is correctly reconstructed. Most of the details, like the ringing after the main signal peak, are also preserved. A low frequency ripple artifact can be clearly seen in the inverse beamformed image.

Figure 29:
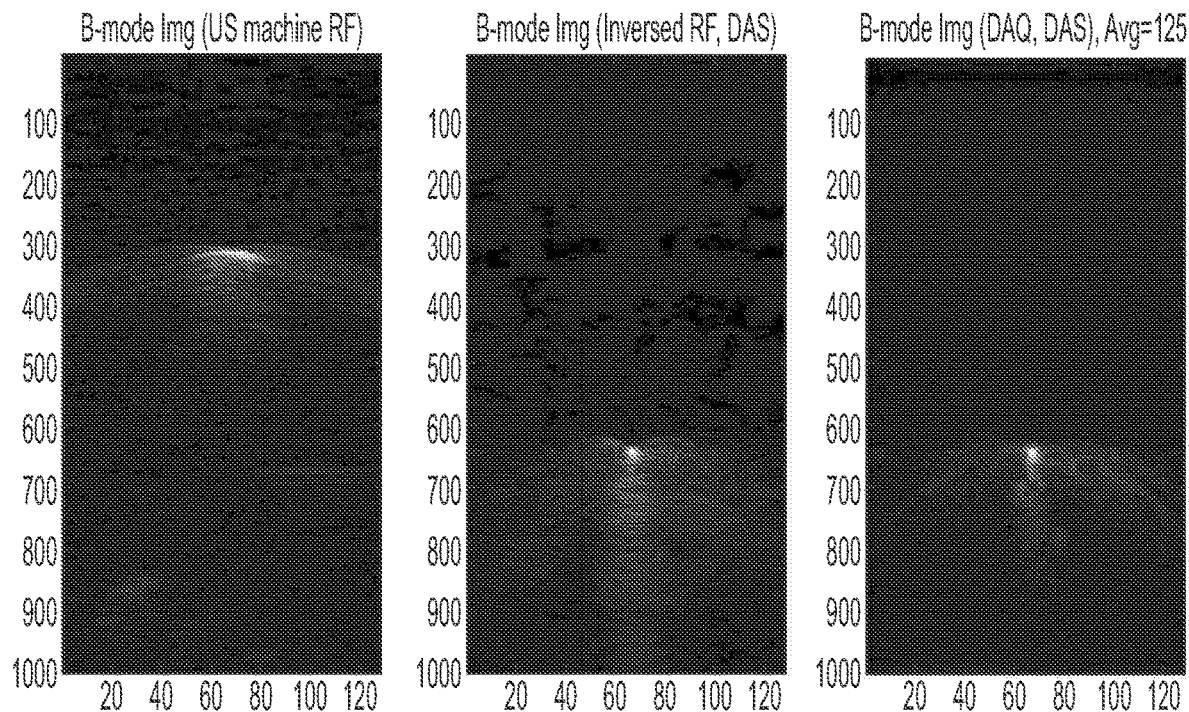
FIG. 29 shows the corresponding B-mode images after the DAS beamforming and envelop detection and log compression.

FIG. 29 shows the corresponding B-mode images after the DAS beamforming and envelop detection and log compression. The left-hand plot shows the incorrectly beamformed photoacoustic B-mode image acquired by the clinical ultrasound system. The middle plot shows the DAS B-mode image processed from the clinical system data using the proposed inverse beamforming method. The right-hand plot shows the B-mode image based on the DAQ data. The result indicates that the proposed inverse beamforming method is capable to reconstruct the pre-beamforming photoacoustic signal from the clinical ultrasound system data.

Example 5:

Synthetic Aperture Based Photoacoustic Image Re-beamforming From Ultrasound Post-beamformed RF Data Photoacoustic (PA) imaging is becoming an important tool for various clinical and pre-clinical applications [1]. PA imaging enables to obtain functional information which visualize optical absorption property, and it has a great affinity with conventional ultrasound imaging which delineates the anatomical structure of the body. In order to construct a PA image, it is necessary to receive signals from different locations through scanning. While various scanning strategies are considered, the ultrasound array transducer can be regarded as the easiest accessible receiver because it is widely used in the clinic for ultrasound imaging [2-4]. Also, receiving PA signals from the same receiver as ultrasound imaging simplifies fusion of PA and ultrasound images [5].

Considering PA image formation, acquiring pre-beamformed channel data is essential because most of clinical ultrasound systems only provide the access to the post-beamformed data in which the ultrasound delay function is taken into account [2,6]. Accessing these pre-beamformed channel data requires custom hardware to allow parallel beam-forming, and is available for only a few research ultrasound platforms or dedicated channel data acquisition device such as DAQ system [7]. These systems are generally expensive, and extensive systems take time to transfer data from the ultrasound machine, so it can become a limitation of high frame-rate real-time imaging [8]. More importantly, most clinical ultrasound systems do not offer PA beamforming which hinders clinical transition. T. Harrison et al. have focused on this issue and their solution was to change the speed of sound parameter of clinical ultrasound systems [9]. However, the access for changing the speed of sound is not common, and generally the changeable range is bounded by the realistic sound speed of human tissue, which is not sufficient for PA beamforming. In contrast, post-beamformed radio frequency (RF) data is generally readily available with several clinical and research ultrasound platforms, thus to broaden the impact of clinical PA imaging, our goal is to devise a new PA image reconstruction approach based on these ultrasound post-beamformed RF data.

We propose a synthetic aperture (SA) based beamforming algorithm utilizing ultrasound post-beamformed RF data as the pre-beamformed data for PA beamforming. Considering that a single receive focus is applied in ultrasound beamforming, the focal point per received RF line is regarded as a virtual element [10-13] to form a set of pre-beamformed data for PA beamforming. In other words, ultrasound post-beamformed RF data becomes a set of PA pre-beamformed RF data starting from the virtual element to backward and forward, and a forward delay-and-sum (DAS) and inverse DAS can be applied to the far field and the near field of the fixed focusing point, respectively. This theory is also applicable to the dynamic receive focused ultrasound data by assuming the virtual point is swept corresponding to the depth.

Theory

Ultrasound Beamforming

In ultrasound image reconstruction, the delay function in delay-and-sum beamforming algorithm is computed from the distance between receivers and the target [14]. The acoustic wave is first transmitted from the ultrasound transducer, through a medium with a specific velocity, reflected at boundaries with impedance mismatching, and the back-scattered sound is received by the ultrasound transducer. The entire acoustic time-of-flight (TOF) during this process can be formulated as, $$t_{US}(\vec{r_F}) = \frac{1}{c}(|\vec{r_T}| + |\vec{r_R}|), \quad (5.1)$$

where $\vec{r}_F$ is the focus point originating from ultrasound image coordinate, $\vec{r}_T$ is the vector from the transmit element to the focal point, $\vec{r}_R$ is the vector from the focal point to the receive element, and c is the speed of sound. In clinical ultrasound system, sequential beamforming with dynamic focus or fixed focus is generally applied as delay-and-sum algorithm. In dynamic focusing, the axial component $z_F$ of the focusing point moves corresponding to the depth, while a single fixed depth focus is used for the fixed focusing.

On the other hand, the acoustic TOF of PA signals are half of that of ultrasound, because the acoustic wave is generated at the target by absorbing light energy, and the transmission side of time travel is negligible. Therefore, the acoustic TOF for photoacoustic imaging becomes $$t_{PA}(\vec{r_F}) = \frac{|\vec{r_R}|}{c}. \quad (5.2)$$

Figure 30:
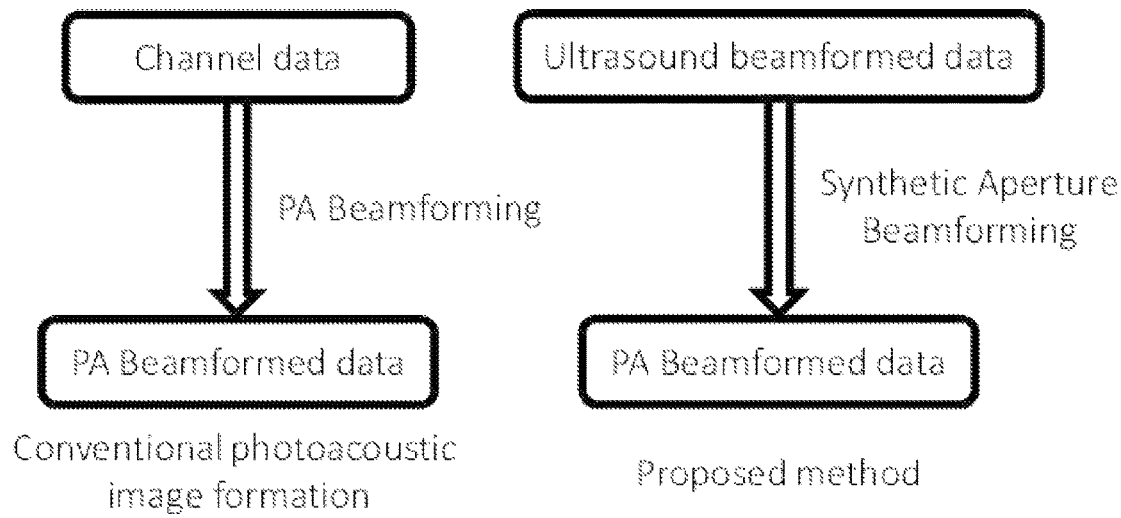
FIG. 30 shows a diagram of synthetic aperture beamforming according to some embodiments of the invention.

Since the TOF taken in account in beamforming is different from that of ultrasound, when beamforming is applied to the received PA signals using ultrasound beamforming delay, the beamformed RF signals are defocused. FIG. 7 shows an example of ultrasound beamforming for photoacoustic signals. When five point targets are placed, the points are extended with orbits in the reconstructed image due to incorrect delays. FIG. 30 shows a diagram of synthetic aperture beamforming according to some embodiments of the invention.

Synthetic Aperture Based PA Beamforming from Post-Beamformed RF Data

Figure 31:
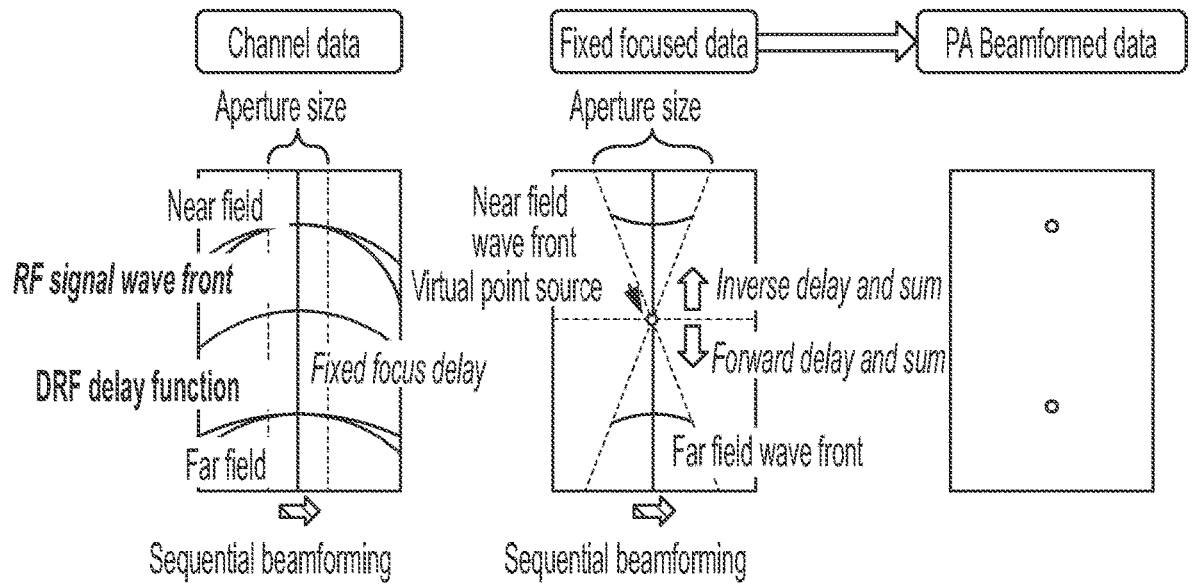
FIG. 31 shows the characteristics of channel data and fixed focus data.

In the proposed beamformer, the ultrasound post-beamformed RF is not considered as defocused useless data, but as the pre-beamformed RF data for PA beamforming. When fixed focusing is applied, the focusing point in the axial direction is fixed all the time to construct an ultrasound post-beamformed line. This indicates that a perfect focusing is applied at the specific focal depth, and the farther the region is from the focal depth, the more the true focus point will be defocused. The mechanism is applicable to both photoacoustic and ultrasound signals, except the delay function for photoacoustic signals is the half of that for ultrasound signals. Starting from the single focusing depth, the defocused signals extend these orbits in backward and forward as if the pre-beamformed signals transmitted from the focal point, in other word, a virtual element. FIG. 31 shows the characteristics of channel data and fixed focus data. In channel data, the wave front of receive RF signals expands corresponding to the depth (solid line). When fixed receive focusing is applied, the delay function is only optimized to the focus depth (dotted line). As a result of fixed receive focusing, the focal point can be regarded as a virtual point source, so that inverse and forward delay and sum can be applied. In this sense, the ultrasound post-beamformed RF data is regarded as PA pre-beamformed RF data. For convenience, we define the ultrasound beamforming with a fixed focus as the first beamforming, and the following SA beamforming as the second beamforming. The TOF from the virtual element, when a fixed focus at $z_F$ is applied, becomes $$t(\vec{r}_F') = \frac{|\vec{r}_R'|}{c}, \tag{5.3}$$

where $$|\vec{r}_R'| = \sqrt{(x_R)^2 + (z_R - z_F)^2}, \tag{5.4}$$

$\vec{r}_F' = \vec{r}_F - \vec{z}_F$, and $x_R$, $z_R$ is the lateral and axial components of $\vec{r}_R$, respectively. The dynamic receive delay function will be applied in positive axial direction when $z_R \geq z_F$, and negative dynamic focusing delay will be applied when $z_R < z_F$. The aperture used in the first beamforming is used as the sub aperture for the second beamforming, so that a synthetized large aperture information is included in the final product. The diagram is shown in FIG. 31.

This theory is applicable to the dynamic focused ultrasound beamformed RF data. Since, the delay function in dynamically focused ultrasound beamforming takes into account the round trip between the transmitter and the reflecting point, the focus point at each depth becomes the half distance for that in PA beamforming. Thus, it is possible to consider that the virtual point source is swept dynamically in the half distance of the true focal point. The only difference compared to the fixed focusing case is that $z_F = 2z_R$ is always true.

Resolution and SNR

The lateral resolution of photoacoustic imaging is determined by F-number, which is the ratio of aperture size to the focusing depth. In PA beamforming, the relationship between F-number (F#) and lateral resolution can be described as $$\text{Lateral Resolution} \propto \frac{F}{D} = F\#, \tag{5.5}$$

where F is focusing depth and D is the aperture size. Therefore, to achieve high resolution PA image, the condition with small F-number, in other words small focusing depth and big aperture, is desired. In ultrasound imaging, the frequency of the received signals is another factor affects the lateral resolution, but it is not applicable to the PA image because the transmission frequency is defined by wide spectrum of probe bandwidth.

In the SA beamformer, four factors are involved to determine the lateral resolution: the fixed focusing depth $z_F$, SA beamforming focusing depth $z_R$, fixed focusing aperture size $D_{US}$, and aperture size for the second synthetic aperture beamforming $D_{SA}$. The fixed focusing depth and the fixed focusing aperture size is determined by the ultrasound system as conventional beamformer, and the second beamforming parameters are determined when the algorithm is applied.

Now, we discuss the effective focusing depth and aperture, which is the parameters define the resolution of the reconstructed PA image. The effective focusing depth of the proposed SA beamformer is $$F_{SA} = |z_F - z_R|. \tag{5.6}$$

$z_F$ is considered as a virtual element point source, and the new focusing depth is computed starting from the virtual element.

Figure 32:
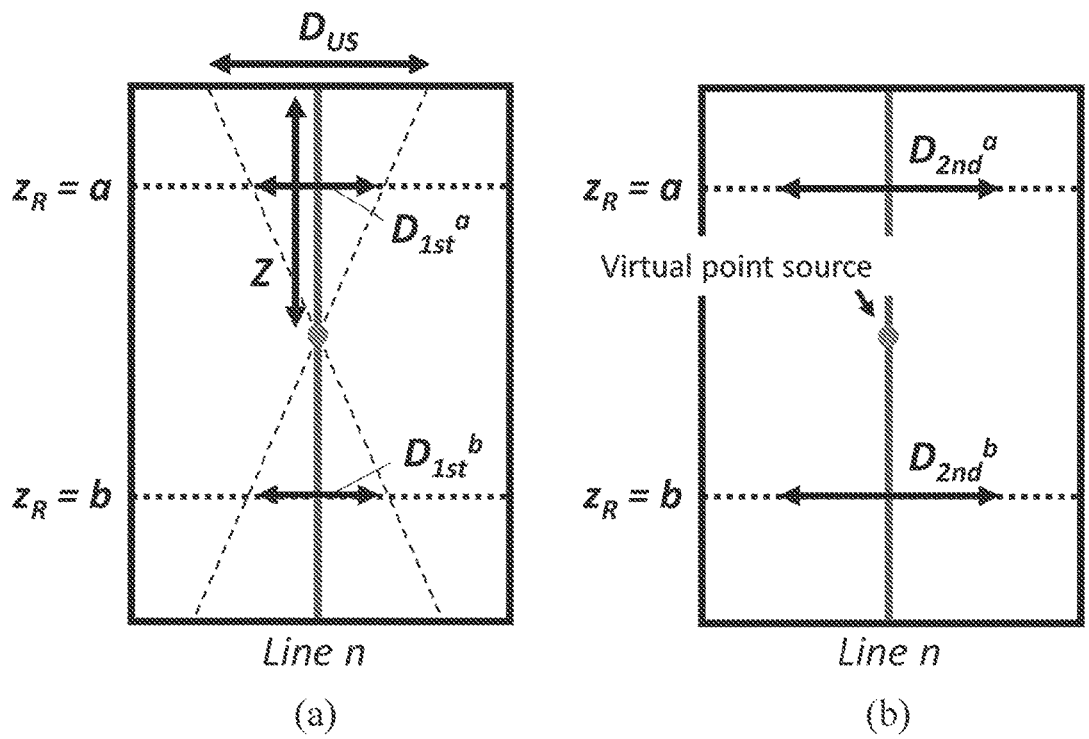
FIG. 32 shows the beamforming geometry when line n is beamformed.

The aperture size of the system is determined by both fixed focusing and following second SA beamforming. For the fixed focusing, the effective aperture size in the first focusing is affected by the aperture size used in fixed focusing and fixed focusing depth because the geometrical region covered in FIG. 32 can be considered as the effective beamforming region. FIG. 32 shows the beamforming geometry when line n is beamformed. In the left-hand figure, the effective aperture size of the first beamforming is defined as $D_{1st}^a$ and $D_{1st}^b$ when $z_R = a$ and $z_R = b$ is chosen, respectively. In the right-hand figure, the effective aperture size of the second beamforming is defined as $D_{2nd}^a$ and $D_{2nd}^b$ when $z_R = a$ and $z_R = b$ is chosen.

The effective aperture size in the first ultrasound beamforming is $$D_{1st} = \frac{D_{US} F_{SA}}{z_F}, \tag{5.7}$$

and that in second beamforming is $$D_{2nd} = D_{SA}. \tag{5.8}$$

The overall effective aperture size is the smaller aperture in the first or the second beamforming. The overall effect on lateral resolution can be expressed as $$\text{Lateral Resolution} \propto \begin{cases} \dfrac{F_{SA}}{D_{1st}}, & \text{if } D_{2nd} < D_{1st} \\ \dfrac{F_{SA}}{D_{2nd}}, & \text{if } D_{2nd} \geq D_{1st} \end{cases}. \tag{5.9}$$

The SNR is another factor that represents the quality of beamforming formulated as [15]

$$SNR = 20 \cdot \log_{10}\left\{\frac{|I_{Max}|}{\sigma_{noise}}\right\}, \tag{5.10}$$

where $I_{Max}$ is the maximum signal amplitude, and $\sigma_{noise}$ is the RMS electrical noise level. The SNR of ultrasound signals depends on many factors including f-number, attenuation, reflection, and angle sensitivity of elements, etc. However, when all parameters except f-number are fixed, the SNR is determined based on f-number as $$SNR = f(F\#). \tag{5.11}$$

In the algorithm, therefore, equation (5.9) determines SNR as well as lateral resolution.

Optimum Aperture Size

The appropriate aperture size in the second synthetic aperture beamforming can be determined by the effective aperture size in the first ultrasound beamforming. Since the initial resolution is determined by the aperture size used for fixed focusing, the coherent signals are mainly contained at certain range of the aperture size used in fixed focusing. We can use this information to determine the aperture size for the synthetic aperture beamforming. Therefore, we defines the aperture size for the synthetic aperture beamforming as $$K(z_R) = \frac{(|z_R - z_F|)D_{US}}{z_F}. \tag{5.12}$$

When the SNR of the signals is extremely low, however, the reconstructed image may contain a noise-originated gradation artifact as the number of summation is inhomogeneous for each focal point. Hence, the beamforming utilizing full aperture should be more appropriate in this case.

Methods

Simulation Setup

Five photoacoustic point sources were placed at 10 mm, 20 mm, 30 mm, 40 mm, and 50 mm depth, respectively to observe the proposed re-beamforming effect corresponding different target depths. The acoustic response was created using Field II [16]. The center frequency of the impulse response was set to 2 MHz. A 128 elements with 0.3 mm pitch linear array transducer were assumed as a receiver. The received signals were sampled at 40 MHz. Beamforming with a fixed focus point and dynamic focusing was applied to the simulated channel data created using Field II, and the second re-beamforming algorithm is applied on that data. We varied the following parameters based for the purpose of the evaluation: the fixed focusing depth, SA beamforming focusing depth, fixed focusing aperture size, and aperture size for the second synthetic aperture beamforming. As the control of the resolution with this setup, the conventional delay-and-sum PA beamforming algorithm is applied on the simulated channel data. Full-width at a half maximum (FWHM) is used as a metric to evaluate the resolution of beamforming algorithm. For SNR analysis, −20 dB Gaussian noise compared to the maximum intensity is added to the background, and the SNR is computed using equation (5.10).

Experiment Setup

The experimental setup is shown in FIG. 13. A 905 nm wavelength pulsed laser diode was used irradiate a plastisol phantom with black ink. The diode laser is triggered by a function generator which is programmed through a PC. Since the light was absorbed by the surface of the phantom because of the high absorption coefficient of the black ink, PA signals could be generated from a tiny spot in the phantom, which could be regarded as a point source. The generated PA was received by a 0.3 mm pitch 128 elements linear array ultrasound transducer. The received channel data was transferred to a channel data collection device (DAQ) via clinical ultrasound machine (Sonix Touch, Ultrasonix), and saved to the PC. Beamforming algorithms are applied to the collected channel data.

Results

Resolution Evaluation

Figure 33:
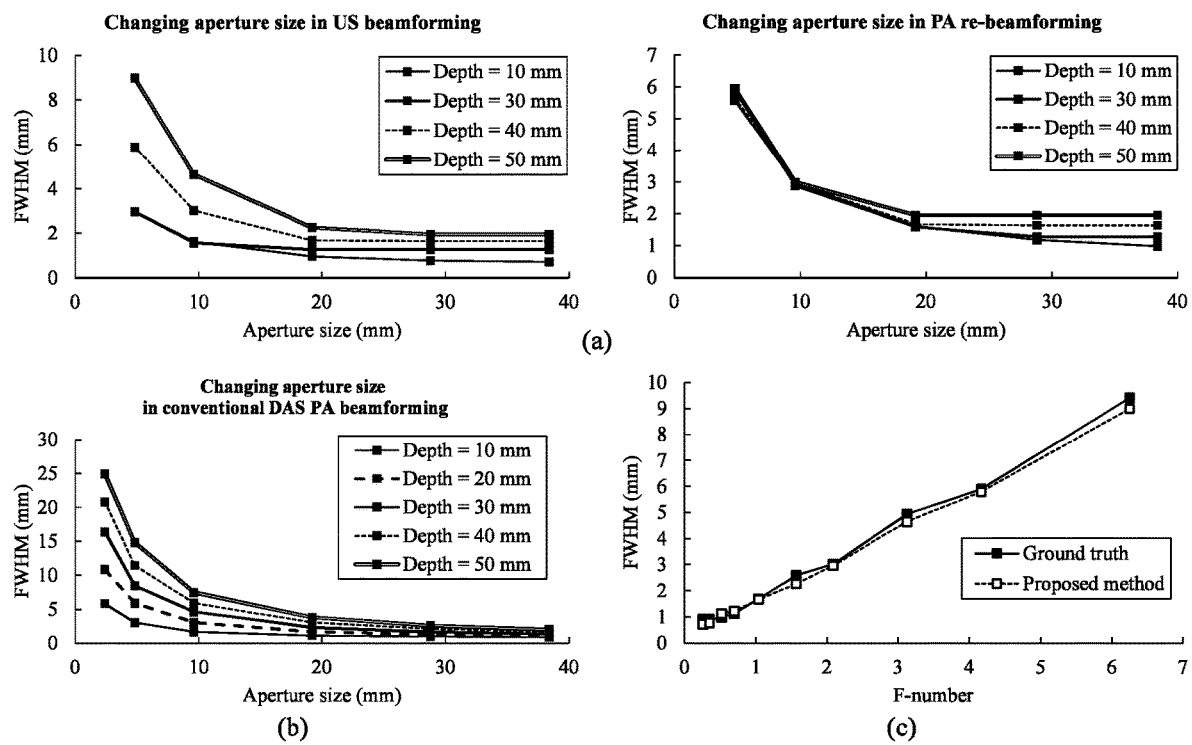
FIG. 33 shows the FWHM of the proposed re-beamforming for the designated focusing depth, and varying the aperture size.

To quantitatively validate the performance of the propose PASA beamformer, the resolution of reconstructed point targets should be compared to the theoretical property introduced above. As the first step, we analyzed the FWHM of the PA reconstructed point with conventional delay-and-sum PA beamformer at each depth and with different aperture size, in that the resolution of the point targets is depending on simulation conditions. FIG. 33 shows the FWHM of the proposed re-beamforming for the designated focusing depth, and varying the aperture size in the first beamforming (top left) and the second beamforming (top right). FIG. 33 also shows the ground truth FWHM results using a delay-and-sum algorithm with dynamic focusing (bottom left), and the focusing depth and aperture size parameters in top left, top right, and bottom left plots were compressed into the metric of f-number (bottom right). The theoretical ground truth values were computed by fitting the ground truth data from the bottom left plot into equation (5.9).

In this simulation, whole elements information is used for the PA beamforming to estimate the maximum achievable resolution in this setting. The trend of FWHM reduction could be seen as the target depth decreases and the aperture size increases (FIG. 33, bottom left). Then, the FWHM performance is evaluated through f-number, which is a more universal metric integrating the essence of both aperture size and focusing depth. For this data, the combination of depth and aperture size was found for each f-number, and we computed the average of FWHM values for the corresponding f-number (FIG. 33, bottom right). This result is used as the ground truth control to tell the resolution under certain f-number.

Then, the FWHM of re-beamformed result using ultrasound beamformed data with a single focus point is measured. The aperture size was varied in the first fixed focus ultrasound beamforming and the second beamforming. To focus on the effect of each beamforming process, when the first beamforming aperture is varied, the second beamforming aperture is the full elements. Similarly, when the second beamforming aperture is changed, maximum available aperture size is used in the first beamforming. The result of measured FWHM is plotted in the top plots in FIG. 33. The top left of FIG. 33 is the result that the aperture size of the first ultrasound beamforming is varied, and the top right of FIG. 33 shows the FWHM reduction due to the aperture size increase in the second beamforming. Although the raw results in the top plots of FIG. 33 were hard to be compared to the theoretical values, those results could be compared through the metric of f-number. Therefore, we rearranged data based on the f-number from different depth and aperture size, the FWHM value in each f-number was used to compare to that of the theoretical value which was represented by the bottom left plot of FIG. 33. The bottom right plot of FIG. 33 shows the comparison result for different f-number and target depth. The result demonstrated that the simulated resolution in re-beamforming agrees well with the theoretical. When quantitatively comparing two data sets in the bottom right plot of FIG. 33, the correlation coefficient was 99.87%. Hence, the simulation successfully demonstrated the validity of the resolution property of proposed beamformer.

SNR Evaluation

Figure 34:
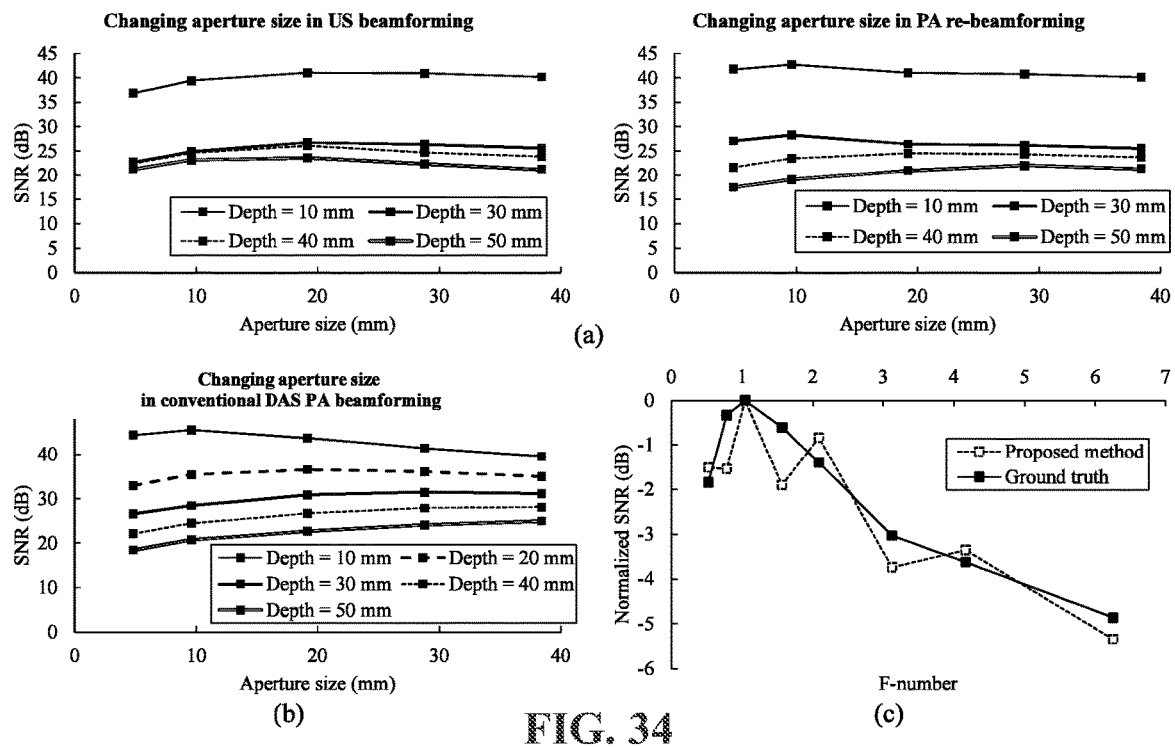
FIG. 34 shows the measured SNR of proposed beamformer varying the aperture size.

Following the evaluation scheme used above, the SNR of beamformed data using conventional PA beamformer and proposed re-beamforming algorithm were calculated using equation (5.10). FIG. 34 shows the measured SNR of proposed beamformer varying the aperture size in the first beamforming (top left) and the second beamforming (top right). The other aperture size was fixed to be maximum when one beamformer aperture size was changed. FIG. 34 also shows the ground truth SNR results using a delay-and-sum algorithm with dynamic focusing (bottom left). FIG. 34 shows how the focusing depth and aperture size parameters in the other plots were compressed into the metric of f-number (bottom right). To compensate the SNR variance for the same f-number but different target depth, the SNR of f-number 1.04 was normalized to be 0 dB. The theoretical ground truth values were computed by fitting the ground truth data from the bottom left plot in FIG. 34 into equation (5.9).

The ground truth data was taken using conventional DAS PA beamforming by changing the aperture size and the focusing depth (FIG. 34, bottom left). For the proposed method, the aperture size was changed at either the first and second beamformer, while the other aperture size was fixed to be the maximum aperture size (FIG. 34, top). One difference of SNR compared to resolution is that the SNR is not proportional to the f-number as other factors, especially attenuation difference at different depth, also affect the SNR. Therefore, it is not possible to reorganize the results shown in FIG. 34, top plots and bottom left plot simply based on f-number as done in resolution analysis (FIG. 33, bottom right). To observe the characteristics of SNR for corresponding f-number, the SNR at f-number of 1.04 was normalized to be 0 dB throughout different target depth results. The processed result for proposed results and theoretical results are shown in FIG. 34, bottom right plot. Although it was not as stable as resolution due to the effect of multiple factors affecting SNR, a shared trend could be seen between the proposed method and theoretical values. The correlation coefficient of them were 91.56%.

PA Re-Beamforming for Dynamically Focused US Beamformed RF Data

Figure 35:
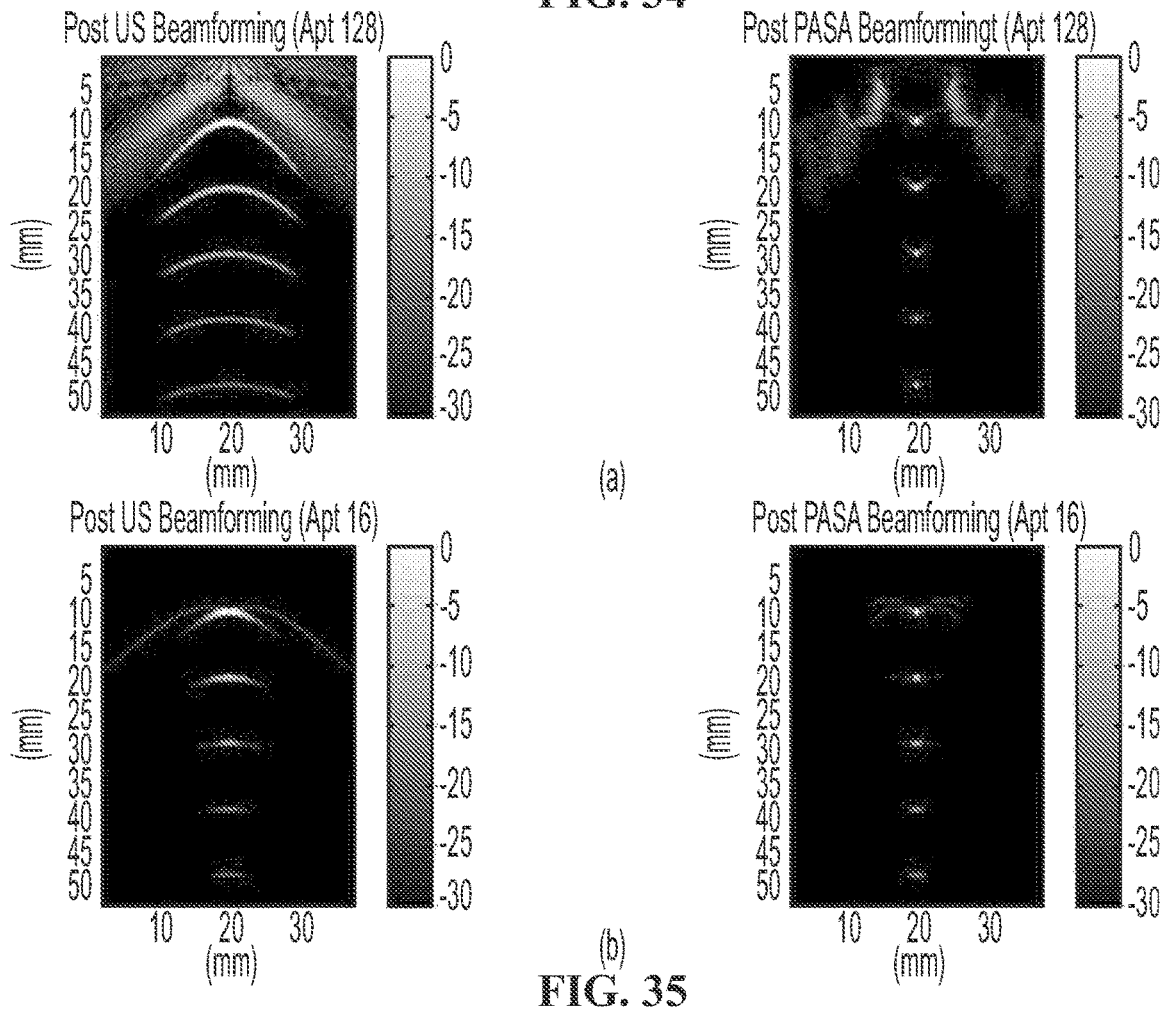
FIG. 35 shows the reconstructed results of SA beamforming using dynamically focused ultrasound beamformed RF data.

FIG. 35 shows the reconstructed results of SA beamforming using dynamically focused ultrasound beamformed RF data. The defocused ultrasound beamformed data could be re-beamformed through PASA beamforming. The aperture size for $1^{st}$ ultrasound beamforming is changed from 128 elements (left-hand plots) to 16 elements (right-hand plots). The point targets in ultrasound beamforming were not only degraded due to wrong delay function, but the large grating lobe is also appeared in the near field when a large aperture is used in ultrasound beamforming. This Grating lobe artifacts remain in SA beamforming result (left-hand plots). When a smaller aperture is used in US beamforming, the grating lobe artifacts were reduced, and it is less visible in the PASA beamforming result (right-hand plots). On the other hand, when a small aperture size is used, the resolution in deep region is degraded compared to that with a large aperture. Thus, in the practical implementation, it is suggested to find an appropriate aperture size in the first ultrasound beamforming to prevent grating lobe from showing up. For instance, f-number could be fixed throughout the image to keep small aperture size in the near region while large aperture size is applied in the far region.

Experimental Evaluation

The ultrasound beamforming with fixed focusing and dynamic focusing is applied on the channel data to produce two types of ultrasound post-beamformed data. The SA re-beamforming results from ultrasound beamforming with a single focal point are shown in FIG. 36. The point source could be reconstructed for all fixed focus in the range of 3 mm to 45 mm. The FWHM and SNR of the point source is measured, and it is plotted for different fixed focusing depth in FIG. 36, lower plots. The result of conventional PA beamforming is also shown as control and its FWHM and SNR are shown as conventional. This result can be regarded as the lower boundary because the maximum available aperture information is used in the control case. The FWHM of the fixed focusing until around 9 mm to 21 mm was nearly close to that of control data. The point source is located around 12 mm depth, and when the fixed focusing depth applied was far from the target, the reconstructed point got extended in the lateral direction. This is due to insufficient f-number through the first and the second beamforming.

In term of SNR, a similar trend of image quality improvement was observed compared to lateral resolution analysis in the range until 8 mm. However, SNR was not degraded even if a deep focusing depth was taken. This is attribute the trend of SNR was not only related to the f-number, and the property makes the SNR trends to be relatively mild. In addition, the SNR for the depth over around 10 mm shows a better number compared to the conventional beamformer, because the noise could cancelled more than the conventional PA beamforming during twice beamforming.

FIG. 37 shows the PASA beamforming results from dynamically focused ultrasound beamforming. The defocused target in ultrasound post-beamformed result could be focused again through PASA beamforming.

Discussion

High PRF laser system can be considered as a requirement on the system. Since the ultrasound post-beamformed RF data acquisition relies on clinical ultrasound system, it is necessary to synchronize the laser transmission to ultrasound line transmission trigger. To keep the frame rate similar to that of conventional ultrasound B-mode imaging, the pulse repetition frequency (PRF) of the laser transmission should be the same as the transmission frequency. Therefore, a high PRF laser system such as a laser diode is a desirable, similar to that used herein.

The proposed synthetic aperture beamforming utilizing fixed focusing data is also applicable to PA tomogram formation using hydrophone combined with an acoustic lens with a focal point as proposed by M. L. Li et al. [16]. Hydrophone is widely used as a PA signal receiver because of its wide frequency receiving capability and sensitivity compared to clinical ultrasound array [17]. PA tomogram can be formed by sweeping the hydrophone using a Cartesian stage. Wider diameter of elements has higher sensitivity, but those hydrophone is hard to achieve high lateral resolution because of wide reception angles [18]. Attaching an acoustic lens is an easy solution to provide a focus, but the high resolution is only applicable near the focal point, and the image is defocused outside of the focal point. The acoustic lens focuses the acoustic beam for a single depth, which is the same situation for the fixed beamformed data using a linear array. Thus, the proposed algorithm could be a solution to provide an opportunity to generate a dynamically focused PA tomogram by beamforming received data.

REFERENCES—EXAMPLE 5

[1] M. Xu and L. V. Wang, "Photoacoustic imaging in biomedicine," Rev. Sci. Instrum., 77, 041101 (2006).

[2] Park S., Aglyamov S.R., and Emelianov S., "Beamforming for photoacoustic imaging using linear array transducer," Proc. in IEEE Int. Ultrasonics Symp., pp. 856-859 (2007).

[3] B. Yin, D. Xing, Y. Wang, Y. Zeng, Y. Tan, Q. Chen, "Fast photoacoustic imaging system based on 320-element linear transducer array," Phys. Med. Biol., 49(7), 1339-1346 (2004).

[4] C. K. Liao, M. L. Li, and P. C. Li, "Optoacoustic imaging with synthetic aperture focusing and cohehrence weighting," Optics Letters, 29, 2506-2508 (2004).

[5] R. G. M. Kolkman, P. J. Brands, W. Steenbergen, T. G. V. Leeuwen, "Real-time in vivo photoacoustic and ultrasound imaging", J. Biomed. Opt., 13(5), 050510 (2008).

[6] J. J. Niederhauser, M. Jaeger, and M. Frenz, "Comparision of laser-induced and classical ultrasound," Proc. SPIE, 4960, 118-123 (2003).

[7] N. Kuo, H. J. Kang, D. Y. Song, J. U. Kang, and E. M. Boctor, "Real-time photoacoustic imaging of prostate brachytherapy seeds using a clinical ultrasound system," J. Biomed. Opt., 17(6), 066005 (2012).

[8] H. J. Kang, N. Kuo, X. Guo, D. Song, J. U. Kang, E. M. Boctor, "Software framework of a real-time pre-beamformed RF data acquisition of an ultrasound research scanner", Proc. of SPIE, 8320, 83201F (2012).

[9] T. Harrison and R. J. Zemp, "The applicability of ultrasound dynamic receive beamformers to photoacoustic imaging," IEEE Trans. Ultrason. Ferroelectr. Freq. Control, 58(10), 2259-2263 (2011).

[10] C. H. Frazier and W. D. O'Brien, "Synthetic aperture techniques with a virtual source element," IEEE Trans. Ultrason., Ferroelec., Freq. Contr., 45, 196-207 (1998).

[11] S. I. Nikolov and J. A. Jensen, "Virtual ultrasound sources in high resolution ultrasound imaging," Proc. SPIE, Progress in biomedical optics and imaging, 3, 395-405 (2002).

[12] J. Kortbek, J. A. Jensen, K. L. Gammelmark, "Synthetic Aperture Sequential Beamforming," Proc. in IEEE Int. Ultrasonics Symp., 966-969 (2008).

[13] K.E. Thomenius, "Evolution of Ultrasound Beamformers," Proc. IEEE Ultrasonics Symp, 2, 1615-1622 (1996).

[14] K. F. Üstüner and G. L. Holley, "Ultrasound imaging system performance assessment," presented at the 2003 American Association of Physicists in Medicine Annu. Meeting, San Diego, Calif., (2003).

[15] J. A. Jensen, N. B. Svendsen, "Calculation of pressure fields from arbitrarily shaped, apodized, and excited ultrasound transducers," IEEE Trans. Ultrason., Ferroelec., Freq. Contr., 39, 262-267 (1992).

[16] M. L. Li, H. F. Zhang, and K. Maslov, "Improved in vivo photoacoustic microscopy based on a virtual-detector concept," Optics Letters, 31, 474-476 (2006).

[17] Y. Tsunoi, S. Sato, R. Watanabe, S. Kawauchi, H. Ashida, and M. Terakawa, "Compact acoustic-resolution photoacoustic imaging system with fiber-based illumination", Jpn. Journal of Applied Physics, 53(12), 126701 (2014).

[18] H. K. Zhang, K. Kondo, M. Yamakawa, T. Shiina, "Coded excitation using periodic and unipolar M-sequences for photoacoustic imaging and flow measurement", Optics Express, 24(1), 17-29, (2016).

EXAMPLE 6

Out of Plane Tool Tracking

Figure 38:
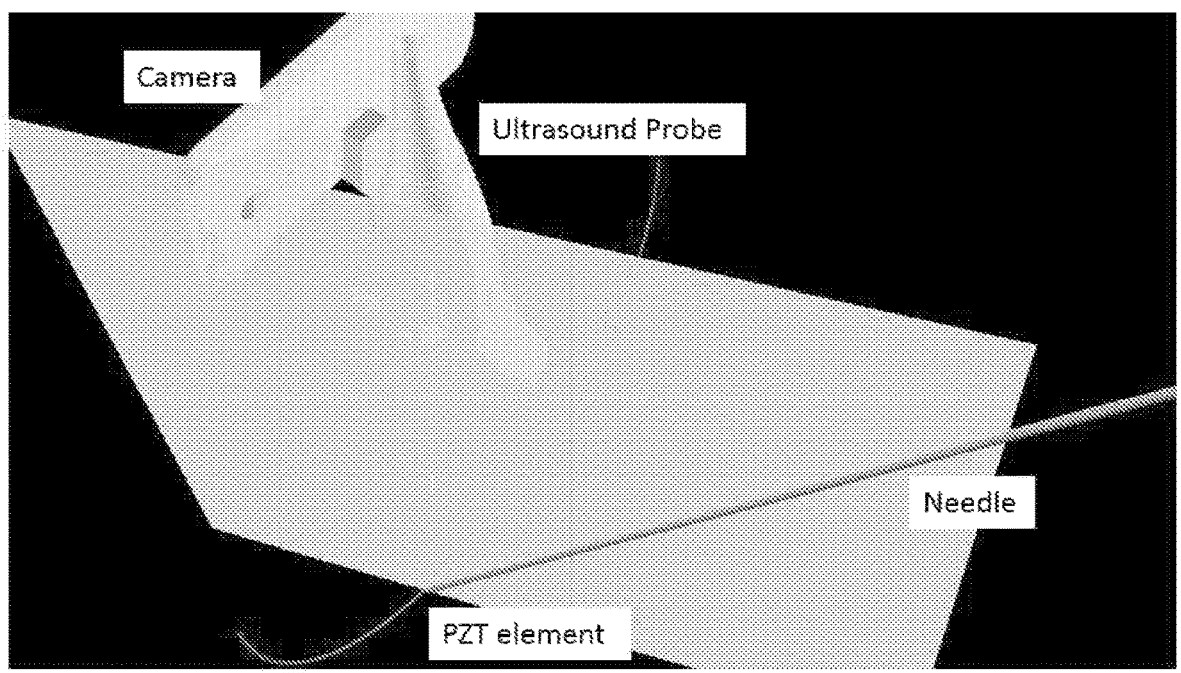
FIG. 38 illustrates a monocamera attached to an ultrasound probe that observes the needle shaft.

A monocamera attached to the ultrasound probe observes the needle shaft, as shown in FIG. 38. The needle shaft and the camera's optical center define a plane that the needle and its tip lie on. A PZT element at the tip of the needle transmits a signal that the ultrasound probe receives. This signal can be used to define a circular arc that the needle tip lies on. The intersection of these two geometrical loci result in the 3D location of the PZT element at the needle tip.

Figure 39:
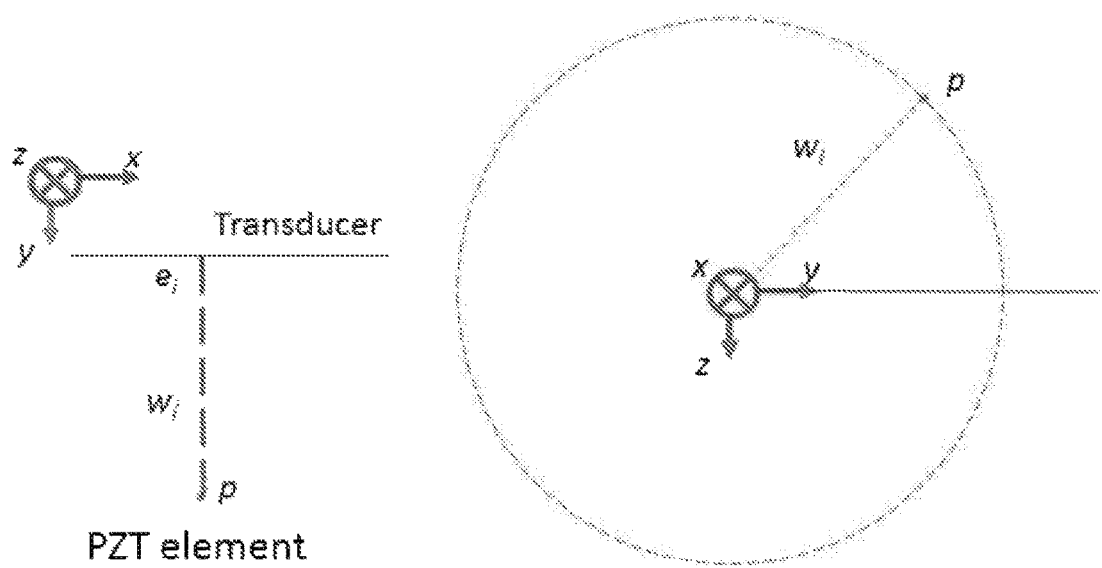
FIG. 39 illustrates how the signal transmitted by the PZT element and received by the ultrasound transducer can be used to determine the shortest time of flight between the PZT element and the transducer.

The signal transmitted by the PZT element and received by the ultrasound transducer can be used to determine the shortest time of flight between the PZT element and the transducer. This concept is illustrated in FIG. 39. Given that the ultrasound transducer is a linear array, a circular arc exists where any point on it will have the same time of flight.

Figures 40, 41:
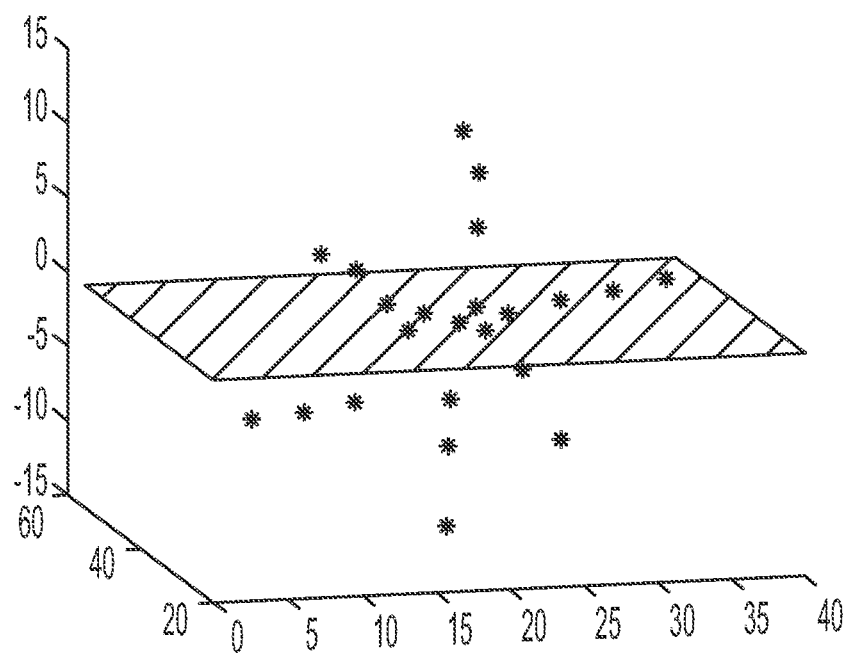
FIG. 40 shows a computed localization result.
FIG. 41 comprises a table showing the precision of the computed result compared to the known motions.

We placed a needle tip at known locations. FIG. 40 shows the computed localization result. The table in FIG. 41 shows the precision of the computed result compared to the known motions.

EXAMPLE 7

Ultrasound Needle Detection Using Mobile Imaging

There is a need for intraoperative tracking of surgical tools, specifically the tracking of pieces such as needle tips while inside the patient's body. A method was developed to localize a needle-tip using a combination of ultrasound (US) imaging and conventional camera images. The goal of the project is to detect and track tools intraoperatively.

Figure 42:
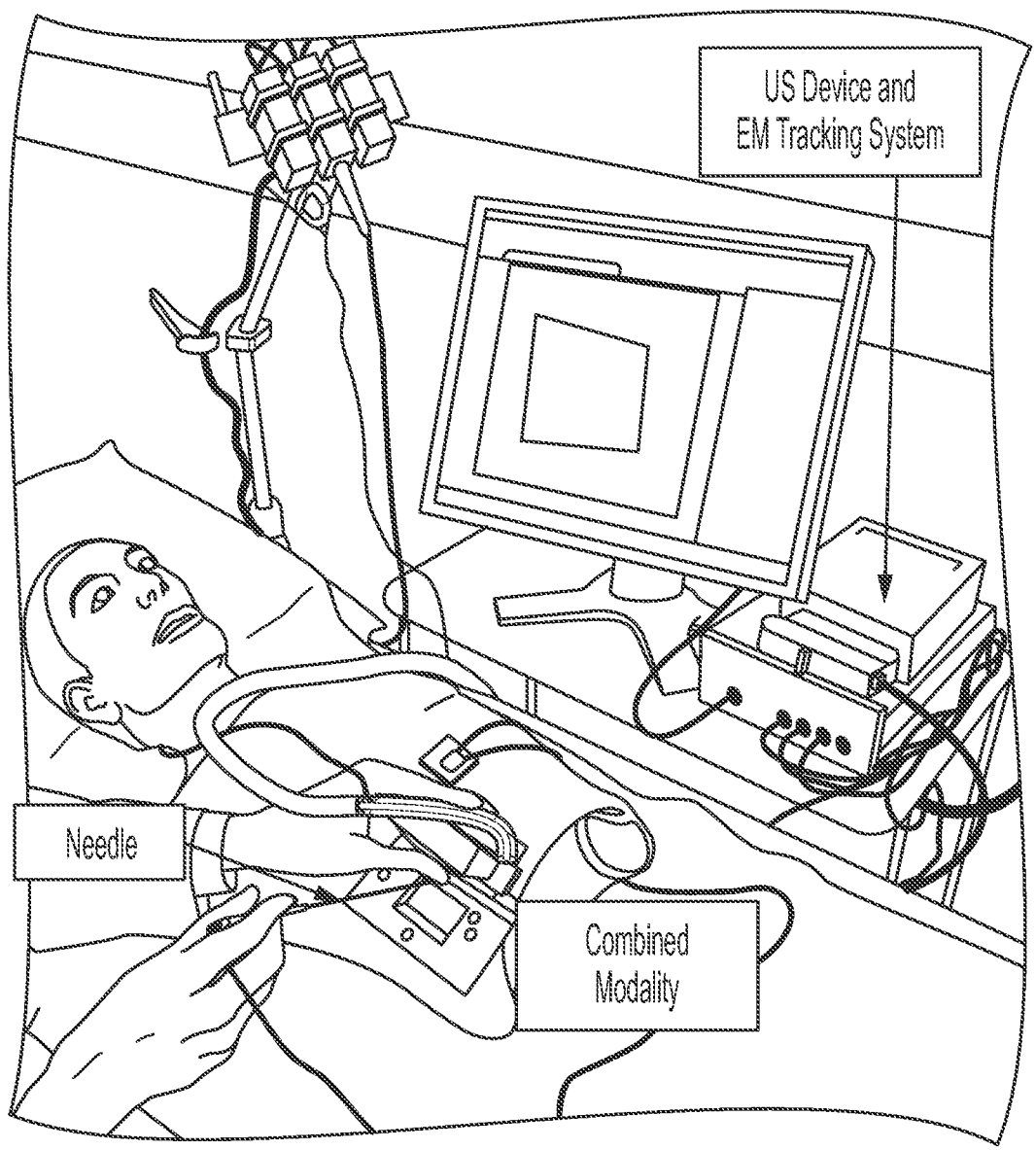
FIG. 42 illustrates conventional electromagnetic tracking-based methods to provide intraoperative needle-tip tracking.

Needle-tip tracking allows the surgeon to more accurately reach their designated target and more safely perform their surgical task. US image-based and Electromagnetic tracking-based methods are two conventional methods to provide intraoperative needle-tip tracking (FIG. 42). Both of these methods have problems. US images have a limited field of view and cannot track needle-tips that are outside its imaging plane. Electromagnetic tracking-based methods require integrating additional hardware into the surgical workspace.

Solution

Figure 43:
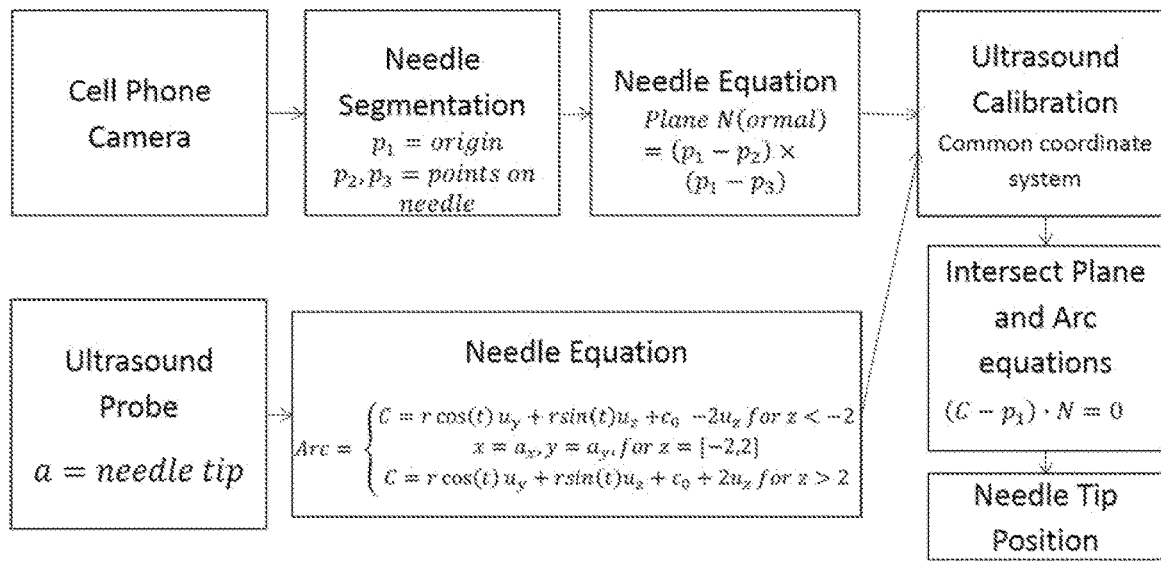
FIG. 43 shows a workflow diagram for detecting a needle's position according to some embodiments of the invention.

An active piezoelectro (PZT) element is attached to the tool tip, transmitting synchronized pulses to the receiving US transducer. These received pulses give us: the transducer element closest to the PZT element, the distance between this transducer element and the PZT element. This information can be used to generate a subset of positions (arc) where the PZT element may lie with respect to the ultrasound image. A camera is attached to the US transducer, capturing an image of the external portion of the needle. This image gives us a plane that the needle lies on and that intersects with the camera. By transforming the plane and the arc into the same coordinate system using a pre-computed ultrasound calibration, one can then compute the intersection of the plane and the arc. In most cases, there will be a single intersection point indicating the position of the PZT element or needle-tip. A workflow diagram according to some embodiments of the invention is shown in FIG. 43.

System Setup

Figure 44:
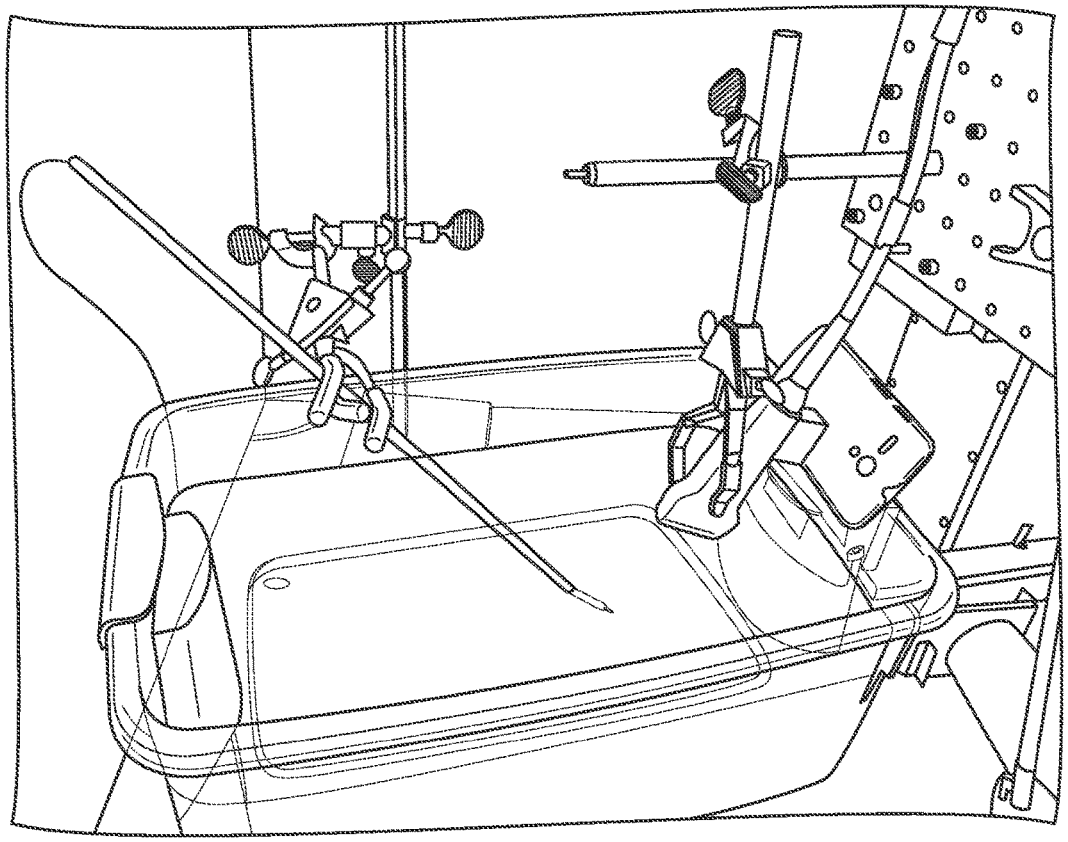
FIG. 44 shows how a needle with US emitting tip was fixed in two different poses while a cell phone mounted US probe was moved in linear 4 mm steps.
Figure 45:
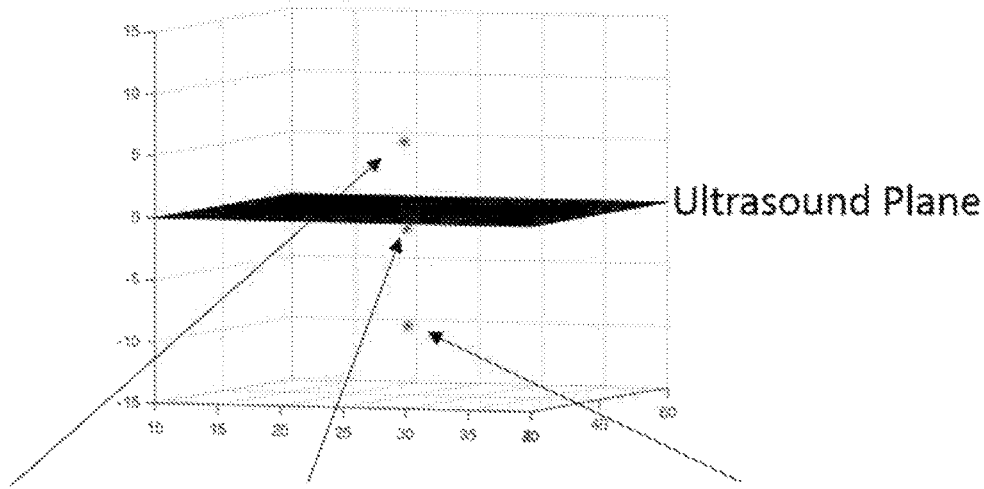
FIG. 45 shows tables displaying tracking results.
Figure 46:
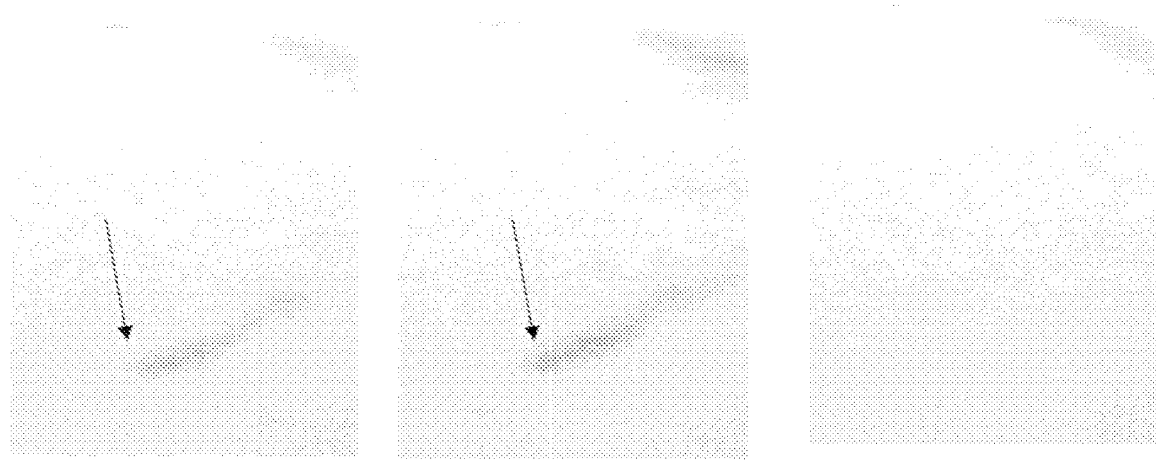
FIG. 46 shows an example of three positions of the needle in inverted B-Mode imaging (below) compared the positions obtained by our method (above)

A "needle" with US emitting tip was fixed in two different poses while a cell phone mounted US probe was moved in linear 4 mm steps in the three orthogonal directions independently (FIG. 44). Accuracy was measured by how out-of-plane computed points were that were experimentally placed in-plane. Precision was measured by the relative distance between two calculated points compared to the known distance (4 mm). Results are shown in the tables in FIG. 45. FIG. 46 shows an example of three positions of the needle in inverted B-Mode imaging (below) compared the positions obtained by our method (above). Notice the left and center images look similar on B-Mode images, and the right image is not visible at all. The position of the needle with respect to the US probe as it is moved is shown in FIG. 40.

EXAMPLE 8

Photoacoustic Image Reconstruction from Ultrasound Post-Beamformed B-Mode Image

A photoacoustic (PA) image is constructed by beamforming received channel data, and then applying signal processing methods to display it [1, 2]. Although acquiring channel data is essential, most clinical ultrasound systems do not offer an interface to obtain the synchronized channel data. Accessing these synchronized channel data requires expensive and sometimes bulky research systems such as DAQ system, and it is an obstacle to translate the PA imaging technique into clinical applications. Therefore, to broaden the impact of PA imaging, we investigate PA image reconstruction algorithm using the data accessible at clinical ultrasound systems. As clinical ultrasound systems have been widely used all over the world, this work connects PA research to the environment in which specialized research systems do not exist.

Figures 47A, 47B:
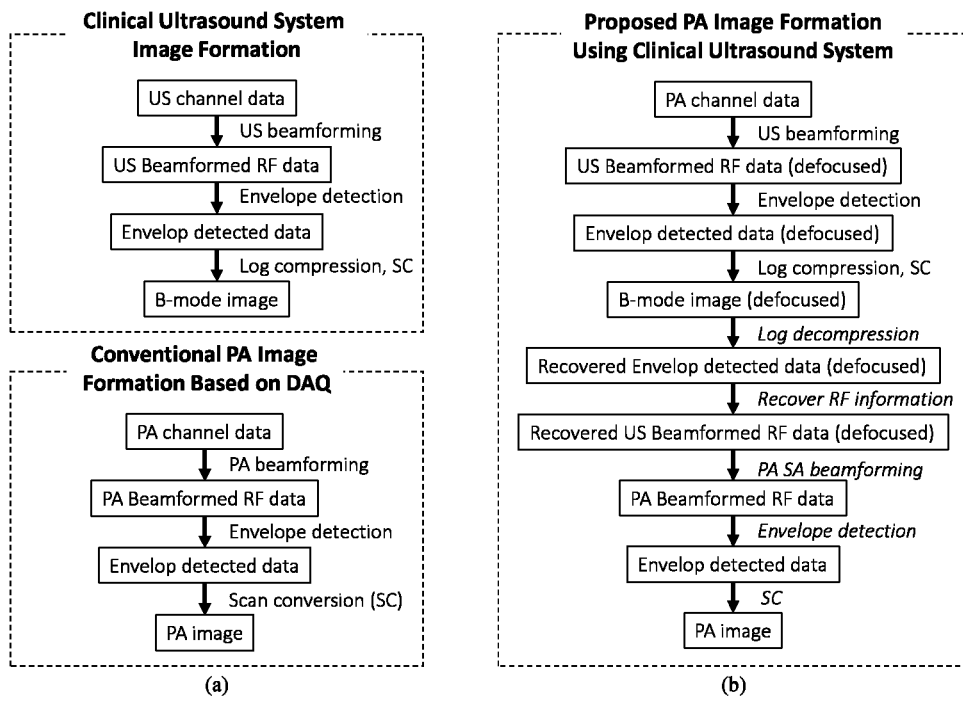
FIG. 47A illustrates conventional image formation in US and PA imaging.
FIG. 47B shows proposed PA image formation using B-mode image from clinical ultrasound systems.

Our previous work has demonstrated that the PA image reconstruction can be carried out from US beamformed RF data [3]. Nevertheless, the method requires clinical ultrasound system to have a functionality to provide a radio-frequency (RF) data. B-mode image, on the other hand, is the final product of ultrasound image, and accessible at most of the ultrasound systems. In this work, we present the possibility to recover US post-beamformed RF data from a B-mode image and re-beamform the recovered data to a PA image. Even though each vendor has its unique signal processing to form the final B-mode image, envelope detection and scan conversion including log compression are two major post processing after generating beamformed RF data. FIG. 47A illustrates the major signal processing for ultrasound image as well as PA image.

We divide the proposed approach into two major steps: 1) RF signal recovery from B-mode data, and 2) PA beamforming using US post-beamformed RF data. For the first step, the envelope data is recovered from B-mode image by applying log decompression. And since the RF information is discarded in the envelope data, we convolute an acoustic impulse response with the envelope data. For the second step, an adaptive PA beamforming algorithm is applied on US post-beamformed RF data. The US post-beamformed RF data is utilized as pre-beamformed RF data for PA re-beamforming, and the new delay function is used by taking into account that the focus depth in US beamforming is at the half depth of PA case. The stream of the proposed PA image formation is shown in FIG. 47B.

Retrieving US Post-Beamformed RF Data from B-Mode data

A B-mode image is the final output from clinical ultrasound systems, in which the envelope detected acoustic signals are displayed in log scale. Detail signal processing techniques to produce a B-mode image could vary depending on vendor, but envelope detection and following log compression are two basic common signal processing techniques after ultrasound beamforming. Therefore, reversing two signal processing steps is necessary to retrieve US post-beamformed RF data.

A general formulation of log compression is $$z_{ij} = \alpha \ln(y_{ij}) + \beta, \quad (8.1)$$

where $\alpha$ and $\beta$ are parameters indicating the contrast and brightness, respectively. $y_{ij}$ is the envelope detected data, and $z_{ij}$ is the observed intensity on a US B-mode image. Two parameters $\alpha$ and $\beta$ could be recovered by analyzing the speckle property of a B-mode image [4,5]. Thus, the estimated envelope detected data could be processed as $$\hat{y}_{ij} = e^{\left(\frac{z_{ij}-\beta}{\alpha}\right)}. \quad (8.2)$$

In contrast to log compression which is applied on the entire image, the envelope detection is applied to line by line. The beamformed RF signals of an A-line x(t) could be expressed as $$x(t) = y(t)\cos(2\pi f_0 + \phi), \quad (8.3)$$

where y(t) is the envelope data of the line, and $f_0$ and $\phi$ are its center frequency and phase, respectively. It is not difficult to multiple RF component to the envelope detected data, but the phase information will not be recovered. The phase information is essential to utilize the data for further PA beamforming, so that equation (8.3) is unavailable for the proposed method. Instead, we assumed the photoacoustic image as a collection of delta functions, and the RF component is added to each delta function through convolution.

$$\widehat{x(t)} = \Sigma_{s=1}^{S} y(t-s) H(s), \quad (8.4)$$

where H(s) is an impulse response that corresponding to a cycle of cosine function. $\widehat{x(t)}$ is the recovered US post-beamformed RF data, and will be used for PA be-beamforming.

Reconstructing PA Image from Ultrasound Post-Beamformed RF Data

Figure 48:
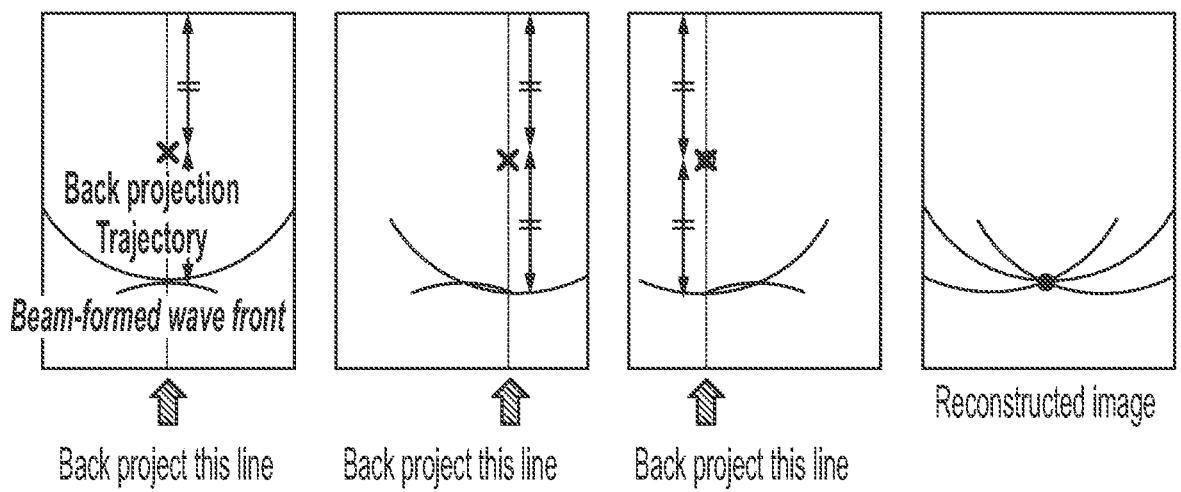
FIG. 48 shows an example of implementing an algorithm based on back projection.

The difference between ultrasound beamforming and PA beamforming is time-of-flight and accompanied delay function. Ultrasound beamforming takes into account the time-of-flight of the round trip of acoustic signals transmitted and received by the US probe elements, that is reflected at targets, while PA beamforming only counts one way trip from the PA source to the US probe. Therefore, the beamformed PA signals under ultrasound beamforming is defocused due to incorrect delay function. In our previous work, we proposed a synthetic aperture based PA beamformer using ultrasound post-beamformed RF data. Ultrasound beamformed RF data are considered as pre-beamformed input data, where its focal point is considered as a virtual element, and a new delay function is applied based on the acoustic wave travel starts from the virtual element [6-8]. Since, the delay function in dynamically focused ultrasound beamforming takes into account the round trip between the transmitter and the reflecting point, the focus point at each depth becomes the half distance for that in PA beamforming. Thus, it is possible to consider that the virtual point source is swept dynamically in the half distance of the true focal point. FIG. 48 shows an example of implementing proposed algorithm based on back projection.

Simulation and Experimental Setup

For simulation, five point targets were placed at the depth of 10 mm to 50 mm with 10 mm interval. A 6 cm linear array transducer with 128 elements were designed to receive the photoacoustic signals. Delay-and-sum with dynamic receive focusing was used to beamform the simulated channel data assuming ultrasound delay. Envelope detection and log compression were applied on the received data and proposed PA re-beamforming process was applied on the data.

Figure 49:
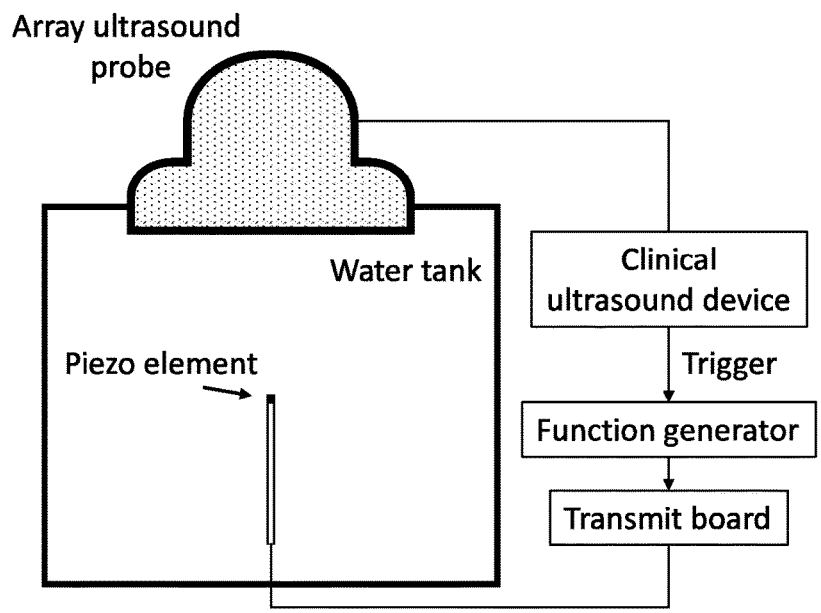
FIG. 49 shows an system setup according to some embodiments of the invention.

The system setup is shown in FIG. 49. Clinical ultrasound machine (Sonix Touch, Ultrasonix) was used to display and save the received data, and the acoustic wave transmission was turned off during receiving. A costum made piezo element was used to imitate a PA point target. The element has the center frequency of 10 MHz, and was attached to the tip of needle, and it was wired to an electric board controlling the voltage and transmission pattern. The acoustic signals transmission is triggered by the line generation trigger from clinical ultrasound machine. The received RF data was saved and a B-mode image was formed. All elements on the probe was used to beamform each line. The proposed signal processing was applied on the B-mode image.

Results

Figure 50:
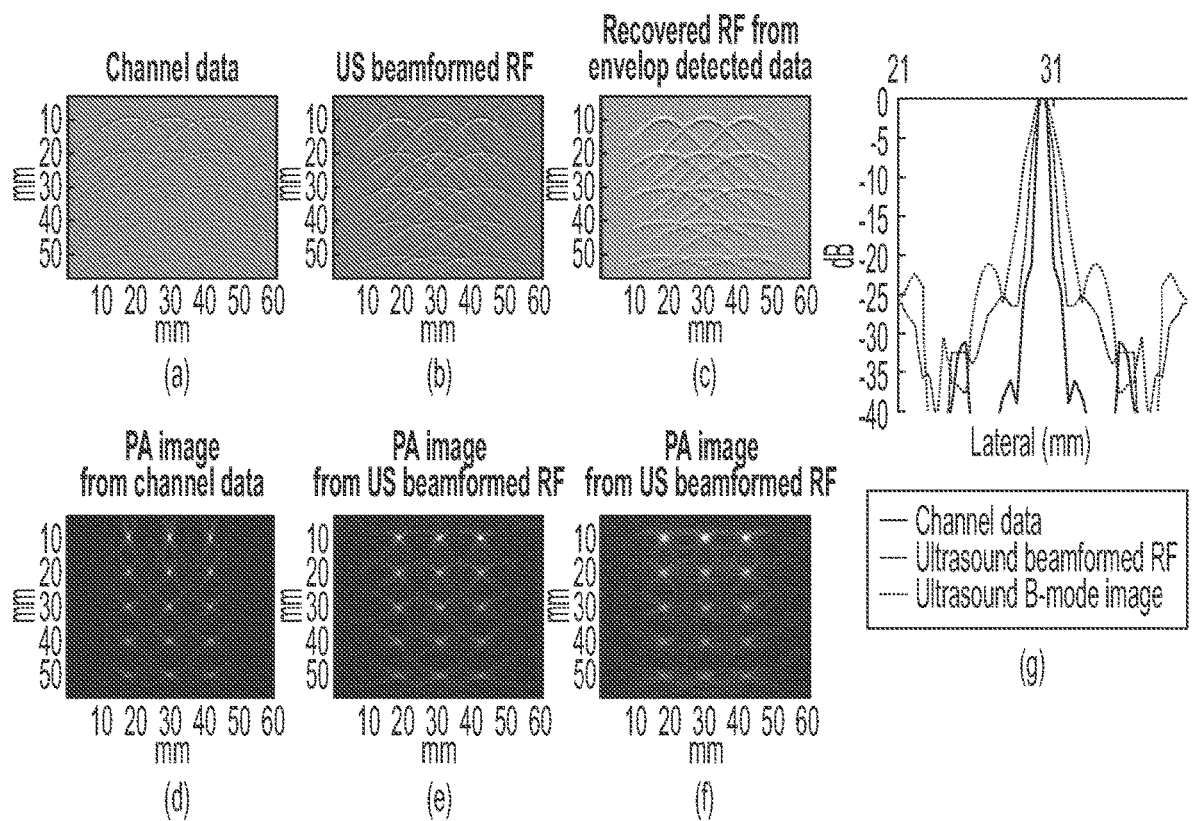
FIG. 50 shows a simulation result.

The simulation result is shown in FIG. 50. The input data of beamforming were shown in the top row and output was presented in the bottom row. The profile of a point located at 30 mm depth for three different input data was shown on the right. A set of channel data simulates PA signals was beamformed using delay-and-sum with dynamic receive focusing. The US beamformed RF data was defocused due to incorrect delay function (top row, middle plot). The US beamformed RF data could be re-beamformed to form a PA image using adaptive PA reconstruction algorithm (bottom row, middle plot). Then, a B-mode image was formed using the US beamformed RF data. We applied the log decompression and RF information recovery through convoluting a cycle of sine function. The RF component was lost through envelope detection, but new RF wave was added to the envelope detected data (top row, right plot). The recovered RF data was re-beamformed, and finally a PA image was obtained (bottom row, right plot). Although the reconstructed point was larger than the point reconstructed from channel data, it is demonstrated that the defocused data could be beamformed through proposed processing.

Figure 51:
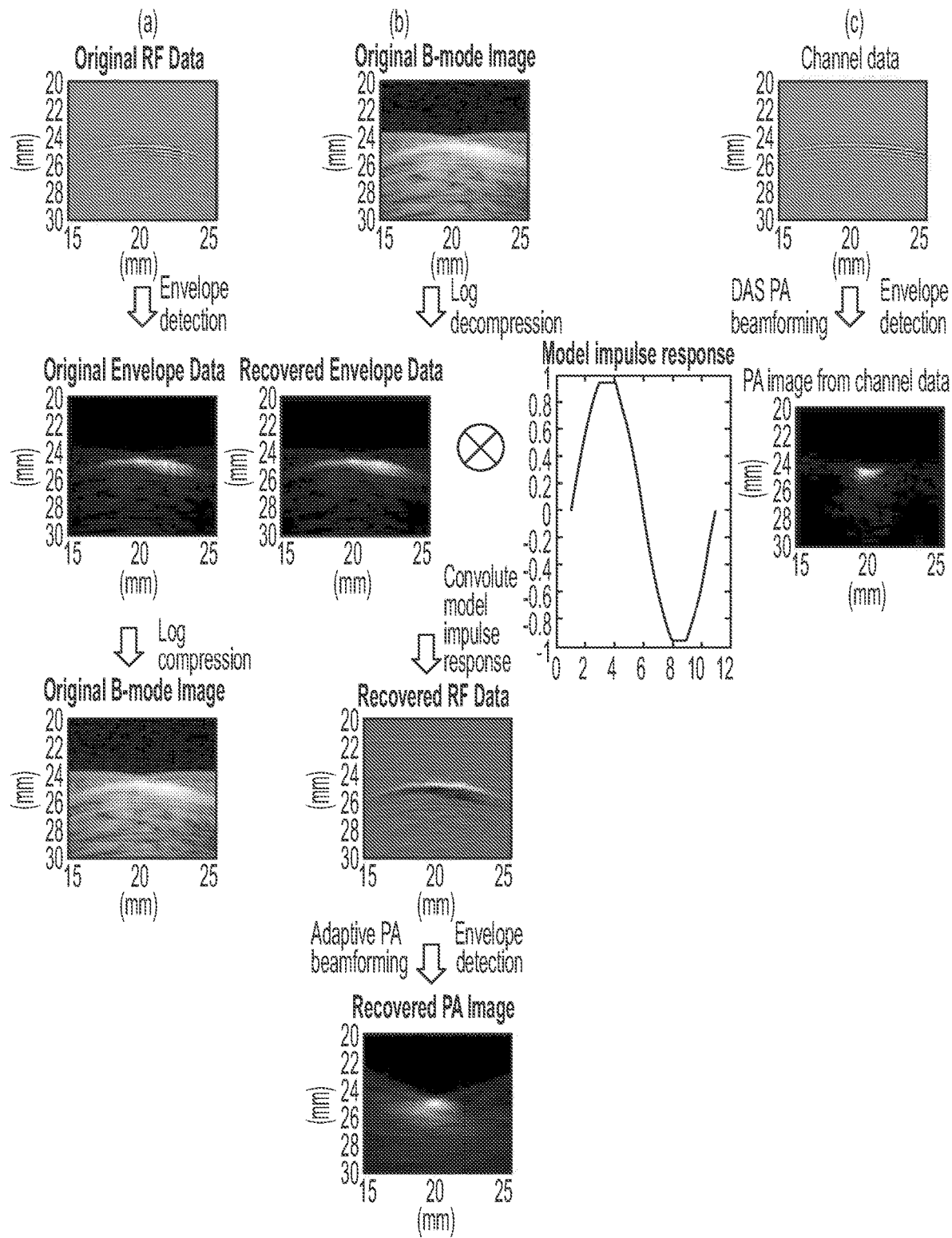
FIG. 51 shows an experimental result.

FIG. 51 shows the experiment results. The left-hand column illustrates US image formation in a clinical ultrasound system. The middle column shows PA image reconstruction processes. The right-hand column shows PA image reconstruction from channel data. A set of US post-beamformed RF data was collected from ultrasound machine, and a B-mode image is formed through envelope detection and scan conversion with log compression (left-hand column). The processed US B-mode image was used as the input for the proposed signal processing and following PA image re-beamforming. US post-beamformed RF data was recovered through convolution with a cycle of sine function, and finally a PA image is reconstructed using back projection based re-beamformer (middle column). For the control, the channel data was collected and conventional delay-and-sum PA beamforming was applied (right-hand column). The full width at half maximum (FWHM) of the US B-mode image was 7.50 mm, and it was improved to 1.89 mm through the proposed method. The FWHM for the PA image from the channel data was 1.48 mm. The degradation of point spread function could be due to signal loss during envelop detection, and blurring through convolution.

REFERENCES—EXAMPLE 8

[1] Park S., Aglyamov S.R., and Emelianov S., "Beamforming for photoacoustic imaging using linear array transducer," Proc. in IEEE Int. Ultrasonics Symp., pp. 856-859 (2007)

[2] Niederhauser J. J., Jaeger M., and Frenz M., "Comparision of laser-induced and classical ultrasound," Proc. SPIE, vol. 4960, pp. 118-123 (2003)

[3] H. K. Zhang, X. Guo, H-J Kang, and E. M. Boctor, Photoacoustic reconstruction using beamformed RF data: a synthetic aperture imaging approach", in Proceedings of SPIE, 9419, 94190L, (2015)

[4] Seabra, Jose, and Joao Sanches. "Modeling log-compressed ultrasound images for radio frequency signal recovery." 30th Annual International Conference of the IEEE, Engineering in Medicine and Biology Society (EMBS 2008). 2008.

[5] Prager, R. W., A. H Gee, G. M Treece, L. H Berman, "Decompression and speckle detection for ultrasound images using the homodyned k-distribution." Pattern Recognition Letters 24.4 (2003): 705-713.

[6] Frazier C. H. and O'Brien W. D., "Synthetic aperture techniques with a virtual source element," IEEE Trans. Ultrason., Ferroelec., Freq. Contr., 45:196-207 (1998)

[7] Nikolov S. I. and Jensen J. A., "Virtual ultrasound sources in high resolution ultrasound imaging," Proc. SPIE, Progress in biomedical optics and imaging, volume 3, pages 395-405 (2002)

[8] Kortbek J., Jensen J. A., Gammelmark K. L., "Synthetic Aperture Sequential Beamforming," Proc. in IEEE Int. Ultrasonics Symp. (2008)

[9] A. Cheng et al., Direct 3D ultrasound to video registration using photoacoustic markers, J. Biomed. Opt. 18(6), 066013 (2013)

[10] Muyinatu A. Lediju Bell, Nathanael P. Kuo, Danny Y. Song, Jin Kang, Emad M. Boctor, "In vivo visualization of prostate brachytherapy seeds with photoacoustic imaging," J. Biomed. Opt., 19(12):126011, 2014.

EXAMPLE 9

Figure 52:
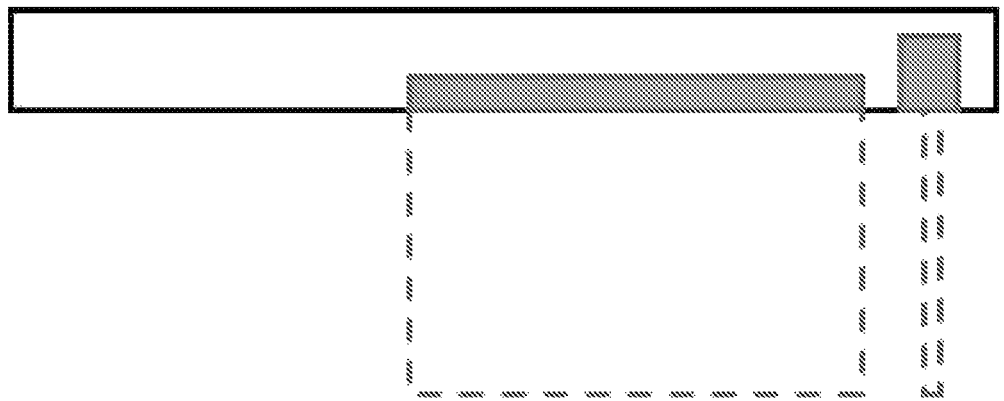
FIG. 52 shows ultrasound imaging planes with respect to bi-plane transrectal transducer.

Ultrasound to Video Registration using a Bi-Plane Transrectal Probe with Photoacoustic Markers—Active Point Localization with a Transrectal Transducer Before we begin describing the method for localizing the active point with respect to the transrectal transducer, we must describe the transducer itself. Bi-plane transrectal transducers typically have two imaging planes, one parallel and one perpendicular to its insertion axis. The parallel imaging plane is generally from a linear array and the perpendicular imaging plane is generally from a convex array. FIG. 52 is an example of such a transducer, where the dotted lines correspond to the imaging planes.

The key idea that enables our approach is the use of an active point. When using an active point, the channel data will be able to capture data even if the point is outside of the probe imaging plane. For example, in the scenario shown in FIG. 53 where the point represents an active point, both of the transducer arrays will receive a signal from the active point.

Since we are looking at active points, its position in the beamformed image must be interpreted in a different manner than a typical pulse-echo ultrasound image. While we can still trust the lateral position of the point in the image, the axial position now contains an elevational component as well. Having two arrays with a known transformation between them allows us to recover and separate the axial and elevational components.

Figure 53:
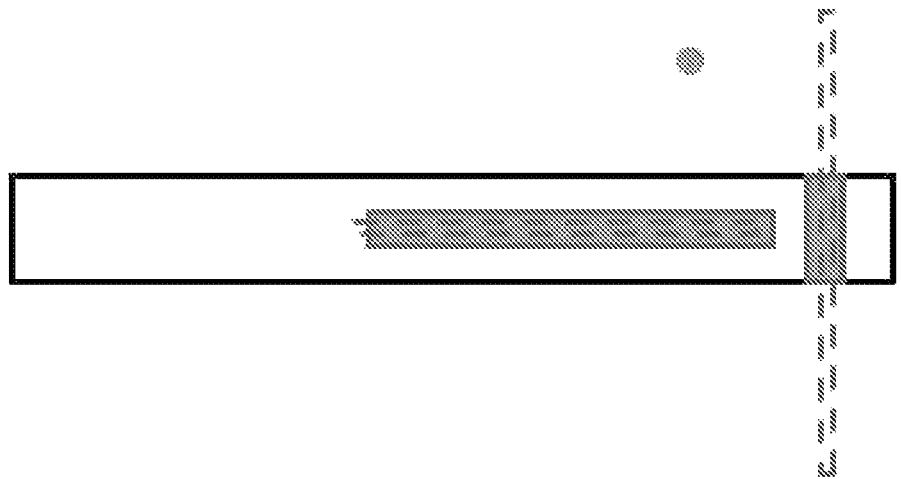
FIG. 53 shows a scenario where active point is outside of the imaging planes.

For example, if we want to recover the position of the point with respect to the convex array in the scenario shown in FIG. 53, we may start by observing its position in the linear array. The lateral position of the point along with the transformation between these two imaging planes will give us the point's elevational component with respect to the convex array. The axial position of the point in the image from the convex array represents the distance in the axial-elevational plane between the point and the closest transducer element. Since we now know the elevational component, we can easily obtain the axial component. Finally, the lateral component can be used as is in the image from the convex array.

Figure 54:
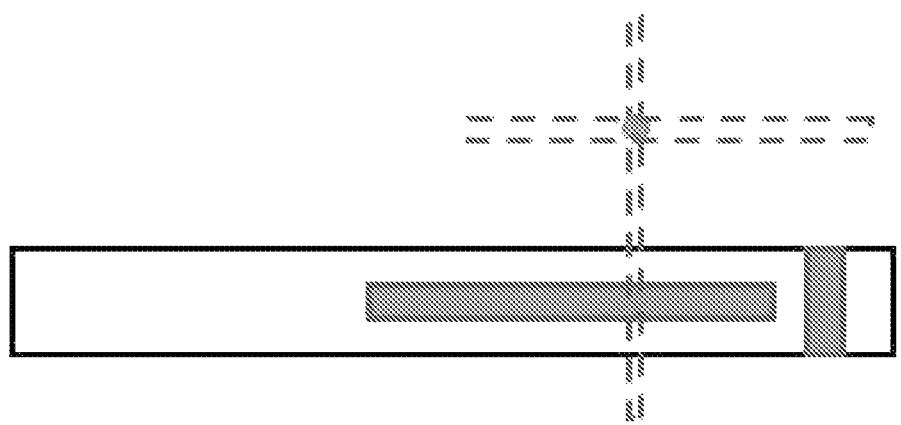
FIG. 54 shows a scenario demonstrating active point recovery with an alternate plane intersection method.

The scenario where the two ultrasound arrays are not perpendicular to each other is slightly more complicated. Instead of being able to simply use the lateral position from the linear array as the elevational component with respect to the convex array, the lateral position from the linear array will only restrict the position of the active point to a plane. Likewise, the lateral position from the convex array will also restrict the position of the active point to a plane. As shown in FIG. 54, since these two planes can both be interpreted with respect to the convex array, its intersection line can also be computed. Finally, the axial position in the image from the convex array will determine where along this intersection line satisfies the distance in the axial-elevational plane between the point and the closest transducer element.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An imaging system having real-time tracking and image registration, comprising:
    a photoacoustic source configured to provide an optically observable localized spot on a body of interest,
        wherein said optically observable localized spot is configured to emit a localized ultrasound pulse to operate as a fiducial marker;
    an optical imaging system configured to be arranged in view of said optically observable localized spot on said body of interest;
    an ultrasound probe configured to receive said localized ultrasound pulse from said optically observable localized spot;
    an optical image processing system configured to communicate with said optical imaging system to receive an optical image of at least a portion of said body of interest that includes said fiducial marker within said optical image,
        said optical image processing system being further configured to process said optical image to determine an optical spatial location of said fiducial marker;
    an ultrasound image processing system configured to:
        communicate with said ultrasound probe to receive a two-dimensional ultrasound image of at least the portion of said body of interest that includes said fiducial marker observed within said two-dimensional ultrasound image,
            the two-dimensional ultrasound image including post-beamformed RF data for B-mode,
        derive data approximately equal to pre-beamformed RF data using the post-beamformed RF data in an inverse beamforming calculation,
            wherein the inverse beamforming calculation is based on time reversal wavefronts associated with at least one pixel of said two-dimensional ultrasound image,
        perform photoacoustic beamforming using the data approximately equal to the pre-beamformed RF data to generate a two-dimensional photoacoustic image, and
        process said two-dimensional photoacoustic image to determine an ultrasound spatial location of said fiducial marker; and
    a registration system configured to communicate with said optical image processing system and said ultrasound image processing system to receive information associated with the optical spatial location and the ultrasound spatial location determined for said fiducial marker observed in said optical image and in said two-dimensional photoacoustic image,
        said registration system being further configured to determine a coordinate transformation that registers said optical image with said two-dimensional photoacoustic image based at least partially on said information associated with the optical spatial location and the ultrasound spatial location determined for said fiducial marker observed in said optical image and in said two-dimensional photoacoustic image.

2. The imaging system according to claim 1, wherein said photoacoustic source comprises:
    a pulsed light source configured to provide said fiducial marker at said optically observable localized spot.

3. The imaging system according to claim 2, wherein said pulsed light source is a pulsed laser diode.

4. The imaging system according to claim 2, wherein said photoacoustic source is further configured to:
    provide a plurality of fiducial markers at a plurality of localized spots,
    wherein said pulsed light source is a plurality of pulsed light sources.

5. The imaging system according to claim 4, wherein said pulsed light source is a laser diode and said plurality of pulsed light sources are pulsed laser diodes.

6. The imaging system according to claim 4, wherein said optical imaging system is configured to be arranged in view of said plurality of localized spots on said body of interest,
    wherein said ultrasound probe is further configured to receive a plurality of localized ultrasound pulses from said plurality of localized spots on said body of interest,
    wherein said optical image processing system is further configured to communicate with said optical imaging system to receive said optical image of at least a portion of said body of interest that includes said plurality of fiducial markers within said optical image,
        said optical image processing system being further configured to process said optical image to determine corresponding spatial locations of said plurality of fiducial markers.

7. The imaging system according to claim 6, wherein said ultrasound image processing system is configured to segment wavefronts generated by said plurality of fiducial markers observed in said two-dimensional ultrasound image to determine the corresponding spatial locations of said plurality of fiducial markers.

8. The imaging system according to claim 1, wherein said optical imaging system comprises a camera configured to be fixed within a room frame of reference.

9. The imaging system according to claim 1, wherein said optical imaging system comprises a camera configured to be fixed to said ultrasound probe.

10. The imaging system according to claim 1, further comprising:
    a piezoelectric transducer configured to transmit a signal to the ultrasound probe.

11. The imaging system according to claim 10, wherein said piezoelectric transducer is attached to a distal end of a surgical tool.

12. The imaging system according to claim 1, wherein said registration system is further configured to register at least one of real time optical images or preoperative images with said two-dimensional photoacoustic image in real time using said coordinate transformation.

13. The image processing system according to claim 1, wherein the ultrasound image processing system is further configured to:
determine a virtual source point associated with the post-beamformed RF data;
apply inverse and forward delay and sum beamforming to the virtual source point to produce other data approximately equal to pre-beamformed RF data; and
perform synthetic aperture beamforming using the other data approximately equal to the pre-beamformed RF data to generate the two-dimensional photoacoustic image.

14. An imaging system having real-time tracking and image registration, comprising:
a photoacoustic source configured to provide an optically observable localized spot on a body of interest,
wherein said optically observable localized spot is configured to emit a localized ultrasound pulse to operate as a fiducial marker;
an optical imaging system configured to be arranged in view of said optically observable localized spot on said body of interest;
an ultrasound probe configured to receive said localized ultrasound pulse from said optically observable localized spot on said body of interest;
an optical image processing system configured to:
communicate with said optical imaging system to receive an optical image of at least a portion of said body of interest that includes said fiducial marker within said optical image, and
process said optical image to determine an optical spatial location of said fiducial marker;
an ultrasound image processing system configured to:
communicate with said ultrasound probe to receive an ultrasound image of at least the portion of said body of interest that includes said fiducial marker observed within said ultrasound image,
wherein the ultrasound image includes post-beamformed RF data for B-mode,
derive data approximately equal to pre-beamformed RF data using the post-beamformed RF data in an inverse beamforming calculation,
wherein the inverse beamforming calculation is based on time reversal wavefronts associated with at least one pixel of said ultrasound image,
perform photoacoustic beamforming using the data approximately equal to the pre-beamformed RF data to generate a photoacoustic image, and
process said photoacoustic image to determine an ultrasound spatial location of said fiducial marker; and
a registration system configured to communicate with said optical image processing system and said ultrasound image processing system to receive information concerning the optical spatial location and the ultrasound spatial location determined for said fiducial marker in said optical image and in said ultrasound image,
said registration system being further configured to determine a coordinate transformation that registers said optical image with said photoacoustic image based at least partially on said information concerning the optical spatial location and the ultrasound spatial location determined for said fiducial marker observed in said optical image and in said photoacoustic image.

15. The imaging system according to claim 14, wherein said photoacoustic source comprises a pulsed light source configured to provide said fiducial marker at said optically observable localized spot.

16. The imaging system according to claim 15, wherein said pulsed light source is a pulsed laser diode.

17. The imaging system according to claim 15, wherein said photoacoustic source is further configured to:
provide a plurality of fiducial markers at a plurality of localized spots,
wherein said pulsed light source is a plurality of pulsed light sources.

18. The imaging system according to claim 17, wherein said pulsed light source is a pulsed laser diode and said plurality of pulsed light sources are pulsed laser diodes.

19. The imaging system according to claim 14, wherein said optical imaging system comprises a camera configured to be fixed within a room frame of reference.

20. The imaging system according to claim 14, wherein said optical imaging system comprises a camera configured to be fixed to said ultrasound probe.

21. The imaging system according to claim 14, further comprising:
a piezoelectric transducer configured to transmit a signal to the ultrasound probe.

22. The imaging system according to claim 21, wherein said piezoelectric transducer is attached to a distal end of a surgical tool.

23. An image processing system, comprising:
one or more memories; and
one or more processors, communicatively coupled to the one or more memories, configured to:
receive two-dimensional ultrasound image data of at least a portion of a body of interest that includes a fiducial marker,
the fiducial marker being produced by a photoacoustic source configured to provide an optically observable localized spot on the body of interest,
the optically observable localized spot being configured to emit a localized ultrasound pulse to operate as the fiducial marker, and
the two-dimensional ultrasound image data including post-beamformed RF data;
derive data approximately equal to pre-beamformed RF data using the post-beamformed RF data in an inverse beamforming calculation,
wherein the inverse beamforming calculation is based on time reversal wavefronts associated with at least one pixel of a two-dimensional ultrasound image associated with the two-dimensional ultrasound image data;
perform photoacoustic beamforming using the data approximately equal to the pre-beamformed RF data to produce a two-dimensional photoacoustic image and
process said two-dimensional photoacoustic image to determine an ultrasound spatial location of said fiducial marker in the two-dimensional photoacoustic image.

24. The image processing system according to claim 23, wherein the one or more processors are further configured to:

communicate with an ultrasound probe to receive the two-dimensional ultrasound image data of the at least the portion of said body of interest.

25. The image processing system according to claim 23, wherein a wavefront generated by said fiducial marker represents a time of flight (ToF) between said fiducial marker and the photoacoustic source.

26. The image processing system according to claim 23, wherein the one or more processors are configured further to:

provide information associated with the ultrasound spatial location of the two-dimensional photoacoustic image to a registration system, the registration system configured to determine a coordinate transformation to register an optical image associated with the two-dimensional photoacoustic image based at least partially on information concerning an optical spatial location determined for said fiducial marker observed in said optical image and the ultrasound spatial location determined in said two-dimensional photoacoustic image.

27. The image processing system according to claim 23, wherein an optical image is processed by an optical imaging system, the optical imaging system including a camera.

* * * * *